(12) United States Patent
Lapointe et al.

(10) Patent No.: US 6,556,977 B1
(45) Date of Patent: Apr. 29, 2003

(54) METHODS FOR SELECTING, DEVELOPING AND IMPROVING DIAGNOSTIC TESTS FOR PREGNANCY-RELATED CONDITIONS

(75) Inventors: Jerome Lapointe, Oakland, CA (US); Duane D. DeSieno, La Jolla, CA (US)

(73) Assignee: Adeza Biomedical Corporation, Sunnyvale, CA (US)

( * ) Notice: Subject to any disclaimer, the term of this patent is extended or adjusted under 35 U.S.C. 154(b) by 0 days.

(21) Appl. No.: 09/134,636

(22) Filed: Aug. 14, 1998

Related U.S. Application Data

(63) Continuation-in-part of application No. 08/912,133, filed on Aug. 14, 1997.

(51) Int. Cl.[7] .............................................. G06N 3/02

(52) U.S. Cl. .............................. 706/15; 706/23; 706/45

(58) Field of Search .............................. 706/15, 23, 45

(56) References Cited

U.S. PATENT DOCUMENTS

| | | | |
|---|---|---|---|
| 4,099,587 A | 7/1978 | Kaufmann | 177/210 |
| 4,874,963 A | 10/1989 | Alspector | 307/201 |
| 4,965,725 A | 10/1990 | Rutenberg | 364/413.1 |
| 5,036,479 A | 7/1991 | Prednis et al. | 364/580 |
| 5,091,170 A | 2/1992 | Navot | 424/9 |
| 5,096,830 A | 3/1992 | Senyei et al. | 436/65 |
| 5,130,936 A | 7/1992 | Sheppard et al. | 364/551.01 |
| 5,157,733 A | 10/1992 | Takeo et al. | 382/6 |
| 5,185,270 A | 2/1993 | Senyei et al. | 436/510 |
| 5,223,440 A | 6/1993 | Teng et al. | 436/510 |
| 5,236,846 A | 8/1993 | Senyei et al. | 436/65 |
| 5,241,620 A | 8/1993 | Ruggiero | 395/22 |
| 5,249,259 A | 9/1993 | Harvey | 395/13 |

(List continued on next page.)

FOREIGN PATENT DOCUMENTS

| | | |
|---|---|---|
| EP | 0387630 | 9/1990 |
| EP | 0557831 | 9/1993 |
| EP | 0616291 | 1/1994 |

(List continued on next page.)

OTHER PUBLICATIONS

Micheli–Tzanakou, E.; Yi, C.; Kostis, W.J.; Shindler, D.M.; Kostis, J.B., Myocardial infarction: diagnosis and vital status prediction using neural networks, Computers in Cardiology 1993, Proceedings., 1993, pp.: 229–232.*

(List continued on next page.)

*Primary Examiner*—Wilbert L. Starks, Jr.
(74) *Attorney, Agent, or Firm*—Stephanie L. Seidman; Heller Ehrman White & McAuliffe, LLP

(57) ABSTRACT

Methods are provided for developing medical diagnostic tests using decision-support systems, such as neural networks. Patient data or information, typically patient history or clinical data, are analyzed by the decision-support systems to identify important or relevant variables and decision-support systems are trained on the patient data. Patient data are augmented by biochemical test data, or results, where available, to refine performance. The resulting decision-support systems are employed to evaluate specific observation values and test results, to guide the development of biochemical or other diagnostic tests, too assess a course of treatment, to identify new diagnostic tests and disease markers, to identify useful therapies, and to provide the decision-support functionality for the test. Methods for identification of important input variables for a medical diagnostic tests for use in training the decision-support systems to guide the development of the tests, for improving the sensitivity and specificity of such tests, and for selecting diagnostic tests that improve overall diagnosis of, or potential for, a disease state and that permit the effectiveness of a selected therapeutic protocol to be assessed are provided. The methods for identification can be applied in any field in which statistics are used to determine outcomes. A method for evaluating the effectiveness of any given diagnostic test is also provided.

85 Claims, 14 Drawing Sheets

U.S. PATENT DOCUMENTS

| | | | |
|---|---|---|---|
| 5,251,626 A | 10/1993 | Nickolls et al. | 607/14 |
| 5,279,941 A | 1/1994 | Lessey | 435/7.21 |
| 5,281,522 A | 1/1994 | Senyei et al. | 435/7.9 |
| 5,299,284 A | 3/1994 | Roy | 395/22 |
| 5,301,681 A | 4/1994 | DeBan et al. | 128/736 |
| 5,304,468 A | 4/1994 | Phillips et al. | 435/14 |
| 5,321,492 A | 6/1994 | Detwiler et al. | 356/73 |
| 5,331,550 A | 7/1994 | Stafford et al. | 364/413.2 |
| 5,392,403 A | 2/1995 | Kaufmann | 395/275 |
| 5,405,362 A | 4/1995 | Kramer et al. | 607/5 |
| 5,455,890 A | 10/1995 | Wang | 395/22 |
| 5,463,548 A | 10/1995 | Asada et al. | 364/413.02 |
| 5,468,619 A | 11/1995 | Senyei et al. | 435/7.94 |
| 5,473,537 A | 12/1995 | Glazer et al. | 364/419.2 |
| 5,474,927 A | 12/1995 | Anderson et al. | 435/7.21 |
| 5,480,776 A | 1/1996 | Dullien | 435/7.9 |
| 5,481,481 A | 1/1996 | Frey et al. | 364/551.01 |
| 5,491,627 A | 2/1996 | Zhang et al. | 364/413.2 |
| 5,503,161 A | 4/1996 | Van Den Heuvel | 128/773 |
| 5,516,702 A | 5/1996 | Senyei et al. | 436/510 |
| 5,533,519 A | 7/1996 | Radke et al. | 128/777 |
| 5,544,308 A | 8/1996 | Giordano et al. | 395/183.02 |
| 5,560,370 A | 10/1996 | Verrier et al. | 128/705 |
| 5,565,364 A | 10/1996 | Schaefer et al. | 436/43 |
| 5,590,665 A | 1/1997 | Kanai | 128/898 |
| 5,594,637 A | 1/1997 | Eisenberg et al. | 395/202 |
| 5,622,171 A | 4/1997 | Asada et al. | 364/413.01 |
| 5,623,939 A | 4/1997 | Garfield | 128/733 |
| 5,627,907 A | 5/1997 | Gur et al. | 382/128 |
| 5,687,716 A | 11/1997 | Kaufmann et al. | 128/630 |
| 5,690,103 A | 11/1997 | Groth et al. | 128/632 |
| 5,817,461 A | 10/1998 | Austin et al. | 435/6 |
| 5,878,746 A | 3/1999 | Lemelson et al. | 600/407 |

FOREIGN PATENT DOCUMENTS

| | | |
|---|---|---|
| EP | 0610805 | 3/1994 |
| EP | 0644414 | 3/1995 |
| WO | 9425933 | 11/1994 |
| WO | 9427490 | 12/1994 |
| WO | 9603929 | 2/1996 |
| WO | 9612187 | 4/1996 |
| WO | 9705553 | 2/1997 |
| WO | 9709678 | 3/1997 |
| WO | 9717891 | 5/1997 |
| WO | 9729447 | 8/1997 |
| WO | 9730996 | 8/1997 |

OTHER PUBLICATIONS

Kupinski, M.A.; Giger, M.L., Feature selection and classifiers for the computerized detection of mass lesions in digital mammography, Neural Networks, 1997., International Conference on, Volume: 4, pp.: 2460–2463 vol. 4.*

Burke, H.B., Evaluating artificial neural networks for medical applications, Neural Networks, 1997., International Conference on Volume: 4, 1997, pp.: 2494–2495 vol. 4.*

El–Deredy, W.; Branston, N.M., Identification of relevant features in /sup 1/H MR tumour spectra using neural networks, Articical Neural Networks, 1995., Fourth International Conference on, 1995, pp.: 454–458.*

Shiyi Xu; Dias, G.P.; Waignjo, P.; Bole Shi, Testability prediction for sequential circuits using neural networks, Test Symposium, 1997. (ATS '97). Proceedings., Sixth Asian, 1997, pp.: 48–53.*

Rachid, S.; Niki, N.; Nishitani, H.; Nakamura, S.; Mori, S., Segmentation of sputum color image for lung cancer diagnosis, Image Processing, 1997. Proceedings., International Conference on Volume: 1, 1997, pp.: 243–246 vol. 1.*

Wong, F.S.; Wang, P.Z.; Goh, T.H., Fuzzy neural systems for decision making, Neural Networks, 1991. 1991 IEEE International Joint Conference on, 1991, pp.: 1625–1637 vol. 2.*

Al–Jumah, A.A.; Arslan, T., Artificial neural network based multiple fault diagnosis in digital circuits, Circuits and Systems, 1998. ISCAS '98. Proceedings of the 1998 IEEE International Symposium on, Volume: 2, 1998, pp.: 304–307 vol. 2.*

Ouyang, N.; Ikeda, M.; Yamauchi, K., Using a neural network to diagnose anterior wall myocardial infarction, Neural Networks, 1997., International Conference on, Volume: 1, 1997, pp.: 56–61 vol. 1.*

Gorzalczany, M.B., An idea of the application of fuzzy neural networks to medical decision support systems, Industrial Electronics, 1996. ISIE '96., Proceedings of the IEEE International Symposium on, Volume: 1, 1996, pp.: 398–403 vol. 1.*

Furundzic, D.; Djordjevic, M.; Bekic, A., Artificial neural networks for early breast carcinoma detection, Neural Networks for Identification, Control, Robotics, and Signal/Image Processing, 1996. Proceedings., International Workshop on, 1996, pp.: 35.*

Alvager et al., The use of artificial neural networks in biomedical technologies: An introduction, *Biomed. Instrument. Technol.* 315–322 (1994).

Arden, "Internal Medicine:Internist", (available at http://www.spi.org/cgi...eeit&csum=110562327913 on Dec. 8, 1996).

"Artificial intelligence systems in routine clinical use", (available on http://www.gretmar.com/ailist/list.html).

Baxt, "Analysis of the clinical variables driving decision in an articial neural network trained to identify the presence of myocardial infarction", *Ann. Emerg. Med.* 21:1439–1444 (1992).

Baxt, "Application of artificial neural networks to clinical medicine", *Lancet* 346:1135–1138 (1995).

Baxt, "Bootstrapping confidence intervals for clinical input variable effects in a network trained to indentify the presence of acute myocardial infarction", *Neural Comput.*7:624–638 (1995).

Baxt, "Improving the accuracy of an artificial neural network using multiple differently trained networks", *Neural Comput.*772–780 (1992).

Baxt, "Use of an articial neural network for the diagnosis of myocardial infarction", *Ann. Intern. Med.* 115:843–848 (1991).

Baxt, "Complexity, choas and human physiology: the justification for non–linear neural computational analysis", *Cancer Lett.* 77:85–93 (1994).

Baxt, "Use of an artificial neural network for data analysis in clinical decision–making: The diagnosis of acute coronary occlusion", *Neural Comput.* 2: 480–489 (1990).

Beksac et al., "An artificial intelligent diagnosis system with neural networks to determine genetical disorders and fetal health by using maternal serum markers", *Eur. J. Obstet. Gynecol. Reprod. Biol.* 59:131–136 (1995).

Benediktsson et al., "Parallel consensual neural networks with optimally weighted output", *Proceedings of World Congress on Neural Networks* 3:129–137, (1994).

"BioComp Systems, Inc.: Systems that learn, adapt and evolve", (available on http://www.bio–comp.com/products.htm on Nov. 21, 1996).

Blinowska et al., "Diagnostica—A bayesian decision–aid system—applied to hypertension diagnosis", *IEEE Transact. Biomed. Engin.* 40:230–235 (1993)

Brickley et al., "Performance of a neural network trained to make third–molar treatment–planning decisions", *Med. Decis. Making* 16:153–160 (1996).

Brown et al., "Finite training sample size effects on neural network pattern classification in low–dimensional feature space", pp. 96–101.

Burke et al., "Artificial neural networks for outcome prediction in cancer", pp. 53–56.

Creasy and Resnik, "Maternal–fetal medicine: Principles and practice", Chapter 36, Sec. 18, p. 657, 1989.

Davis, et al., "Production systems as a representation for a knowledge based consultation program", *Artific. Intellig.* 8:15–45 (1977).

Database Derwent WPI #009580780, citing European patent 557831 A, Instrument for determining optimum delivery time of foetus.

Diller, W., "Horus computer–enhanced diagnostics", *In Vivo: The Business and Medicine Report* pp. 3–10, 1997.

Erickson, "What is cognitive computing!, Part 2 of 3", (available at http://www.spi.org/cgi...seeit&csum=16068819102 on Dec. 8, 1996).

Fahlman et al., "The cascade–correlation learning architecture", *Adv. Neur. Informat. Process. Systems* 2:524–532 (1989).

Fahlman, "Fast learning variations on back–propagation: An empirical study", *Proc. 1988 Connectionist Models Summer School*, Pittsburgh, pp. 38–51 (1988).

Haddawy, "Decision systems and artificial intelligence laboratory", (available at http:/www.cs.uwm.edu/;;public/dsail/ on Nov. 21, 1996).

Kahn, "Mammonet: Mammography decision supports system", (avaiable at http://www.mcw.edu/midas/mammo.html on Nov. 21, 1996).

Keller, "Artificial neural networks in medicine", Handout/Technology brief, Pacific Nortwest Laboratory.

Keller et al., "A novel approach to modeling and diagnosing the cardiovascular system", (available at http://www.emsl.pnl.gov:2080/docs/c...ural/papers2/keller.wcnn95.abs.html on Nov. 21, 1996).

Kim et al., "Ensemble competitive learning neural networks with reduce input dimension", *Intl. J . of Neural Systems* 6(2):133–142, 1995.

Kol et al., "Interpretation of nonstress test by artificial neural network", *Amer. J. Obstet. Gynecol.* 172:1372–1379 (1995).

Lapuerta et al., "Use of neural networks in predicting the risk of coronary artery disease", *Computers and Biomedical Research* 28:38–52 (1995).

Logical Designs Consulting, Inc., "Thinks™ and ThinksPro™ Neural networks for windows: Your complete neural network development environment".

Maclin et al., "Using neural networks to diagnose cancer", *J. Med. Systems* 15:11–19 (1991).

Mobley, et al., "Artifical neural network predictions of lengths of stay on a post coronary care unit", *Heart and Lung* 24:251–256 (1995).

Modai, et al., "Clinical decisions for psychiatric inpatients and their evaluation by trained neural networks", *Methods of Information in Medicine* 32:396–399 (1993).

Moneta et al., "Automated diagnosis and disease characterization using neural network analysis", *Instittute of Electrical and Electronics Engineers—Emergent Innovations on Information Transfer Processing and decision Making, Chicago*, vol. 1 of 2: 123–128 (1992).

"Multivariate statistical data reduction method", (available on http://www.spi.org/cgi...seeit&csum=17396875558 on Dec. 8, 1996).

Nejad et al., "Significance measure and data dependency in classification methods", *Instit. Elect. Electron. Engineers Intl. Conference on Neural Network Proceedings*, Australia: 1816–1822 (1995).

"Neural informatics pearls of wisdom", (availalbe on http://www.smi.stanford.edu/people/...hysiology/Neuro_Pearls.html#ANN–app on Nov. 21, 1996).

*Neural Networks & intelligent systems newsletter*, Derwent Direct, Issue 3, (August, 1995).

NTIS Published Search—Neural networks: Applications, Sep. 1986–present.

Ota and Maki, "Evaluation of autoantibody and CA125 in the diagnosis of endometriosis or adenomyosis", *Medicinal Research Reviews* 18(8):309 (1990).

Pattichis et al., "Neural network Models in EMG Diagnosis", *IEEE Trans. Biomed. Engin* 42:486–495 (1995).

Penny, et al., "Neural networks in Clinical Medicine", *Med. Decis. Marking* 16:386–398 (1996).

Plate, "Re: neural nets", (availalbe at http://www.gsf.de/msr/sift/msg00649.html on Nov. 21, 1996).

Rogers, et al.., "Artificial neural networks for early detection and diagnosis of breast and ovarian cancer", *Cancer Letters* 77:79–83 (1994).

Ruck, et al., "Feature selection in feed–forward neural networks", *Neural Networks Computing* 20:40–48 (1990).

Rutledge, "An overview of medical decision–support systems", (available at http://www.medg.lcs.mit.edu/BIRT/absgeoff.htm on Nov. 21, 1996).

Sammet, "Patterm recognition applied to early diagnosis of heart attacks", (available at http://www.spi.org/cpi...seeit&csum=19641717994 on Dec. 8, 1996.

Siganos, "Neural networks in medicine", (available at http://scorch.doc.ic.ac.uk/~nd/suprise_96/journal/vol2/ds12/article2.html on Nov. 21, 1996).

Snow et al., "Artificial neural networks in the diagnosis and prognosis of prostate cancer: A pilot study", *J. Urol.*152:1923–1926 (1994).

Solms, et al., "A neural network diagnostic tool for the chronic fatigue syndrome", International Conference on Neural Networks, Paper No. 108 (1996).

Stamey, "ProstAsure™: An information resource", (available at http://www.labcorp.com/prost3.htm on Nov. 21, 1996).

Swaine, "Programming Paradigms—part 2", (available at http://www. spi.org/cgi...seeit&scum=17808028563 on Dec. 8, 1996).

Turner, "Technology brief: Coronary artery disease diagnosis" (available on http://www.emsl.gov:2080/docs/cie/techbrief/CAD.techbrief.html on Nov. 21, 1996).

Utans, et al., "Selecting neural network architectures via the prediction risk: Application to corporate bond rating prediction", *Proceedings of the First International Conference on Artificial Intelligence Applications on Wall Street, Washington D.C.,* IEEE Computer Society Press. pp. 35–41 (1993).

Utans, et al., "Input variable selection for neural networks: Applications to predicting the U.S. Business Cycle", IEEE pp. 118–122 (1995).

van Dyne et al., "Using inductive machine learning, expert systems and case based reasoning to predict preterm delivery in pregnant women", Database and Expert Systems Applications, 5th Int'l Conf., DEXA 1994 Proceedings, Athens, Greece, Sept. 7–9, 1994, pp. 690–702.

van Dyne et al., "Using machine learning and expert systems to predict preterm delivery in pregnant women", Proceedings of the Tenth Conference on Artificial Intelligence for Applications, San Antonia, TX, Mar. 1–4, 1994, pp. 344–350.

Weinstein, et al., "Neural networks in the biomedical sciences: A survey of 386 publications since the beginning of 1991", pp. 121–126.

Wenskay, "Neural networks: a prescription for effective protection", *The Computer Lawyer* 8:12–23 (1991).

Widman, "Expert systems in medicine", (available on http://amplatz.uokhsc.edu/acc95–expert–systems.html on Nov. 21, 1996).

Wilding, et al., "Application of Backpropogation neural networks to diagnosis of breast and ovarian cancer", *Cancer Letters* 77:145–153 (1994).

Young, "Diagnosis of acute cardiac ischemia", (available on http://www.library.ucs...1/Originals/young.html on Nov. 21, 1996).

Burke, Evaluating artificial neural networks for medical applications, *International Conference on Neural Networks* 4:2494–2495 (1997).

El–Deredy et al., Identification of relevant features in /sup 1/H MR tumour spectra using neural networks, *Fourth International Conference on Artificial Neural Networks* pp. 454–458 (1995).

Furundzic et al., Artificial neural networks for early breast carcinoma detection, *International Workshop on Neural Networks for Identification, Control, Robotics, and Signal/Image Processing* 355–359 (1996).

Gorzalczany, An idea of the application of fuzzy neural networks to medical decision support system, *Proceedings of the IEEE International Symposium on Industrial Electronics* 1:398–403 (1996).

Kupinski et al., Feature selection and classifiers for the computerized detection of mass lesions in digital mammography, *International Conference on Neural Networks* 4:2460–2463 (1997).

Micheli–Tzanakou et al., Myocardial infarction: diagnosis and vital status prediction using neural networks, *Computers in Cardiology* pp. 229–232 (1993).

Rachid et al., Segmentation of sputum color image for lung cancer diagnosis *International Conference on Image Processing* 1:243–246 (1997).

Shiyi Xu et al., Testability prediction for sequential circuis using neural networks, *Sixth Asian Test Symposium* pp. 48–53 (1997).

Wong et al., Fuzzy neural systems for decision making, *IEEE International Joint Conference on Neural Networks* 2:1625–1637 (1991).

Al–Jumah et al., Artificial neural network based multiple fault diagnosis in digital circuits, Proceedings of teh 1998 IEEE International Symposium on Circuits and Systems, vol. 2, pp. 304–307 (1998).

Brownell, Neural networks for sensor management and diagnostics, Proceedings of the IEEE Aerospace and Electronics Conference, vol. 3, pp. 923–929 (1992).

Marko et al., Automotive diagnostics using trainable classifiers: statistical testing adn paradigm selection, IJCNN International Joint Conference on Neural Networks, vol. 1, pp. 33–38 (1990).

Michel et al., Prognosis with neural networks using statistically based feature sets, Computer–Based Medical Systems, Proceedings of Fifth Annual IEEE Symposium pp. 695–702 (1992).

Ouyang et al., Using a neural network to diagnose anterior wall myocardial infarction, International Conference on Neural Networks, vol. 1, pp. 56–61 (1997).

Sheppard et al., A neural network for evaluting diagnostic evidence, Aerospace and Electronics Conference, NAECON, Proceedings of the IEEE 1991 National, pp. 717–723 vol. 2, pp. 717–723 (1991).

* cited by examiner

| Pre-Term Delivery Risk Assessment Software: Data Entry Screen | ⊠ |
|---|---|

Lab ID #: _____

PATIENT INFORMATION

Name(last) [____] First [____] M [__]

DOB [mm/dd/yy]

Ethnic origin: ☐ Caucasian ☐ African American ☐ Asian ☐ Hispanic ☐ Native American ☐ Other Marital status: ☐ Married ☐ Single ☐ Divorced/Seperated ☐ Widowed ☐ Living with partner ☐ Other

PATIENT HISTORY AND CLINICAL INFORMATION

At the time of sampling, was the patient experiencing signs and symptoms of possible preterm labor?  ☐ YES  ☐ NO If yes, please mark all that apply.

☐ Uterine contractions with or without pain
  Number/hr. ☐ <1  ☐ 1-3  ☐ 4-6  ☐ 7-9  ☐ 10-12  ☐ >12

☐ Vaginal bleeding
  ☐ Trace ☐ Med. ☐ Gross

☐ Patient is not "feeling right"

☐ Bleeding during the second or third trimester

☐ Intermittent lower abdominal pain, dull, lowback pain, pelvic pressure

☐ Change in vaginal discharge-amount, color, or consistency

☐ Menstrual-like cramping (with or without diarrhea)

Gestational Age: EGA by first trimester sono [ww.d]  EGA by LMP [ww.d]  EGA at sampling [ww.d]

Previous Pregnancy: Please mark all that apply:

☐ Previous pregnancy: no complications
☐ History of Preterm delivery
  If Yes, how many? ☐ 1  ☐ 2  ☐ >2
☐ History of Preterm PROM
☐ History of incompetent cervix
☐ History of PIH/preeclampsia
☐ History of SAB prior to 20 wks.

Current Pregnancy:  G: [__]  P: [__]  A: [__]

☐ Multiple Gestation ☐ Twins ☐ Triplets ☐ Quads
☐ Uterine or cervical abnormality
☐ Cerclage
☐ Gestational Diabetes
☐ Hypertensive Disorders Cervical Status immediately following sample collection:
Dilatation(cm) ☐ <1 ☐ 1 ☐ 1-2 ☐ 2 ☐ 2-3 ☐ 3 ☐ >3 ☐ Unk. Cervical consistency ☐ Firm ☐ Mod ☐ Soft Medications at Time of Test (check all that apply)
☐ Antibiotics ☐ Corticosteroids ☐ Tocolytis ☐ Insulin ☐ Antihypertensives ☐ None ☐ Unknown Qualitative fFN Elisa Test Results: ☐ Positive    ☐ Negative

[ Calculate risk ]    [ Cancel ]

FIG. 8

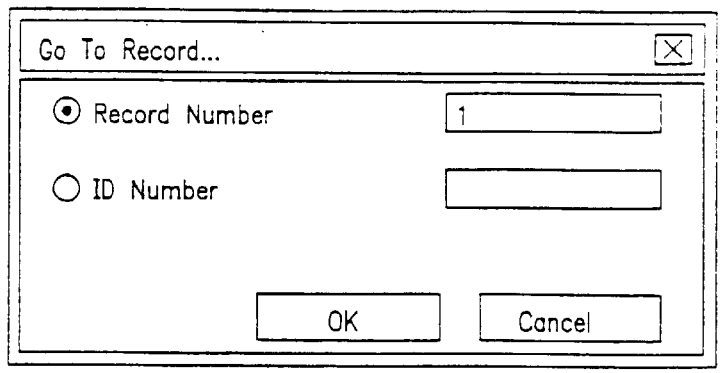
FIG. 9
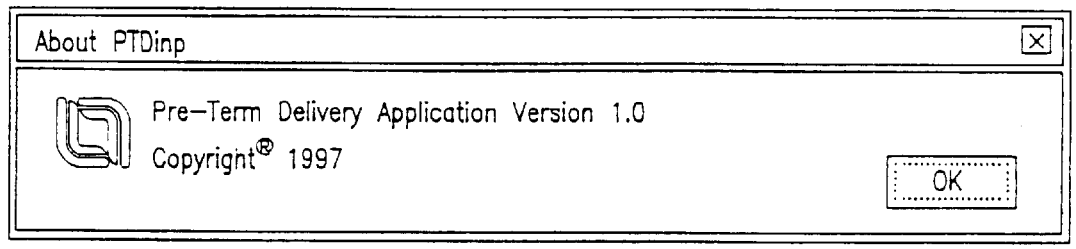
FIG. 10
Pre-Term Delivery Risk Assesment Software:
Test Report Form
| Lab ID # | |
|---|---|
| Patient Name: | |
| Pre-term Delivery Risk <34.6wks: | 0.288432 |
| Pre-term delivery Risk <7 days: | 0.001721 |
| Pre-term Delivery Risk <14 days: | 0.001544 |
FIG. 11A

| Pre-Term Delivery Risk Assessment Software: Data Entry Screen | Lab ID # | ☒ |

| PATIENT INFORMATION |
|---|

| Name(last)   First   M | Ethnic origin: ☐Caucasian ☐African American ☐Asian ☐Hispanic ☐Native American ☐Other |
|---|---|
| DOB mm/dd/yy | Marital status: ☐Married ☐Single ☐Divorced/Seperated ☐Widowed ☐Living with partner ☐Other |

| PATIENT HISTORY AND CLINICAL INFORMATION |
|---|

At the time of sampling, was the patient experiencing signs and symptoms of possible preterm labor?  ☐YES ☐NO If yes, please mark all that apply.
☐ Uterine contractions with or without pain      ☐ Bleeding during the second or third trimester
   Number/hr. ☐ <1   ☐ 1-3   ☐ 4-6      ☐ Intermittent lower abdominal pain, dull, low backpain,
              ☐ 7-9  ☐ 10-12 ☐ >12         pelvic pressure ☐ Vaginal bleeding                              ☐ Change in vaginal discharge-amount, color, or
   ☐Trace ☐Med. ☐Gross                             consistency
☐ Patient is not feeling right                  ☐ Menstrual-like cramping(with or without diarrhea)

| Gestational Age: EGA by first trimester sono ww.d   EGA by LMP ww.d   EGA at sampling ww.d |
|---|

| Previous Pregnancy: Please mark all that apply. | Current Pregnancy:  G:   P:   A: |
|---|---|
| ☐ Previous pregnancy: no complications | ☐ Multiple Gestation ☐Twins ☐Triplets ☐Quads |
| ☐ History of Preterm delivery | ☐ Uterine or cervical abnormality |
|    If Yes, how many? ☐1  ☐2  ☐>2 | ☐ Cerclage |
| ☐ History of Preterm PROM | ☐ Gestational Diabetes |
| ☐ History of incompetent cervix | ☐ Hypertensive Disorders |
| ☐ History of PIH/preeclampsia | |
| ☐ History of SAB prior to 20 wks. | |

Cervical status immediately following sample collection:                      ☐Firm  ☐Soft
Dilatation(cm)☐<1 ☐1 ☐1-2 ☐2 ☐2-3 ☐3 ☐>3 ☐Unknown   Cervical consistency ☐Mod Medications at Time of Test(check all that apply)
☐ Antibiotics ☐Corticosteroids   ☐Tocolytis ☐Insulin ☐Antihypertensives ☐None ☐Unknown Qualitative fFN Elisa Test Results: ☐ Positive        ☐ Negative

| Pre-term Delivery Risk <34.6wks: | 0.288432 |
|---|---|
| Pre-term Delivery Risk <7 days: | 0.001721 |
| Pre-term Delivery Risk <14 days: | 0.001544 |

FIG. 11B

METHODS FOR SELECTING, DEVELOPING AND IMPROVING DIAGNOSTIC TESTS FOR PREGNANCY-RELATED CONDITIONS

This application is a continuation-in-part of U.S. application Ser. No. 08/912,133, entitled "METHOD FOR SELECTING MEDICAL AND BIOCHEMICAL DIAGNOSTIC TESTS USING NEURAL NETWORK-RELATED APPLICATIONS" to Jerome Lapointe and Duane DeSieno, filed Aug. 14, 1997.

This application is also related to U.S. application Ser. No. 08/798,306 entitled "METHOD FOR SELECTING MEDICAL AND BIOCHEMICALDIAGNOSTIC TESTS USING NEURAL NETWORK-RELATED APPLICATIONS" to Jerome Lapointe and Duane DeSieno, filed Feb. 7, 1997. This application is also a related to U.S. application Ser. No. 08/599,275 and to International PCT application No. PCT/US97/02104 (published as WO 97/29447 published on Aug. 14, 1997), each entitled "METHOD FOR DEVELOPING MEDICAL AND BIOCHEMICAL DIAGNOSTIC TESTS USING NEURAL NETWORKS" to Jerome Lapointe and Duane DeSieno, filed Feb. 9, 1997. U.S. application Ser. No. 08/798,306 is a continuation-in-part of U.S. application Ser. No. 08/599,275. U.S. application Ser. 08/599,275, entitled "METHOD FOR DEVELOPING MEDICAL AND BIOCHEMICAL DIAGNOSTIC TESTS USING NEURAL NETWORKS" to Jerome Lapointe and Duane DeSieno, filed Feb. 9, 1996 claims priority under 35 U.S.C. §119(e) to U.S. provisional application Ser. No. 60/011,449, entitled "METHOD AND APPARATUS FOR AIDING IN THE DIAGNOSIS OF ENDOMETRIOSIS USING A PLURALITY OF PARAMETERS SUITED FOR ANALYSIS THROUGH A NEURAL NETWORK" to Jerome Lapointe and Duane DeSieno, filed Feb. 9, 1996.

The subject matter of each of the above-noted applications and provisional application is herein incorporated in its entirety by reference thereto.

MICROFICHE APPENDIX

Three computer Appendices containing computer program source code for programs described herein have been submitted in prior applications. The Computer Appendices are each incorporated herein by reference in its entirety. Appendix III is provided herewith.

Thus, a portion of the disclosure of this patent document contains material that is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This subject matter of the invention relates to the use of prediction technology, particularly nonlinear prediction technology, for the development of medical diagnostic aids for pregnancy-related and fertility-related conditions. In particular, training techniques operative on neural networks and other expert systems with inputs from patient historical information for the development of medical diagnostic tools and methods of diagnosis are provided.

BACKGROUND OF THE INVENTION

Data Mining, Decision Support-Systems and Neural Networks

A number of computer decision-support systems have the ability to classify information and identify patterns in input data, and are particularly useful in evaluating data sets having large quantities of variables and complex interactions between variables. These computer decision systems which are collectively identified as "data mining" or "knowledge discovery in databases" (and herein as decision-support systems) rely on similar basic hardware components, e.g., personal computers (PCS) with a processor, internal and peripheral devices, memory devices and input/output interfaces. The distinctions between the systems arise within the software, and more fundamentally, the paradigms upon which the software is based. Paradigms that provide decision-support functions include regression methods, decision trees, discriminant analysis, pattern recognition, Bayesian decision theory, and fuzzy logic. One of the more widely used decision-support computer systems is the artificial neural network.

Artificial neural networks or "neural nets" are parallel information processing tools in which individual processing elements called neurons are arrayed in layers and furnished with a large number of interconnections between elements in successive layers. The functioning of the processing elements are modeled to approximate biologic neurons where the output of the processing element is determined by a typically non-linear transfer function. In a typical model for neural networks, the processing elements are arranged into an input layer for elements which receive inputs, an output layer containing one or more elements which generate an output, and one or more hidden layers of elements therebetween. The hidden layers provide the means by which non-linear problems may be solved. Within a processing element, the input signals to the element are weighted arithmetically according to a weight coefficient associated with each input. The resulting weighted sum is transformed by a selected non-linear transfer function, such as a sigmoid function, to produce an output, whose values range from 0 to 1, for each processing element. The learning process, called "training", is a trial-and-error process involving a series of iterative adjustments to the processing element weights so that a particular processing element provides an output which, when combined with the outputs of other processing elements, generates a result which minimizes the resulting error between the outputs of the neural network and the desired outputs as represented in the training data. Adjustment of the element weights are triggered by error signals. Training data are described as a number of training examples in which each example contains a set of input values to be presented to the neural network and an associated set of desired output values.

A common training method is backpropagation or "backprop", in which error signals are propagated backwards through the network. The error signal is used to determine how much any given element's weight is to be changed and the error gradient, with the goal being to converge to a global minimum of the mean squared error. The path toward convergence, i.e., the gradient descent, is taken in steps, each step being an adjustment of the input weights of the processing element. The size of each step is determined by the learning rate. The slope of the gradient descent includes flat and steep regions with valleys that act as local minima, giving the false impression that convergence has been achieved, leading to an inaccurate result.

Some variants of backprop incorporate a momentum term in which a proportion of the previous weight-change value is added to the current value. This adds momentum to the algorithm's trajectory in its gradient descent, which may prevent it from becoming "trapped" in local minima. One backpropagation method which includes a momentum term is "Quickprop", in which the momentum rates are adaptive. The Quickprop variation is described by Fahlman (see, "Fast Learning Variations on Back-Propagation: An Empirical Study", *Proceedings on the* 1988 *Connectionist Models Summer School*, Pittsburgh, 1988, D. Touretzky, et al., eds., pp.38–51, Morgan Kaufmann, San Mateo, Calif.; and, with Lebriere, "The Cascade-Correlation Learning Architecture", *Advances in Neural Information Processing Systems* 2,(Denver, 1989), D. Touretzky, ed., pp. 524–32. Morgan Kaufmann, San Mateo, Calif.). The Quickprop algorithm is publicly accessible, and may be downloaded via the Internet, from the Artificial Intelligence Repository maintained by the School of Computer Science at Carnegie Mellon University. In Quickprop, a dynamic momentum rate is calculated based upon the slope of the gradient. If the slope is smaller but has the same sign as the slope following the immediately preceding weight adjustment, the weight change will accelerate. The acceleration rate is determined by the magnitude of successive differences between slope values. If the current slope is in the opposite direction from the previous slope, the weight change decelerates. The Quickprop method improves convergence speed, giving the steepest possible gradient descent, helping to prevent convergence to a local minimum.

When neural networks are trained on sufficient training data, the neural network acts as an associative memory that is able to generalize to a correct solution for sets of new input data that were not part of the training data. Neural networks have been shown to be able to operate even in the absence of complete data or in the presence of noise. It has also been observed that the performance of the network on new or test data tends to be lower than the performance on training data. The difference in the performance on test data indicates the extent to which the network was able to generalize from the training data. A neural network, however, can be retrained and thus learn from the new data, improving the overall performance of the network.

Neural nets, thus, have characteristics that make them well suited for a large number of different problems, including areas involving prediction, such as medical diagnosis.

Neural Nets and Diagnosis

In diagnosing and/or treating a patient, a physician will use patient condition, symptoms, and the results of applicable medical diagnostic tests to identify the disease state or condition of the patient. The physician must carefully determine the relevance of the symptoms and test results to the particular diagnosis and use judgement based on experience and intuition in making a particular diagnosis. Medical diagnosis involves integration of information from several sources including a medical history, a physical exam and biochemical tests. Based upon the results of the exam and tests and answers to the questions, the physician, using his or her training, experience and knowledge and expertise, formulates a diagnosis. A final diagnosis may require subsequent surgical procedures to verify or to formulate. Thus, the process of diagnosis involves a combination of decision-support, intuition and experience. The validity of a physician's diagnosis is very dependent upon his/her experience and ability.

Because of the predictive and intuitive nature of medical diagnosis, attempts have been made to develop neural networks and other expert systems that aid in this process. The application of neural networks to medical diagnosis has been reported. For example, neural networks have been used to aid in the diagnosis of cardiovascular disorders (see, e.g., Baxt (1991) "Use of an Artificial Neural Network for the Diagnosis of Myocardial Infarction," *Annals of Internal Medicine* 115:843; Baxt (1992) "Improving the Accuracy of an Artificial Neural Network Using Multiple Differently Trained Networks," *Neural Computation* 4:772; Baxt (1992), "Analysis of the clinical variables that drive decision in an artificial neural network trained to identify the presence of myocardial infarction," *Annals of Emergency Medicine* 21:1439; and Baxt (1994) "Complexity, chaos and human physiology: the justification for non-linear neural computational analysis," *Cancer Letters* 77:85). Other medical diagnostic applications include the use of neural networks for cancer diagnosis (see, e.g., Maclin, et al. (19910 "Using Neural Networks to Diagnose Cancer" *Journal of Medical Systems* 15:11–9; Rogers, et al. (1994) "Artificial Neural Networks for Early Detection and Diagnosis of Cancer" *Cancer Letters* 77:79–83; Wilding, et al. (1994) "Application of Backpropogation Neural Networks to Diagnosis of Breast and Ovarian Cancer" *Cancer Letters* 77:145–53), neuromuscular disorders (Pattichis, et al. (1995) "Neural Network Models in EMG Diagnosis", *IEEE Transactions on Biomedical Engineering* 42:5:486–495), and chronic fatigue syndrome (Solms, et al. (1996) "A Neural Network Diagnostic Tool for the Chronic Fatigue Syndrome", International Conference on Neural Networks, Paper No. 108). These methodologies, however, fail to address significant issues relating to the development of practical diagnostic tests for a wide range of conditions and does not address the selection of input variables.

Computerized decision-support methods other than neural networks have been reported for their applications in medical diagnostics, including knowledge-based expert systems, including MYCIN (Davis, et al., "Production Systems as a Representation for a Knowledge-based Consultation Program", *Artificial Intelligence,* 1977; 8:1:15–45) and its progeny TEIRESIAS, EMYCIN, PUFF, CENTAUR, VM, GUIDON, SACON, ONCOCIN and ROGET. MYCIN is an interactive program that diagnoses certain infectious diseases and prescribes anti-microbial therapy. Such knowledge-based systems contain factual knowledge and rules or other methods for using that knowledge, with all of the information and rules being pre-programmed into the system's memory rather than the system developing its own procedure for reaching the desired result based upon input data, as in neural networks. Another computerized diagnosis method is the Bayesian network, also known as a belief or causal probabilistic network, which classifies patterns based on probability density functions from training patterns and a priori information. Bayesian decision systems are reported for uses in interpretation of mammograms for diagnosing breast cancer (Roberts, et al., "MammoNet: A Bayesian Network diagnosing Breast Cancer", Midwest Artificial Intelligence and Cognitive Science Society Conference, Carbondale, Ill., April 1995) and hypertension (Blinowska, et al. (1993) "Diagnostica—A Bayesian Decision-Aid System—Applied to Hypertension Diagnosis", *IEEE Transactions on Biomedical Engineering* 40:230–35) Bayesian decision systems are somewhat limited in their reliance on linear relationships and in the number of input data points that can be handled, and may not be as well suited for decision-support involving non-linear relationships between variables. Implementation of Bayesian methods using the processing elements of a neural network can overcome some of these limitations (see, e.g., Penny, et al. (1996) In "Neural Networks in Clinical Medicine", *Medical Decision-support,* 1996; 16:4: 386–98). These methods have been used, by mimicking the physician, to diagnose disorders in which important variables are input into the system. It, however, would be of interest to use these systems to improve upon existing diagnostic procedures.

Preterm Delivery and Other Pregnancy-Related Conditions

Determination of impending preterm births and the risk of preterm births is critical for increasing neonatal survival of preterm infants. Many methods for detecting or predicting the risk of preterm birth and/or the risk of impending preterm delivery are subjective, not sufficiently sensitive, and not specific. In particular, preterm neonates account for more than half, and maybe as many as three-quarters of the morbidity and mortality of newborns without congenital anomalies. Although tocolytic agents that delay delivery were introduced 20 to 30 years ago, there has been only a minor decrease in the incidence of preterm delivery. It has been postulated that the failure to observe a larger reduction in the incidence of preterm births is due to errors in the diagnosis of preterm labor and the risk of preterm delivery and because the conditions are too advanced by the time they are recognized for tocolytic agents to successfully delay the birth.

There are a number of biochemical tests for assessing the risk of preterm delivery and other traditional methods of diagnosis based on symptomologies. These methods have false-negative and false-positive error rates. Traditional diagnosis also can require subjective interpretation and may require sophisticated training or equipment. The validity of the diagnosis is related to the experience and ability of the physician. Thus, there is a need for improved methods for assessing risk of preterm delivery, predicting imminent delivery and assessing time of delivery.

Therefore, it is an object herein to provide a non-invasive diagnostic aid for assessing the risk of preterm delivery. It is also an object herein to identify new variables, identify new biochemical tests and markers for preterm delivery and to design to new diagnostic tests that improve upon existing diagnostic methodologies.

SUMMARY OF THE INVENTION

Methods using decision-support systems for the diagnosis of and for aiding in the diagnosis of diseases, disorders and other medical conditions are provided. In particular, methods provided herein, assess the risk of preterm delivery and also the risk of delivery in a selected period of time (delivery-related risks). These methods are useful for assessing these risks in symptomatic pregnant female mammals, particularly human females.

Also provided are methods that use patient history data and identification of important variables to develop a diagnostic test for these assessing these delivery-related risks; a method for identification of important selected variables for use in assessing these delivery-related risks; a method of designing a diagnostic test for assessing; a method of evaluating the usefulness of diagnostic test for these assessments; a method of expanding clinical utility of a diagnostic test to include assessment of these delivery-related risks, and a method of selecting a course of treatment to reduce the risk of delivery within a selected period of time or preterm by predicting the outcome of various possible treatments.

Also provided are disease parameters or variables to aid in predicting pregnancy-related events, such as the likelihood of delivery within a particular time period, and for assessing the risk of preterm delivery.

Also provided are means to use neural network training to guide the development of the tests to improve their sensitivity and specificity, and to select diagnostic tests that improve overall diagnosis of, or potential for, assessment of the risk of preterm delivery or delivery within a selected period of time. A method for evaluating the effectiveness of any given diagnostic test is assessment of the risk of preterm delivery or delivery within a selected period of time is also provided. Also provided herein is a method for identifying variables or sets of variables that aid in the assessment of the risk of preterm delivery or delivery within a selected period of time.

Methods are provided for developing medical diagnostic tests for assessment of the risk of preterm delivery or delivery within a selected period of time using computer-based decision-support systems, such as neural networks and other adaptive processing systems (collectively, "data mining tools"). The neural networks or other such systems are trained on the patient data and observations collected from a group of test patients in whom the condition is known or suspected; a subset or subsets of relevant variables are identified through the use of a decision-support system or systems, such as a neural network or a consensus of neural networks; and another set of decision-support systems is trained on the identified subset(s) to produce a consensus decision-support system based test, such as a neural net-based test for the condition. The use of consensus systems, such as consensus neural networks, minimizes the negative effects of local minima in decision-support systems, such as neural network-based systems, thereby improving the accuracy of the system.

To refine or improve performance, the patient data can be augmented by increasing the number of patients used. Also biochemical test data and other data may be included as part of additional examples or by using the data as additional variables prior to the variable selection process.

The resulting systems are used as an aid in assessment of the risk of preterm delivery or delivery within a selected period of time. In addition, as the systems are used patient data can be stored and then used to further train the systems and to develop systems that are adapted for a particular genetic population. This inputting of additional data into the system may be implemented automatically or done manually. By doing so the systems continually learn and adapt to the particular environment in which they are used. The resulting systems have numerous uses in addition to assessment of the risk of preterm delivery or delivery within a selected period of time, which include predicting the outcome of a selected treatment protocol. The systems may also be used to assess the value of other data in a diagnostic procedure, such as biochemical test data and other such data, and to identify new tests that are useful for assessment of the risk of preterm delivery or delivery within a selected period of time.

The methods are exemplified with reference to neural networks, however, it is understood that other data mining tools, such as expert systems, fuzzy logic, decision trees, and other statistical decision-support systems which are generally non-linear, may be used. Although the variables provided herein are intended to be used with decision-support systems, once the variables are identified, then a person, typically a physician, armed with knowledge the important variables can use them to aid in diagnosis in the absence of a decision-support system or using a less complex linear system of analysis.

In the methods for identifying and selection of important variables and generating systems for diagnosis, patient data or information, typically patient history or clinical data that are the answers to particular queries are collected and variables based on this data are identified. For example, the data includes the answer to a query regarding the number of pregnancies each patient has had. The extracted variable is, thus, number of pregnancies and the query is the how many prior pregnancies (set forth herein as prior pregnancies). The variables are analyzed by the decision-support systems, exemplified by neural networks, to identify important or relevant variables.

A plurality of factors, twelve to about sixteen, particularly a set of fourteen factors, in a specific trained neural network extracted from a collection have been identified as indicia for preterm delivery.

In other embodiments, for example, a method for assessing the risk of delivery prior to completion of 35 weeks of gestation, comprising assessing a subset of variables containing at least three and up to all of the responses to the following queries: Ethnic Origin Caucasian; Marital Status living with partner; EGA by sonogram; EGA at sampling; estimated. date of delivery by best; cervical dilatation (CM); parity-preterm; vaginal bleeding at time of sampling; cervical consistency at time of sampling; and previous pregnancy without complication is provided. The method uses a decision-support system that has been trained to assesses the risk of delivery prior to 35 weeks of gestation.

A method for assessing the risk for delivery in 7 or fewer days, comprising assessing a subset of variables containing at least three up to all of the following variables: Ethnic Origin Caucasian; Uterine contractions with or without pain; Parity-abortions; vaginal bleeding at time of sampling; uterine contractions per hour; and No previous pregnancies is provided. The method uses a decision-support system that has been trained to assesses the risk of delivery within seven days.

A method for assessing the risk for delivery in 14 or fewer days, comprising assessing a subset of variables containing at least three up to all of the following variables: Ethnic Origin Hispanic; Marital Status living with partner; Uterine contractions with or without pain; Cervical dilatation; Uterine contractions per hour; and No previous pregnancies is provided. This method uses a decision-support system that has been trained to assess the risk of delivery within fourteen days.

As shown herein, variables or combinations thereof that heretofore were not known to be important in aiding in assessment of the risk of preterm delivery or delivery within a selected period of time are identified. In addition, patient history data, without supplementing biochemical test data, can be used to diagnose or aid in diagnosing a disorder or condition when used with the decision-support systems, such as the neural nets provided herein.

Also provided herein is a method of identifying and expanding clinical utility of diagnostic test. The results of a particular test, particular one that had heretofore not been considered of clinical utility with respect to assessment of the risk of preterm delivery or delivery within a selected period of time, are combined with the variables and used with the decision-support system, such as a neural net. If the performance, the ability to correctly diagnose a disorder, of the system is improved by addition of the results of the test, then the test will have clinical utility or a new utility is assessing the risk of preterm delivery.

Similarly, the resulting systems can be used to identify new utilities for drugs or therapies and also to identify uses for particular drugs and therapies for reducing the risk of preterm delivery. For example, the systems can be used to select subpopulations of patients for whom a particular drug or therapy is effective. Thus, methods for expanding the indication for a drug or therapy and identifying new drugs and therapies are provided. Diagnostic software and exemplary neural networks that use the variables for assessment of the risk of delivery before a specified time are also provided.

In other embodiments, the performance of a diagnostic neural network system for assessing risk of preterm delivery is enhanced by including variables based on biochemical test results from a relevant biochemical test as part of the factors (herein termed biochemical test data) used for training the network. One of exemplary networks described herein that results therefrom is an augmented neural network that employs 6 input factors, including results of a biochemical test and the 7 clinical parameters. The set of weights of the augmented neural networks differ from the set of weights of the clinical data neural networks. The exemplified biochemical test employs an immuno-diagnostic test format, such as the ELISA diagnostic test format. Neural networks, thus, can be trained to predict the disease state based on the identification of factors important in predicting the disease state and combining them with biochemical data.

The resulting diagnostic systems may be adapted and used not only for diagnosing the presence of a condition or disorder, but also the severity of the disorder and as an aid in selecting a course of treatment.

BRIEF DESCRIPTION OF THE DRAWINGS

FIG. 8 depicts an exemplary Edit Record dialog box in preterm delivery software;

FIG. 9 depicts an exemplary Go To dialog box in the software;

FIG. 10 depicts an exemplary Help About dialog box in the software;

FIGS. 11A and 11B shows exemplary outputs from the software, FIG. 11B includes the input data as well;

DETAILED DESCRIPTION OF PREFERRED EMBODIMENTS

Definitions

Figure 1:
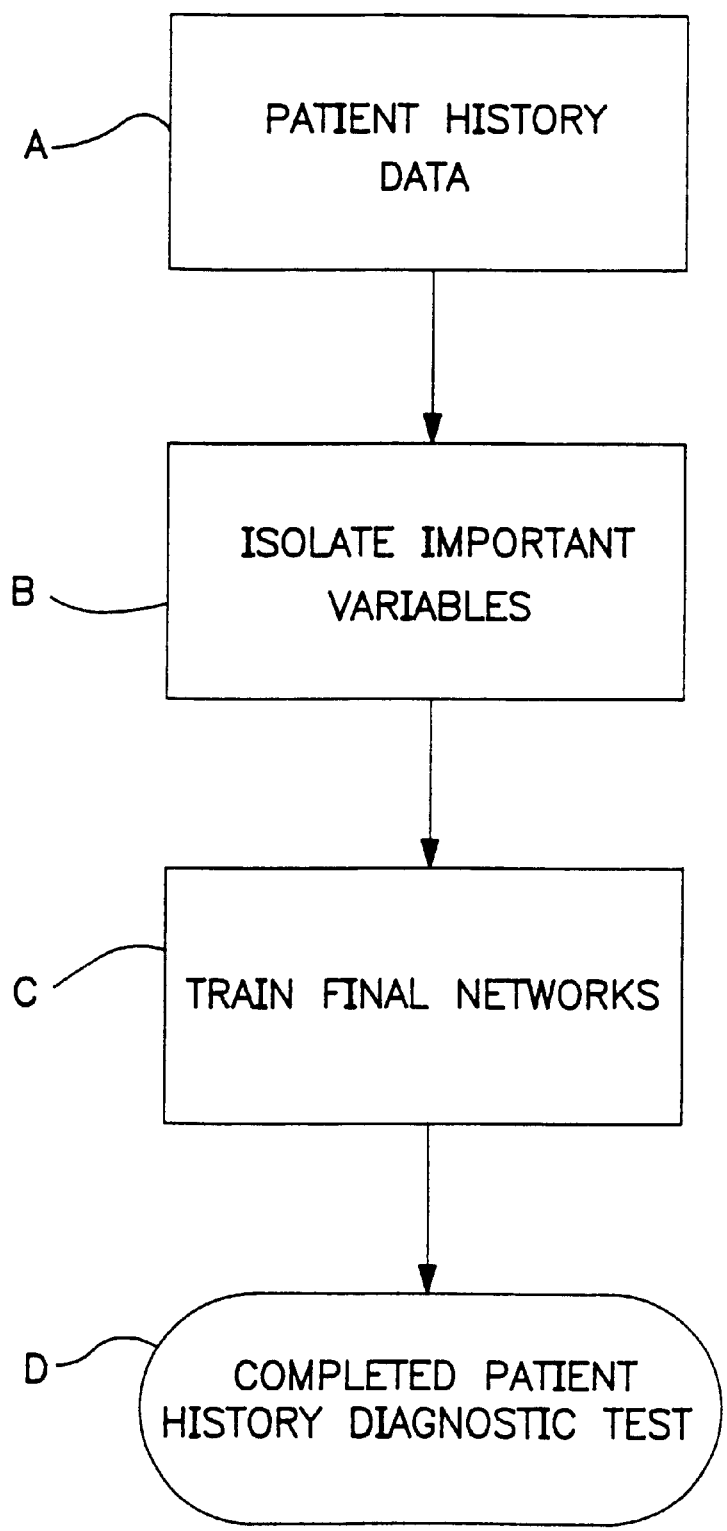
FIG. 1 is a flow chart for developing a patient-history-based diagnostic test process.

Unless defined otherwise, all technical and scientific terms used herein have the same meaning as is commonly understood by one of skill in the art to which this invention belongs. All patents, applications and publications referred to herein are incorporated by reference.

As used herein, a decision-support system, also referred to as a "data mining system" or a "knowledge discovery in data system", is any system, typically a computer-based system, that can be trained on data to classify the input data and then subsequently used with new input data to make decisions based on the training data. These systems include, but are not limited, expert systems, fuzzy logic, non-linear regression analysis, multivariate analysis, decision tree classifiers, Bayesian belief networks and, as exemplified herein, neural networks.

As used herein, an adaptive machine learning process refers to any system whereby data are used to generate a predictive solution. Such processes include those effected by expert systems, neural networks, and fuzzy logic.

As used herein, expert system is a computer-based problem solving and decision-support system based on knowledge of its task and logical rules or procedures for using the knowledge. Both the knowledge and the logic are entered into the computer from the experience of human specialists in the area of expertise.

As used herein, a neural network, or neural net, is a parallel computational model comprised of densely interconnected adaptive processing elements. In the neural network, the processing elements are configured into an input layer, an output layer and at least one hidden layer. Suitable neural networks are known to those of skill in this art (see, e.g., U.S. Pat. Nos. 5,251,626; 5,473,537; and 5,331,550, Baxt (1991) "Use of an Artificial Neural Network for the Diagnosis of Myocardial Infarction," *Annals of Internal Medicine* 115:843; Baxt (1992) "Improving the Accuracy of an Artificial Neural Network Using Multiple Differently Trained Networks," *Neural Computation* 4:772; Baxt (1992) "Analysis of the clinical variables that drive decision in an artificial neural network trained to identify the presence of myocardial infarction," *Annals of Emergency Medicine* 21:1439; and Baxt (1994) "Complexity, chaos and human physiology: the justification for non-linear neural computational analysis," *Cancer Letters* 77:85).

As used herein, a processing element, which may also be known as a perceptron or an artificial neuron, is a computational unit which maps input data from a plurality of inputs into a single binary output in accordance with a transfer function. Each processing element has an input weight corresponding to each input which is multiplied with the signal received at that input to produce a weighted input value. The processing element sums the weighted inputs values of each of the inputs to generate a weighted sum which is then compared to the threshold defined by the transfer function.

As used herein, transfer function, also known as a threshold function or an activation function, is a mathematical function which creates a curve defining two distinct categories. Transfer functions may be linear, but, as used in neural networks, are more typically non-linear, including quadratic, polynomial, or sigmoid functions.

As used herein, backpropogation, also known as backprop, is a training method for neural networks for correcting errors between the target output and the actual output. The error signal is fed back through the processing layer of the neural network, causing changes in the weights of the processing elements to bring the actual output closer to the target output.

As used herein, Quickprop is a backpropogation method that was proposed, developed and reported by Fahlman ("Fast Learning Variations on Back-Propagation: An Empirical Study", *Proceedings on the* 1988 *Connectionist Models Summer School*, Pittsburgh, 1988, D. Touretzky, et al, eds., pp.38–51, Morgan Kaufmann, San Mateo, Calif.; and, with Lebriere, "The Cascade-Correlation Learning Architecture", *Advances in Neural Information Processing Systems* 2,(Denver, 1989), D. Touretzky, ed., pp. 524–32. Morgan Kaufmann, San Mateo, Calif.).

As used herein, diagnosis refers to a predictive process in which the presence, absence, severity or course of treatment of a disease, disorder or other medical condition is assessed. For purposes herein, diagnosis will also include predictive processes for determining the outcome resulting from a treatment.

As used herein, a patient or subject includes any mammals for whom diagnosis is contemplated. Humans are the preferred subjects.

As used herein, biochemical test data refers to the results of any analytical methods, which include, but are not limited to:, immunoassays, bioassays, chromatography, data from monitors, and imagers; measurements and also includes data related to vital signs and body function, such as pulse rate, temperature, blood pressure, the results of, for example, EKG, ECG and EEG, biorhythm monitors and other such information. The analysis can assess for example, analytes, serum markers, antibodies, and other such material obtained from the patient through a sample.

As used herein, patient historical data refers to data obtained from a patient, such as by questionnaire format, but typically does not include biochemical test data as used herein, except to the extent such data is historical, a desired solution is one that generates a number or result whereby a diagnosis of a disorder can be generated.

As used herein, wherein a training example includes the observation data for a single diagnosis, typically the observation data related to one patient.

As used herein, the parameters identified from patient historical data are herein termed observation factors or values or variables. For example, patient data will include information with respect to individual patient's smoking habits. The variable associated with that will be smoking.

As used herein, partition means to select a portion of the data, such as 80%, and use it for training a neural net and to use the remaining portion as test data. Thus, the network is trained on all but one portion of the data. The process can then be repeated and a second network trained. The process is repeated until all partitions are used as used as test data and training data.

As used herein, the method of training by partitioning the available data into a plurality of subsets is generally referred to as the "holdout method" of training. The holdout method is particularly useful when the data available for network training is limited.

As used herein, training refers to the process in which input data are used to generate a decision-support system. In particularly, with reference to neural nets, training is a trial-and-error process involving a series of iterative adjustments to the processing element weights so that a particular processing element provides an output which, when combined with the outputs of other processing elements, generates a result which minimizes the resulting error between the outputs of the neural network and the desired outputs as represented in the training data.

As used herein, a variable selection process is a systematic method whereby combinations of variables that yield predictive results are selected from any available set. Selection is effected by maximizing predictive performance of subsets such that addition of additional variables does not improve the result. The preferred methods provided herein advantageously permit selection of variables without considering all possible combinations.

As used herein, a candidate variable is a selected item from collected observations from a group of test patients for the diagnostic embodiments or other records, such as financial records, that can be used with the decision-support system. Candidate variables will be obtained by collecting data, such as patient data, and categorizing the observations as a set of variables.

As used herein, important selected variables refer to variables that enhance the network performance of the task at hand. Inclusion of all available variables does not result in the optimal neural network; some variables, when included in network training, lower the network performance. Networks that are trained only with relevant parameters result in increased network performance. These variables are also referred to herein as a subset of relevant variables.

As used herein, ranking refers to a process in which variables are listed in an order for selection. Ranking may be arbitrary or, preferably, is ordered. Ordering may be effected, for example, by a statistical analysis that ranks the variables in order of importance with respect to the task, such as diagnosis, or by a decision-support system based analysis. Ranking may also be effected, for example, by human experts, by rule based systems, or any combination of any of these methods.

As used herein, a consensus of neural networks refers to the linear combination of outputs from a plurality of neural networks where the weight on each is outputs is determined arbitrarily or set to an equal value.

As used herein, a greedy algorithm is a method for optimizing a data set by determining whether to include or exclude a point from a given data set. The set begins with no elements and sequentially selects an element from the feasible set of remaining elements by myopic optimization, in which, given any partial solution, another value that improves the object the most is selected.

As used herein, a genetic algorithm is a method that begins with an initial population of randomly generated neural networks which are run through a training cycle and ranked according to their performance in reaching the desired target. The poor-performing networks are removed from the population, with the fitter networks being retained and selected for the crossover process to offspring that retain the desirable characteristics of the parent networks.

As used herein, performance of a system is said to be improved or higher when the results more accurately predict or determine a particular outcome. It is also to be understood that the performance of a system will typically be better as more training examples are used. Thus, the systems herein will improve over time as they are used and more patient data is accumulated and then added to the systems as training data.

As used herein, sensitivity=TP/(TP+FN); specificity is TN/(TN+FP), where TP=true positives; TN=true negatives; FP=false positives; and FN=false negative. Clinical sensitivity measures how well a test detects patients with the disease; clinical specificity measures how well a test correctly identifies those patients who do not have the disease.

As used herein, positive predictive value (PPV) is TP/(TP+FP); and negative predictive value (NPV) is TN/(TN+FN). Positive predictive value is the likelihood that a patient with a positive test actually has the disease, and negative predictive value is the likelihood that a patient with a negative test result does not have the disease.

As used herein, fuzzy logic is an approach to deal with systems that cannot be described precisely. Membership functions (membership in a data set) are not binary in fuzzy logic systems; instead membership function may take on fractional values. Therefore, an element can be simultaneously contained in two contradictory sets, albeit with different coefficients of set membership. Thus, this type of approach is useful for answering questions in which there is no yes or answer. Thus, this type of logic is suitable for categorizing responses from patient historical questionnaires, in which the answer is often one of degree.

As used herein, term refers to delivery at about 40 weeks. Preterm delivery refers to delivery prior to that time and, particularly prior to completed fetal development. The critical time period with respect to the risk of preterm delivery is typically anytime on or before 37 weeks because fetal lung development may not be completed. Typically lung maturation to permit the infant to breathe on its own is complete between about 34 and 37 weeks delivery. Thus, the focus of risk assessment is risk of delivery before 37 weeks and more particularly before 35 weeks. The earlier the risk of preterm delivery can be assessed, the better the opportunity for the clinician to provide appropriate care and intervention, where available and possible.

The methods herein are designed to be used at any time during pregnancy. The minimum parameters include, for example, those listed in FIG. 8 or 11B.

As used herein, the assessment of the risk of preterm delivery and also the risk of delivery in a selected period of time are referred to as "delivery-related risks."

As used herein, risk of delivery within a selected period of time refers either to prediction of endpoint, i.e., whether a woman will deliver on or before a particular gestational; or regardless of the present gestational age, the risk of delivery within a given time interval, such as within 7 days or less, within 14 days or less or any selected interval.

1. General Considerations and General Methodology

The general methodology relied upon in developing the decision support systems provided herein is described in described in co-owned applications U.S. application Ser. No. 08/798,306 and published International PCT application No. WO 97/29447.

It has been determined that a number of techniques can be used to train neural networks for analyzing observation values such as patient history and/or biochemical information. Depending upon the characteristics of the available data and the problem to be analyzed, different neural network training techniques can be used. For example, where large amounts of training inputs are available, methodology may be adopted to eliminate redundant training information.

Neural networks may also reveal that certain input factors that were not initially considered to be important can influence an outcome, as well as reveal that presumably important factors are not outcome determinative. The ability of neural networks to reveal the relevant and irrelevant input factors permit their use in guiding the design of a diagnostic test. As shown herein, neural networks, and other such data mining tools, are a valuable advance in diagnostics, providing an opportunity to increase the sensitivity and specificity of a diagnostic test. As shown herein, care must be taken to avoid the potential of poor-accuracy answer due to the phenomenon of local minima. The methods herein provide a means to avoid this problem or at least minimize it.

In developing the developing diagnostic procedures, and in particular diagnostic tests that are based solely or in part on patient information, a number of problems have been solved. For example, there is generally a limited amount of data because there is a limited number of patients where training data are available. To solve this, as described below, the patient information is partitioned when training the network. Also, there is generally a large number of input observation factors available for use in connection with the available data, so methods for ranking and selecting observations were developed.

Also, there are generally large number of binary (true/false) input factors in the available patient data, but these factors are generally sparse in nature (values that are positive or negative in only a small percentage of cases of the binary input factors in the available patient data). Also there is a high degree of overlap between the positive and negative factors of the condition being diagnosed.

These characteristics and others impact the choice of procedures and methods used to develop a diagnostic test. These problems are addressed and solved herein.

As shown in U.S. application Ser. No. 08/798,306 and published International PCT application No. WO 97/29447, computer-based decision-support systems such as neural networks reveal that certain input factors, which were not initially considered to be important, can influence an outcome. This ability of a neural network to reveal the relevant input factors permits its use in guiding the design of diagnostic tests. Thus a method of designing a diagnostic test, and a method of evaluating utility of diagnostic test are also provided. In each instance, the data from the test or possible test is added to the input of the decision-support system. If the results are improved when the data are included in the input, then the diagnostic test may have clinical utility. In this manner, tests that heretofore were not known to be of value in diagnosis of a particular disorder are identified, or new tests can be developed. Neural networks can add robustness to diagnostic tests by discounting the effects of spurious data points and by identifying other data points that might be substituted, if any.

Networks are trained on one set of variables and then clinical data from diagnostic or biochemical test data and/or additional patient information are added to the input data. Any variable that improves the results compared to their absence is (are) selected. As a result, particular tests that heretofore were of unknown value in diagnosing a particular disorder can be shown to have relevance. For example, the presence or absence of particular spots on a western blot of serum antibodies can be correlated with a disease state. Based on the identity of particular spots (i.e., antigens) new diagnostic tests can be developed.

An example of the application of the prediction technology to aid in the diagnosis of disease and more particularly the use of neural network techniques with inputs from various information sources to aid in the prediction of time of delivery and assessment of the risk of preterm delivery is provided. A trained set of neural networks operative according to a consensus of networks in a computer system is employed to evaluate specific clinical associations, for example obtained by survey, some of which may not generally be associated with a disease condition. Exemplary neural networks are provided and factors used to aid in the assessment are provided. The neural network training is based on correlations between answers to questions furnished by physicians of a significant number of clinical patients whose condition was verified.

2. Development of Patient History Diagnostic Test Diagnostic Tests

Methods for diagnosis based solely on patient history data are provided. As demonstrated herein, it is possible to provide decision-support system that rely only on patient history information but that aid in diagnosis. Consequently, the resulting systems can then be used to improve the predictive ability of biochemical test data, to identify new disease markers, to develop biochemical tests, to identify tests that heretofore were not thought to be predictive of a particular disorder.

The methods may also be used to select an appropriate course of treatment by predicting the result of selected course of treatment and to predict status following therapy. The input variables for training would be derived from, for example, electronic patient records, that indicate diagnoses and other available data, including selected treatments and outcomes. The resulting decision-support system would then be used with all available data to, for example, categorize women into different classes that will respond to different treatments and predict the outcome of a particular treatment. This permits selection of a treatment or protocol most likely to be successful.

Similarly, the systems can be used to identify new utilities for drugs or therapies and also to identify uses for particular drugs and therapies. For example, the systems can be used to select subpopulations of patients for whom a particular drug or therapy is effective. Thus, methods for expanding the indication for a drug or therapy and identifying new drugs and therapies are provided.

Collection of Patient Data, Generation of Variables and Overview

To exemplify the methods herein, FIG. 1 sets forth a flow chart for developing a patient-history-based diagnostic test process. The process begins with collection of patient history data (Step A). Patient history data or observation values are obtained from patient questionnaires, clinical results, in some instances diagnostic test results, and patient medical records and supplied in computer-readable form to a system operating on a computer. In the digital computer, the patient history data are categorized into a set of variables of two forms: binary (such as true/false) values and quantitative (continuous) values. A binary-valued variable might include the answer to the question, "Do you smoke?" A quantitative-valued variable might be the answer to the question, "How many packs per day do you smoke?" Other values, such as membership functions, may also be useful as input vehicles.

The patient history data will also include a target or desired outcome variable that would be assumed to be indicative of the presence, absence, or severity of the medical condition to be diagnosed. This desired outcome information is useful for neural network training. The selection of data to be included in the training data can be made with the knowledge or assumption of the presence, severity, or absence of the medical condition to be diagnosed. As noted herein, diagnosis may also include assessment of the progress and/or effectiveness of a therapeutic treatment.

The number of variables, which can be defined and thus generated, can be unwieldy. Binary variables are typically sparse in that the number of positive (or negative) responses is often a small percentage of the overall number of responses. Thus, in instances in which there is a large number of variables and a small number of patient cases available in a typical training data environment, steps are taken to isolate from the available variables a subset of variables important to the diagnosis (Step B). The specific choice of the subset of variables from among the available variables will affect the diagnostic performance of the neural network.

The process outlined herein has been found to produce a subset of variables which is comparable or superior in sensitivity and reliability to the subset of variables typically chosen by a trained human expert, such as a physician. In some instances, the variables are prioritized or placed in order of rank or relevance.

Thereafter, the final neural networks to be used in the diagnostic procedure are trained (Step C). In preferred embodiments, a consensus (i.e. a plurality) of networks are trained. The resulting networks form the decision-support functionality for the completed patient history diagnostic test (Step D).

Method for Isolation of Important Variables

A method for isolation of important variables is provided herein. The method permits sets of effective variables to be selected without comparing every possible combination of variables. The important variables may be used as the inputs for the decision-support systems.

Isolation of Important or Relevant Variables—Ranking the Variables

FIG. 3 provides a flow chart of the process for isolating the important or relevant variables (Step E) within a diagnostic test. Such a process is typically conducted using a digital computer system to which potentially relevant information has been provided. This procedure ranks the variables in order of importance using two independent methods, then selects a subset of the available variables from the uppermost of the ranking. As noted above, other ranking methods can be used by those of skill in the art in place of chi square or sensitivity analysis. Also, if x is set to N (the total number of candidate variables), then ranking can be arbitrary.

The system trains a plurality of neural networks on the available data (Step I), as explained hereinafter, then generates a sensitivity analysis over all trained networks to determine to what extent each input variable was used in the network to perform the diagnosis (Step J). A consensus sensitivity analysis of each input variable is determined by averaging the individual sensitivity analysis results for each of the networks trained. Based upon sensitivity, a ranking order for each of the variables available from the patient history information is determined (Step K).

Ranking the Variables

In preferred embodiments, the variables are ranked using a statistical analysis, such as a chi square analysis, and/or a decision-support system-based analysis, such as a sensitivity analysis. A sensitivity analysis and chi square analysis are used, in the exemplary embodiment to rank variables. Other statistical methods and/or decision-support system-based, including but not limited to regression analysis, discriminant analysis and other methods known to those of skill in the art, may be used. The ranked variables may be used to train the networks, or, preferably, used in the method of variable selection provided herein.

The method employs a sensitivity analysis in which each input is varied and the corresponding change in output is measured (see, also, Modai, et al., (1993) "Clinical Decisions for Psychiatric Inpatients and Their Evaluation by Trained Neural Networks", *Methods of Information in Medicine* 32:396–99; Wilding et al. (1994) "Application of Backpropogation Neural Networks to Diagnosis of Breast and Ovarian Cancer", *Cancer Letters* 77:145–53; Ruck et al. (1990) "Feature Selection in Feed-Forward Neural Networks", *Neural Network Computing* 20:40–48; and Utans, et al. (1993) "Selecting Neural Network Architectures Via the Prediction Risk: Application to Corporate Bond Rating Prediction";

Proceedings of the First International Conference on Artificial Intelligence Applications on Wall Street. Washington, D.C., IEEE Computer Society Press. pp. 35–41; Penny et al. (1996) In "Neural Networks in Clinical Medicine", *Medical Decision-support* 4:386–398). Such methods, which have heretofore not been used to select important variables, as described herein. For example, sensitivity analysis has bee reported to be used to develop a statistical approach to determine the relationships between the variables, but not for selection of important variables (see, Baxt et al. (1995) "Bootstrapping Confidence Intervals for Clinical Input Variable Effects in a Network Trained to Identify the Presence of Myocardial Infarction," *Neural Computation* 7: 624–38). Any such sensitivity analyses may be used as described herein as part of the selection of important variables as an aid to diagnosis.

In a particular embodiment, the sensitivity analysis involves: (k) determining an average observation value for each of the variables in an observation data set; (l) selecting a training example, and running the example through a decision-support system to produce an output value, designated and stored as the normal output; (m) selecting a first variable in the selected training example, replacing the observation value with the average observation value of the first variable; running the modified example in the decision-support system in the forward mode and recording the output as the modified output; (n) squaring the difference between the normal output and the modified output and accumulating it as a total for each variable, in which this total is designed the selected variable total for each variable; (o) repeat steps (m) and (n) for each variable in the example; (p) repeating steps (l)–(n) for each example in the data set, where each total for the selected variable represents the relative contribution of each variable to the determination of the decision-support system output. This total will be used to rank each variable according to its relative contribution to the determination of the decision-support system output.

Step K, FIG. 3, provides an outline of the sensitivity analysis. Each network or a plurality of trained neural networks (networks $N_1$ through $N_n$) is run in the forward mode (no training) for each training example $S_x$ (input data group for which true output is known or suspected; there must be at least two training examples), where "x" is the number of training examples. The output of each network $N_1$–$N_n$ for each training example $S_x$ is recorded, i.e., stored in memory. A new training example is defined containing the average value for each input variable within all training examples. One at a time, each input variable within each original training example $S_x$ is replaced with its corresponding average value $V_{1(avg)}$ through $V_{y(avg)}$, where "y" is the number of variables, and the modified training example $S_x'$ is again executed through the multiple networks to produce a modified output for each network for each variable. The differences between the output from the original training example $S_x$ and the modified output for each input variable are the squared and summed (accumulated) to obtain individual sums corresponding to each input variable. To provide an illustration, for example, for 10 separate neural networks $N_1$–$N_{10}$ and 5 different training examples $S_1$–$S_5$, each having 15 variables $V_1$–$V_{15}$, each of the 5 training examples would be run through the 10 networks to produce 50 total outputs. Taking variable $V_1$ from each of the training examples, an average value $V_{1(avg)}$ is calculated. This averaged variable $V_{1(avg)}$ is substituted into each of the 5 training examples to create modified training examples $S_1'$–$S_5'$ and they are again run through the 10 networks. Fifty modified output values are generated by the networks $N_1$–$N_{10}$ for the 5 training examples, the modification being the result of using the average value variable $V_{1(avg)}$. The difference between each of the fifty original and modified output values is calculated, i.e., the original output from training $S_4$ in network $N_6$: $OUT(S_4N_6)$ is subtracted from the modified output from training example $S_4$ in network $N_6$, $OUT(S_4'N_6)$. That difference value is squared $[OUT(S_4'N_6) – OUT(S_4N_6)]^2_{V_1}$. This value is summed with the squared difference values for all combinations of networks and training examples for the iteration in which variable $V_1$ was substituted with its average value $V_{1(avg)}$, i.e., $$\sum_{x=1}^{5} \sum_{n=1}^{10} [OUT(S_x'N_n) - OUT(S_xN_n)]^2_{V_1}.$$

Next, the process is repeated for variable #2, finding the differences between the original and modified outputs for each combination of network and training example, squaring, then summing the differences. This process is repeated for each variable until all 15 variables have been completed.

Each of the resultant sums is then normalized so that if all variables contributed equally to the single resultant output, the normalized value would be 1.0. Following the preceding example, the summed squared differences for each variable are summed to obtain a total summed squared difference for all variables. The value for each variable is divided by the total summed square difference to normalize the contribution from each variable. From this information, the normalized value for each variable can be ranked in order of importance, with higher relative numbers indicating that the corresponding variable has a greater influence on the output. The sensitivity analysis of the input variables is used to indicate which variables played the greatest roles in generating the network output.

It has been found herein that using consensus networks to perform sensitivity analysis improves the variable selection process. For example, if two variables are highly correlated, a single neural network trained on the data might use only one of the two variables to produce the diagnosis. Since the variables are highly correlated, little is gained by including both, and the choice of which to include is dependent on the initial starting conditions of the network being trained. Sensitivity analysis using a single network might show that only one, or the other, is important. Sensitivity analysis derived from a consensus of multiple networks, each trained using different initial conditions, may reveal that both of the highly correlated variables are important. By averaging the sensitivity analysis over a set of neural networks, a consensus is formed that minimizes the effects of the initial conditions.

Chi-Square Contingency Table

When dealing with sparse binary data, a positive response on a given variable might be highly correlated to the condition being diagnosed, but occur so infrequently in the training data that the importance of the variable, as indicated by the neural network sensitivity analysis, might be very low. In order to catch these occurrences, the Chi-square contingency table is used as a secondary ranking process. A 2×2 contingency table Chi-square test on the binary variables, where each cell of the table is the observed frequency for the combination of the two variables (FIG. 3, Step F) is performed. A 2×2 contingency table Chi-square test is performed on the continuous variables using optimal thresholds (which might be empirically-determined) (Step G). The binary and continuous variables that have been based on Chi-square analysis are ranked (Step H).

The standard Chi-square 2×2 contingency table operative on the binary variables (Step F) is used to determine the significance of the relationship between a specific binary input variable and the desired output (as determined by comparing the training data with the known single output result). Variables that have a low Chi-square value are typically unrelated to the desired output.

For variables that have continuous values, a 2×2 contingency table can be constructed (Step G) by comparing the continuous variable to a threshold value. The threshold value is modified experimentally to yield the highest possible Chi-square value.

The Chi-square values of the continuous variables and of the binary variables can then be combined for common ranking (Step H). A second level of ranking can then be performed that combines the Chi-square-ranked variables with the sensitivity-analysis-ranked variables (Step L). This combining of rankings allows variables that are significantly related to the output but that are sparse (i.e, values that are positive or negative in only a small percentage of cases) to be included in the set of important variables. Otherwise, important information in such a non-linear system could easily be overlooked.

Selection of Important Variables From Among the Ranked Variables

As noted above, important variables are selected from among the identified variables. Preferably the selection is effected after ranking the variables at which time a second level ranking process is invoked. A method for identification of important variables (parameters) or sets thereof for use in the decision-support systems is also provided. This method, while exemplified herein with reference to medical diagnosis, has broad applicability in any field, such as financial analysis and other endeavors that involve statistically-based prediction, in which important parameters or variables are selected from among a plurality.

In particular, a method for selecting effective combinations of variables is provided. After (1) providing a set of "n" candidate variables and a set of "selected important variables", which initially is empty; and (2) ranking all candidate variables based on a chi square and sensitivity analysis, as described above, the method involves: (3) taking the highest "m" ranked variables one at a time, where m is from 1 up to n, and evaluating each by training a consensus of neural nets on that variable combined with the current set of important variables; (4) selecting the best of the m variables, where the best variable is the one that most improves performance, and if it improves performance, adding it to the "selected important variable" set, removing it from the candidate set and continuing processing at step (3) otherwise continuing by going to step (5); (5) if all variables on the candidate set have been evaluated, the process is complete, otherwise continue taking the next highest "m" ranked variables one at a time, and evaluating each by training a consensus of neural nets on that variable combined with the current set of important selected variables and performing step (4).

In particular, the second level ranking process (Step L) starts by adding the highest ranked variable from the sensitivity analysis (Step K) to the set of important variables (Step H). Alternatively, the second level ranking process could be started with an empty set and then testing the top several (x) variables from each of the two sets of ranking. This second level ranking process uses the network training procedure (Step l) on a currently selected partition or subset of variables from the available data to train a set of neural networks. The ranking process is a network training procedure using the current set of "important" variables (which generally will initially be empty) plus the current variable being ranked or tested for ranking, and uses a greedy algorithm to optimize the set of input variables by myopically optimizing the input set based upon the previously identified important variable(s), to identify the remaining variable(s) which improve the output the most.

Figure 4:
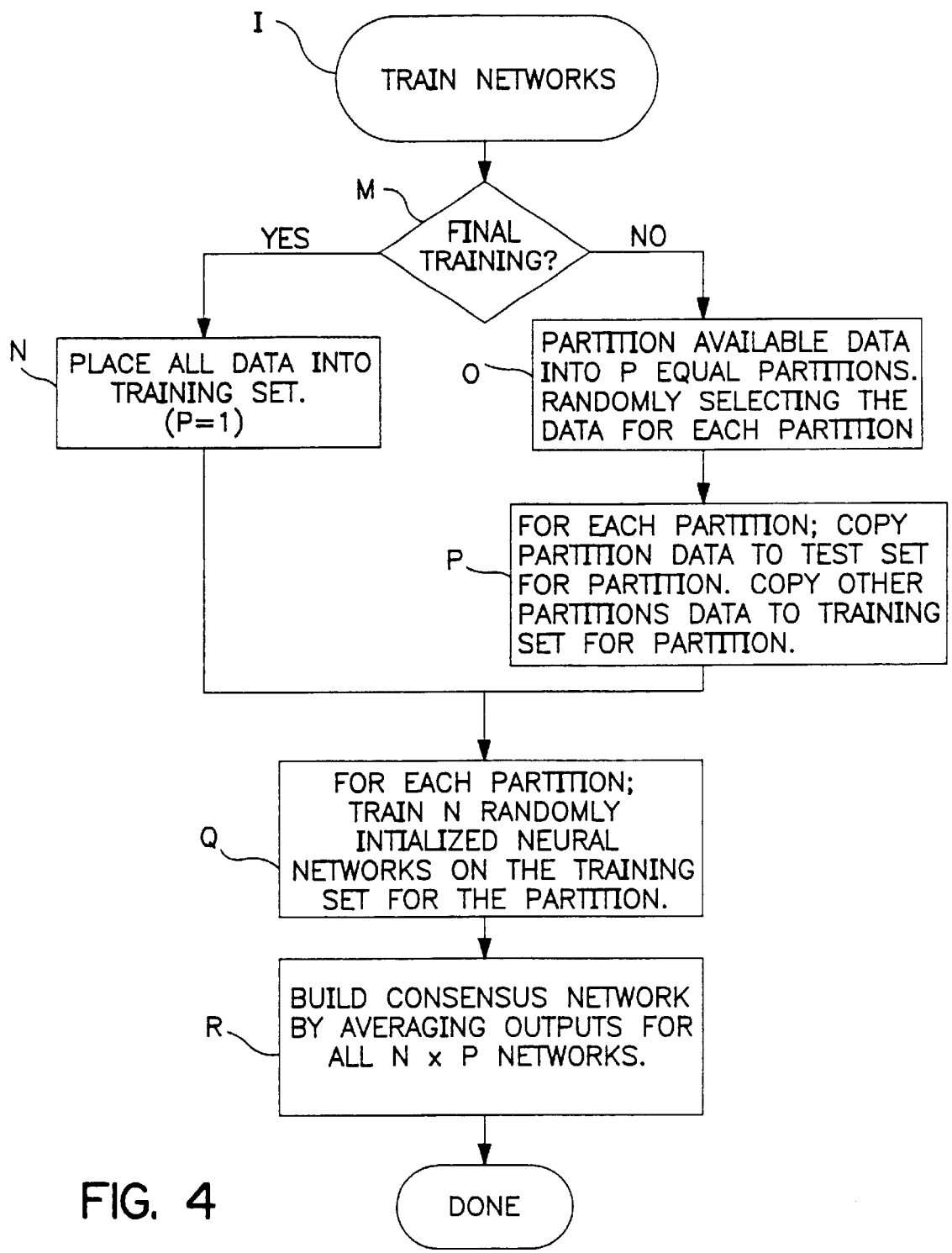
FIG. 4 is a flow chart on the process of training one or a set of neural networks involving a partitioning of variables.

This training process is illustrated in FIG. 4. The number of inputs used by the neural network is controlled by excluding inputs which are found to not contribute significantly to the desired output, i.e., the known target output of the training data. A commercial computer program, such as ThinksPro™ neural networks for Windows™ (or TrainDos™ the DOS version) by Logical Designs Consulting, Inc, La Jolla, Calif., or any other such program that one of skill in the art can develop may be used to vary the inputs and train the networks.

A number of other commercially available neural network computer programs may be used to perform any of the above operations, including Brainmakert™, which is available from California Scientific Software Co., Nevada Adaptive Solutions, Beaverton, Oreg.; Neural Network Utility/2™, from NeuralWare, Inc., Pittsburgh, Pa.; NeuroShell™ and Neuro-Windows™, from Ward Systems Group, Inc., Frederick, Md. Other types of data mining tools, i.e., decision-support systems, that will provide the function of variable selection and network optimization may be designed or other commercially available systems may be used. For example, NeuroGenetic Optimizer™ from BioComp Systems, Inc., Redmond, Wash.; and Neuro Forecaster/GENETICA, from New Wave Intelligent Business Systems (NIB5) Pte Ltd., Republic of Singapore, use genetic algorithms that are modelled on natural selection to eliminate poor-performing nodes within network population while passing on the best performing rates to offspring nodes to "grow" an optimized network and to eliminate input variables which do not contribute significantly to the outcome. Networks based on genetic algorithms use mutation to avoid trapping in local minima and use crossover processes to introduce new structures into the population.

Knowledge discovery in data (KDD) is another data mining tool, decision-support system, designed to identify significant relationship is that exist among variables, and are useful when there are many possible relationships. A number of KDD systems are commercially available including Darwin™, from Thinking Machines, Bedford, Mass.; Mineset™, from Silicon Graphics, Mountain View, Calif., and Eikoplex™ from Ultragem Data Mining Company, San Francisco, Calif. (Eikoplex™ has been used to provide classification rules for determining the probability of the presence of heart disease.) Others may be developed by those of skill in the art.

Proceeding with the ranking procedure, if, for example, x is set to 2, then the top two variables from each of the two ranking sets will be tested by the process (FIG. 3, Steps L, S), and results are checked to see if the test results show improvement (Step T). If there is an improvement, the single best performing variable is added to the set of "important" variables, and then that variable is removed from the two rankings (FIG. 3, Step U) for further testing (Step S). If there is no improvement, then the process is repeated with the next x variables from each set until an improvement is found or all of the variables from the two sets have been tested. This process is repeated until either the source sets are empty, i.e., all relevant or important variables have been included in the final network, or all of the remaining variables in the sets being tested are found to be below the performance of the current list of important variables. This process of elimination greatly reduces the number of subsets of the available variables which must be tested in order to determine the set of important variables. Even in the worst case, with ten available variables, the process would test only. 34 subsets where x=2 and only 19 subsets of the 1024 possible combinations if x=1. Thus, where there are 100 available variables, only 394 subsets would be tested where x=2. The variables from the network with the best test performance are thus identified for use (FIG. 3, Step V).

Then the final set of networks is trained to perform the diagnosis (FIG. 4, Steps M, N, Q, R). Typically, a number of final neural networks are trained to perform the diagnosis. It is this set of neural networks (a that can form the basis of a deliverable product to the end user. Since different initial conditions (initial weights) can produce differing outputs for a given network, it is useful to seek a consensus. (The different initial weights are used to avoid error from trapping in local minima.) The consensus is formed by averaging the outputs of each of the trained networks which then becomes the single output of the diagnostic test.

Training a Consensus of Networks

FIG. 4 illustrates the procedure for the training of a consensus of neural networks. It is first determined whether the current training cycle is the final training step (Step M). If yes, then all available data are placed into the training data set (i.e., P=1) (Step N). If no, then the available data are divided into P equal-sized partitions, randomly selecting the data for each partition (Step O). In an exemplary embodiment, for example five partitions, eq., $P_1$–$P_5$, are created from the full set of available training data. Then two constructions are undertaken (Step P). First, one or more of the partitions are copied to a test file and the remaining partitions are copied to a training file. Continuing the exemplary embodiment of five partitions, one of the partitions, e.g., $P_1$,, representing 20% of the total data set, is copied to the test file. The remaining four files, $P_2$–$P_4$, are identified as training data. A group of N neural networks is trained using the training partitions, each network having different starting weights (Step Q). Thus, in the exemplary embodiment, there will be 20 networks (N=20) with starting weights selected randomly using 20 different random number seeds. Following completion of training for each of the 20 networks, the output values of all 20 networks are averaged to provide the average performance on the test data for the trained networks. The data in the test file (partition $P_1$) is then run through the trained networks to provide an estimate of the performance of the trained networks. The performance is typically determined as the mean squared error of prediction, or misclassification rate. A final performance estimate is generated by averaging the individual performance estimates of each network to produce a completed consensus network (Step R). This method of training by partitioning the available data into a plurality of subsets is generally referred to as the "holdout method" of training.

The holdout method is particularly useful when the data available for network training is limited.

Test set performance can be empirically maximized by performing various experiments that identify network parameters that maximize test set performance. The parameters that can be modified in this set of experiments are 1) the number of hidden processing elements, 2) the amount of noise added to the inputs, 3) the amount of error tolerance, 4) the choice of learning algorithm, 5) the amount of weights decay, and 6) the number of variables. A complete search of all possible combinations is typically not practical, due to the amount of processing time that is required. Accordingly, test networks are trained with training parameters chosen empirically via a computer program, such as ThinksPro™ or a user developed program, or from the results of existing test results generated by others who are working in the field of interest. Once a "best" configuration is determined, a final set of networks can be trained on the complete data set.

3. Development of Biochemical Diagnostic Test

A similar technique for isolating variables may be used to build or validate a biochemical diagnostic test, and also to combine a biochemical diagnostic test data with the patient history diagnostic test to enhance the reliability of a medical diagnosis.

The selected biochemical test can include any test from which useful diagnostic information may be obtained in association with a patient and/or patient's condition. The test can be instrument or non-instrument based and can include the analysis of a biological specimen, a patient symptom, a patient indication, a patient status, and/or any change in these factors. Any of a number of analytical methods can be employed and can include, but are not limited to, immunoassays, bioassays, chromatography, monitors, and imagers. The analysis can assess analytes, serum markers, antibodies, and the like obtained from the patient through a sample. Further, information concerning the patient can be supplied in conjunction with the test. Such information includes, but is not limited to, age, weight, blood pressure, genetic history, and the other such parameters or variables.

The exemplary biochemical test developed in this embodiment employs a standardized test format, such as the Enzyme Linked Immunosorbent Assay or ELISA test, although the information provided herein may apply to the development of other biochemical or diagnostic tests and is not limited to the development of an ELISA test (see, eg., *Molecular Immunology: A Textbook*, edited by Atassi et al. Marcel Dekker Inc., New York and Basel 1984, for a description of ELISA tests). Information important to the development of the ELISA test can be found in the Western Blot test, a test format that determines antibody reactivity to proteins in order to characterize antibody profiles and extract their properties.

A Western Blot is a technique used to identify, for example, particular antigens in a mixture by separating these antigens on polyacrylamide gels, blotting onto nitrocellulose, and detecting with labeled antibodies as probes. (See, for example, *Basic and Clinical Immunology*, Seventh Edition, edited by Stites and Terr, Appleton and Large 1991, for information on Western Blots.) It is, however, sometimes undesirable to employ the Western Blot test as a diagnostic tool. If instead, ranges of molecular weight that contain relevant information to the diagnosis can be pre-identified then this information can be "coded" into an equivalent ELISA test.

Figure 5:
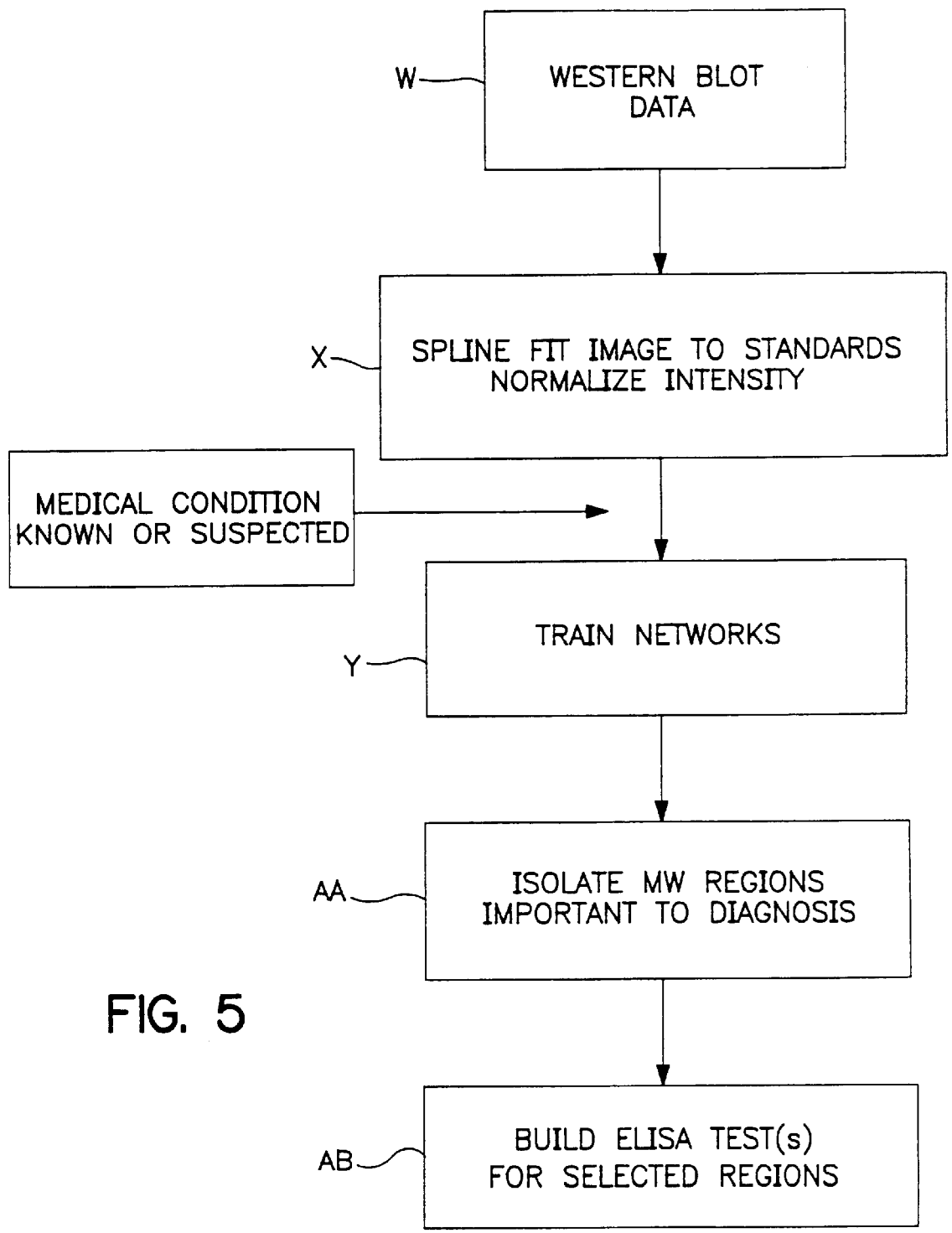
FIG. 5 is a flow chart for developing a biochemical diagnostic test.

In this example, the development of an effective biochemical diagnostic test is dependent upon the availability of Western Blot data for the patients for which the disease condition is known or suspected. Referring to FIG. 5, Western Blot data are used as a source (Step W), and the first step in processing the Western Blot data are to pre-process the Western Blot data for use by the neural network (Step X). Images are digitized and converted to fixed dimension training records by using a computer to perform the spline interpolation and image normalization. It is necessary to align images on a given gel based only on information in the image in order to use data from multiple Western Blot tests. Each input of a neural network needs to represent a specific molecular weight or range of molecular weights accurately. Normally, each gel produced contains a standards image for calibration, wherein the proteins contained are of a known molecular weight, so that the standards image can also be used for alignment of images contained within the same Western Blot. For example, a standard curve can be used to estimate the molecular weight range of other images on the same Western Blot and thereby align the nitrocellulose strips.

The process for alignment of images is cubic spline interpolation. This is a method which guarantees smooth transitions at the data points represented by the standards. To avoid possible performance problems due to extrapolation, termination conditions are set so that extrapolation is linear. This alignment step minimizes the variations in the estimates of molecular weight for a given band on the output of the Western Blot.

The resultant scanned image is then processed to normalize the density of the image by scaling the density so that the darkest band has a scaled density of 1.0 and the lightest band is scaled to 0.0. The image is then processed into a fixed length vector of numbers which become the inputs to a neural network, which at the outset must be trained as hereinafter explained.

A training example is built in a process similar to that previously described where the results generated from the processing of the Western Blot data are trained (Step Y). To minimize the recognized problems of dependency on starting weights, redundancy among interdependent variables, and desensitivity resulting from overtraining a network, it is helpful to train a set of neural networks (consensus) on the data by the partitioning method discussed previously.

From the sensitivity analysis of the training runs on the processed Western Blot data, regions of significantly contributing molecular weights (MW) can be determined and identified (Step AA). As part of the isolation step, inputs in contiguous regions are preferably combined into "bins" as long as the sign of the correlation between the input and the desired output is the same. This process reduces the typical 100-plus inputs produced by the Western Blot, plus the other inputs, to a much more manageable number of inputs of less than about twenty.

In a particular embodiment, it may be found that several ranges of molecular weight may correlate with the desired output, indicative of the condition being diagnosed. A correlation may be either positive or negative. A reduced input representation may be produced by using a Gaussian region centered on each of the peaks found in the Western Blot training, with a standard deviation determined so that the value of the Gaussian was below 0.5 at the edges of the region.

In a specific embodiment, the basic operation to generate the neural network input is to perform a convolution between the Gaussian and the Western Blot image, using the log of the molecular weight for calculation.

The data may be tested using the holdout method, as previously described. For example, five partitions might be used where, in each partition, 80% of the data are used for training and 20% of the data are used for testing. The data are shuffled so that each of the partitions is likely to have examples from each of the gels.

Once the molecular weight regions important to diagnosis have been identified (Step AA), one or more tests for the selected region or regions of molecular weight may be built (Step AB). The ELISA biochemical test is one example. The selected region or regions of molecular weight identified as important to the diagnosis may then be physically identified and used as a component of the ELISA biochemical test. Whereas regions of the same correlation sign may, or may not, be combined into a single ELISA test, regions of differing correlation signs should not be combined into a single test. The value of such a biochemical test may then be determined by comparing the biochemical test result with the known or suspected medical condition.

Figure 2:
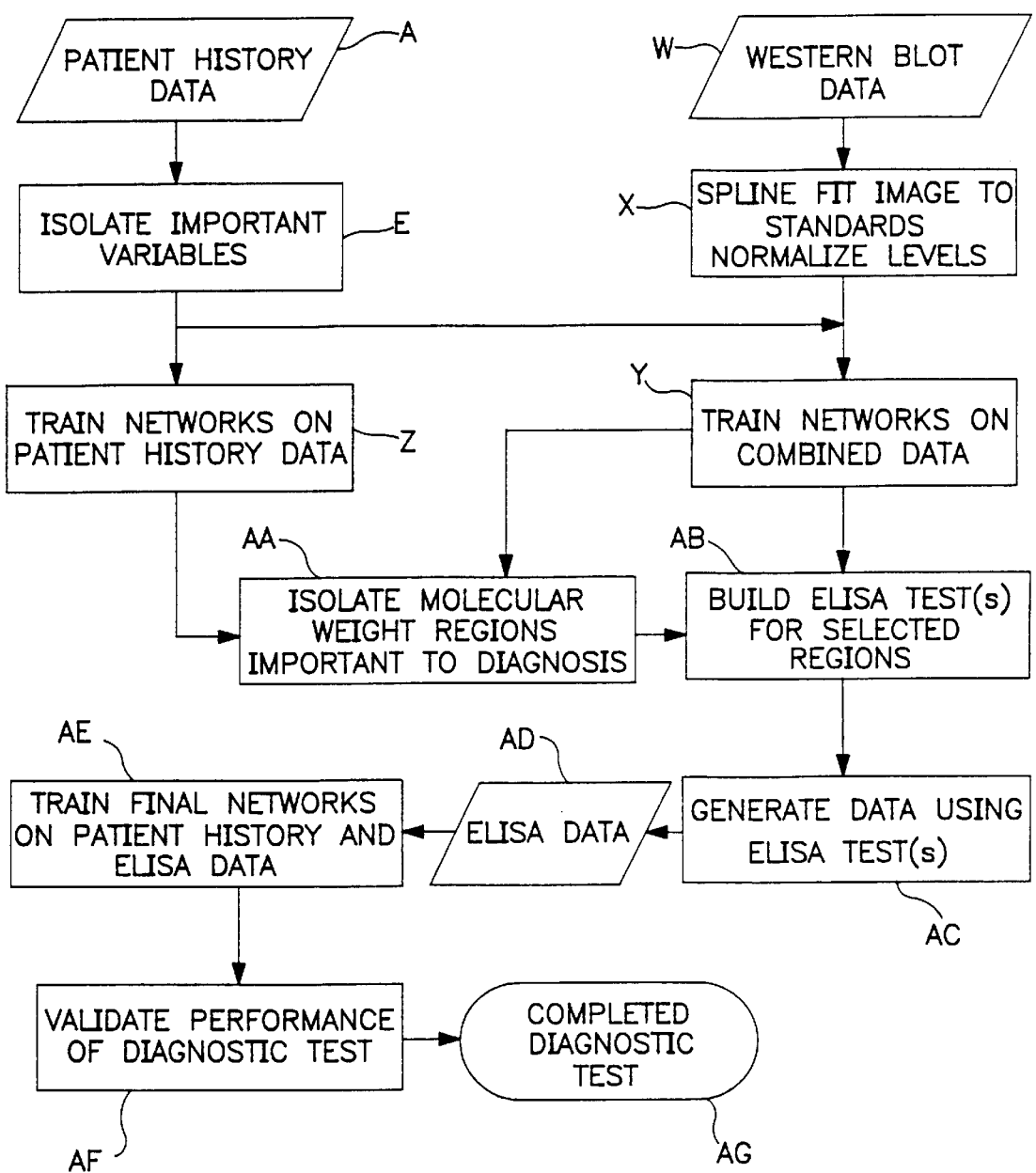
FIG. 2 is a flow chart for developing a biochemical diagnostic test.

In this example, the development of a biochemical diagnostic test may be enhanced by combining patient data and biochemical data in a process shown in FIG. 2. Under these conditions, the patient history diagnostic test is the basis for the biochemical diagnostic test. As explained herein, the variables that are identified as important variables are combined with data derived from the Western Blot data in order to train a set of neural networks to be used to identify molecular weight regions that are important to a diagnosis.

Referring to FIG. 2, Western Blot data are used as a source (Step W) and pre-processed for use by the neural network as described previously (Step X). A training example is built in a process similar to that previously described wherein the important variables from the patient history data and the results generated from the processing of the Western Blot data are combined and are trained using the combined data (Step Y). In parallel, networks are trained on patient history data, as described above (Step Z).

To minimize the recognized problems of dependency on starting weights, redundancy among interdependent variables, and desensitivity resulting from overtraining a network, it was found that it was preferable to train a set of neural networks (consensus set) on the data by the partitioning method. From the sensitivity analysis of the training runs on patient history data alone and on combined data, regions of significantly contributing molecular weights can be determined and identified as previously described (Step AA). As a further step in the isolation process, a set of networks is thereafter trained using as inputs the combined patient history and bin information in order to isolate the important bins for the Western Blot data. The "important bins" represent the important regions of molecular weight related to the diagnosis considering the contribution of patient history information. These bins are either positively or negatively correlated with the desired output of the diagnosis.

Once the molecular weight regions important to diagnosis have been identified (Step AA), one or more tests for the selected region or regions may be built and validated as previously described (Step AB). The designed ELISA tests are then produced and used to generate ELISA data for each patient in the database (Step AC). Using ELISA data and the important patient history data as input, a set of networks is trained using the partition approach as described above (Step AE). The partition approach can be used to obtain an estimate of the lower bound of the biochemical test. The final training (Step AE) of a set of networks, i.e., the networks to be used as a deliverable product, is made using all available data as part of the training data. If desired, new data may be used to validate the performance of the diagnostic test (Step AF). The performance on all the training data becomes the upper bound on the performance estimate for the biochemical test. The consensus of the networks represents the intended diagnostic test output (AG). This final set of neural networks can then be used for diagnosis.

4. Improvement of Neural Network Performance

An important feature of the decision-support systems, as exemplified with the neural networks, and methods provided herein is the ability to improve performance. The training methodology outlined above may be repeated as more information becomes available. During operation, all input and output variables are recorded and augment the training data in future training sessions. In this way, the diagnostic neural network may adapt to individual populations and to gradual changes in population characteristics.

If the trained neural network is contained within an apparatus that allows the user to enter the required information and outputs to the user the neural network score, then the process of improving performance through use may be automated. Each entry and corresponding output is retained in memory. Since the steps for retraining the network can be encoded into the apparatus, the network can be re-trained at any time with data that are specific to the population.

5. Method for Evaluating the Effectiveness of a Diagnostic Test Course of Treatment Typically, the effectiveness or usefulness of a diagnostic test is determined by comparing the diagnostic test result with the patient medical condition that is either known or suspected. A diagnostic test is considered to be of value if there is good correlation between the diagnostic test result and the patient medical condition; the better the correlation between the diagnostic test result and the patient medical condition, the higher the value placed on the effectiveness of the diagnostic test. In the absence of such a correlation, a diagnostic test is considered to be of lesser value. The systems provided herein, provide a means to assess the effectiveness of a biochemical test by determining whether the variable that corresponds to that test is an important selected variable. Any test that yields data that improves the performance of the system is identified.

Figure 6:
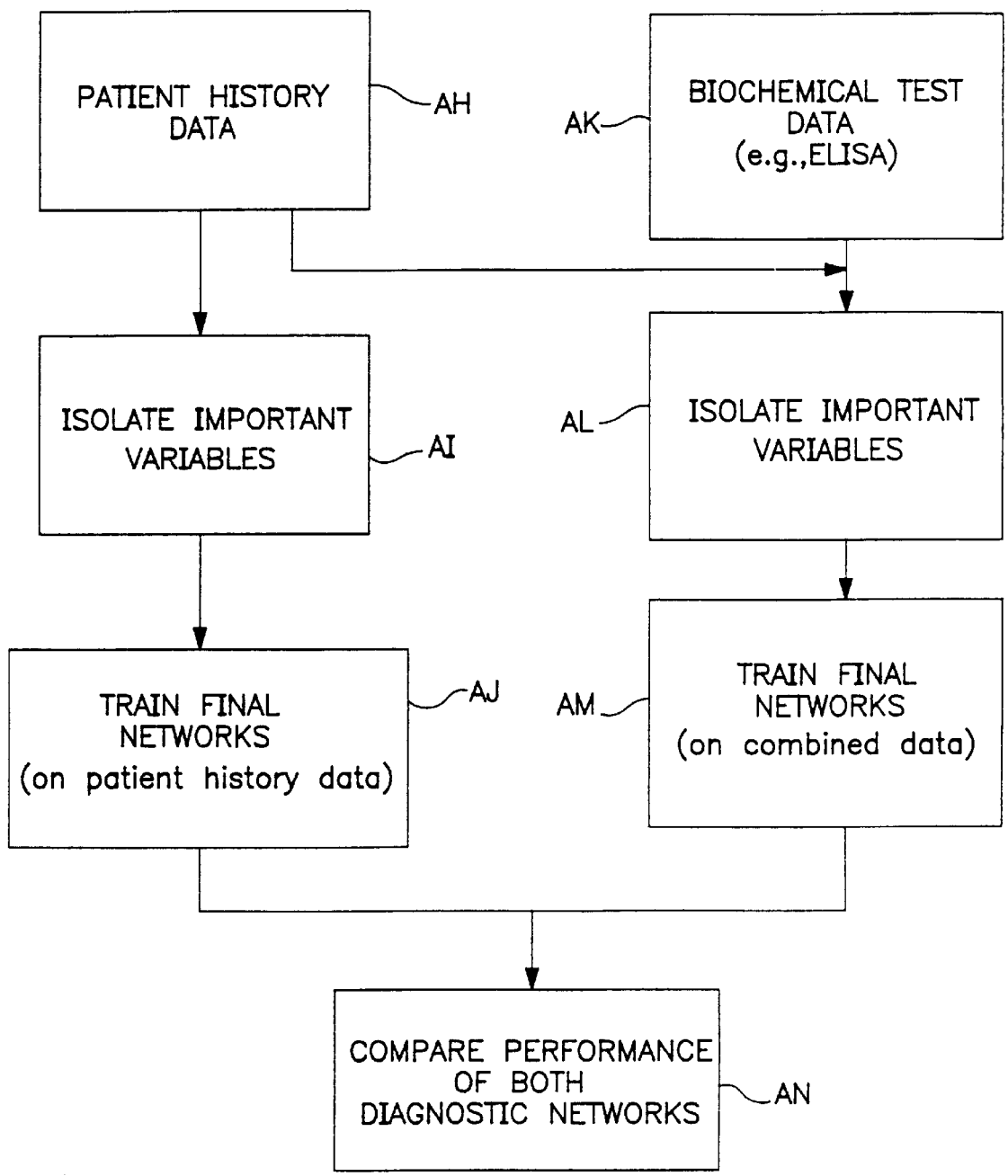
FIG. 6 is a flow chart for determining the effectiveness of a biochemical diagnostic test.

A method by which the effectiveness of a diagnostic test may be determined, independent of the correlation between the diagnostic test result and the patient medical condition (FIG. 6) is described below. A similar method may be used to assess the effectiveness of a particular treatment.

In one embodiment, the method compares the performance of a patient history diagnostic neural network trained on patient data alone, with the performance of a combined neural network trained on the combination of patient historical data and biochemical test data, such as ELISA data. Patient history data are used to isolate important variables for the diagnosis (Step AH), and final neural networks are trained (Step AJ), all as previously described. In parallel, biochemical test results are provided for all or a subset of the patients for whom the patient data are known (Step AK), and a diagnostic neural network is trained on the combined patient and biochemical data by first isolating important variables for the diagnosis (Step AL), and subsequently training the final neural networks (Step AM), all as previously described.

The performance of the patient history diagnostic neural network derived from Step AJ is then compared with the performance of the combined diagnostic neural network derived from Step AM, in Step AN. The performance of a diagnostic neural network may be measured by any number of means. In one example, the correlations between each diagnostic neural network output to the known or suspected medical condition of the patient are compared. Performance can then be measured as a function of this correlation. There are many other ways to measure performance. In this example, any increase in the performance of the diagnostic neural network derived from Step AM over that derived from Step AJ is used as a measure of the effectiveness of the biochemical test.

A biochemical test in this example, and any diagnostic test in general, that lacks sufficient correlation between that test result and the known or suspected medical condition, is traditionally considered to be of limited utility. Such a test may be shown to have some use through the method described above, thereby enhancing the effectiveness of that test which otherwise might be considered uninformative. The method described herein serves two functions: it provides a means of evaluating the usefulness of a diagnostic test, and also provides a means of enhancing the effectiveness of a diagnostic test.

6. Application of the Methods to Identification of Variables for Diagnosis and Development of Diagnostic Tests The methods and networks provided herein provide a means to, for example, identify important variables, improve upon existing biochemical tests, develop new tests, assess therapeutic progress, and identify new disease markers. To demonstrate these advantages, the methods have been to pregnancy related events, such as the likelihood of labor and delivery during a particular period.

Predicting Pregnancy Related Events, Such as the Likelihood of Delivery Within a Particular Time Period The methods herein may be applied to any disorder or condition, and are particularly suitable for conditions in which no diagnostic test can be adequately correlated or for which no biochemical test or convenient biochemical test is available. The methods herein have been applied to predicting pregnancy related events, such as the likelihood of delivery within a particular time period.

Biochemical and Other Markers for Assessment of the Risk of Preterm Delivery or Delivery Within a Selected Period of Time Determination of impending birth is of importance, example, for increasing neonatal survival of infants born before 34 weeks. The presence of fetal fibronectin in secretion samples from the vaginal cavity or the cervical canal from a pregnant patient after week 20 of pregnancy is associated with a risk of labor and delivery before 34 weeks. Methods and kits for screening for fetal fibronectin in body fluids and tissues, particularly in secretion samples from the vaginal cavity or the cervical canal, of a pregnant patient after week 20 of pregnancy are available (see, U.S. Pat. Nos. 5,516,702, 5,468,619, and 5,281,522, and 5,096,830; see, also U.S. Pat. Nos. 5,236,846, 5,223,440, 5,185,270; see also, U.S. Pat. Nos. 5,623,939, 5,480,776, 5,474,927, 5,279, 941 and 5,091,170 for other biochemical tests and markers).

For example U.S. Pat. No. 5,468,619 provides a biochemical indication of increased risk of impending delivery. The method is particularly useful to identify those pregnant women who are at increased risk for preterm delivery. The method can also be used to detect those women who are at risk for post-date delivery. The method includes obtaining a cervicovaginal secretion sample from a pregnant patient after about week twelve of gestation and determining the level of total fibronectin in the sample. The presence of an elevated fibronectin level in the sample indicates an increased risk of imminent delivery. The test is a sensitive and specific screen for pregnancies at risk and can detect impending delivery about two to three weeks prior to delivery.

This test is preferably administered to women at about 12 weeks gestation and repeated at each perinatal visit (every two to four weeks) until at least week 37, preferably until delivery, if the test is negative. For those patients whose assay result indicates an increased risk of preterm delivery, a test of the patient's fetal fibronectin level can be made to confirm the increased risk and to estimate time of delivery. Using these results in combination with a decision support system or a part of the set of training variable improves the predictive ability of the biochemical test.

U.S. Pat. No. 5,281,522 provides a biochemical test for increased risk of preterm labor and rupture of the amniotic membrane after week 20 of pregnancy is directed to an assay of a test sample removed from the vicinity of the posterior fornix, cervical canal, or cervical os.

U.S. Pat. No. 5,516,702 describes a biochemical indication and method of asssessing increased risk of impending preterm delivery. The method involves obtaining a cervicovaginal secretion sample from a pregnant patient after and determining the level of a local inflammatory product protein, such as IL-6, in the sample. The presence of an elevated level of the selected local inflammatory product in the sample indicates an increased risk of imminent delivery. The test is a sensitive and specific screen for pregnancies at risk and can detect impending delivery as early as two to three weeks prior to delivery. For those patients whose assay result indicates an increased risk of preterm delivery, a test of the patient's fetal fibronectin level can be made to confirm the increased risk and to estimate how soon the delivery may be. In addition, those patients can be carefully monitored, as for other patients at risk.

U.S. Pat. No. 5,480,776 describes a method for predicting the onset of preterm labor at 36 weeks or earlier by analyzing unconjugated estriol levels in a body fluid, saliva, and correlating the levels with either: a predetermined standard unconjugated estriol concentration for the body fluid, or a previously measured unconjugated estriol concentration in the body fluid of said pregnant human to determine a rate of increase in unconjugated estriol concentration in the body fluid of said pregnant human. A higher concentration of unconjugated estriol in the body fluid of the pregnant human relative to a predetermined standard unconjugated estriol concentration, or an elevated rate of increase in unconjugated estriol concentration in the body fluid is an indication of potential onset of preterm labor.

Estetrol is also used as an indicator of preterm delivery (see, International PCT application No. W096/03929, entitled Method for Prediction of Premature Delivery Using Estetrol ($E_4$) As an Indicator.

Other markers indicative of assessment of a risk of preterm delivery or delivery within a selected period of time that be used in combination with the methods and decision support systems provided herein include, but are not limited to the following: corticotropin-releasing hormone (CRH), which can be sampled, for example, from serum; estriol E3 and estretol, noted above, which can be sampled, for example, from saliva or serum; cerivcovaginal dehydroepiandrosterone (DHEA), which can be sampled, for example, from serum; FasL (ligand for Fas receptor, an oncogene that mediates programmed cell death), which can be sampled, for example, from serum; beta human chorionic gonadotropin ($\beta$-hcG), which can be sampled, for example, from serum and cerivcovaginal area; insulin-like growth factor binding protein-1 (IGFBP-1), which can be sampled, for example, from serum; Uterine Artery Doppler, which can be sampled, for example, from uterus (by transvaginal ultrasonography (TVS)); Umbilical Artery Doppler, which can be sampled, for example, from fetus; Mid. Cerebral Artery Doppler, which can be sampled, for example, from fetus; Ultrasound estimated fetal weight percentile, which can be sampled, for example, from fetus; IL-6, which can be sampled, for example, from serum, cervix; GCSF, which can be sampled, for example, from serum bacterial vaginosis, which can be sampled, for example, from vagina gross or occult blood, which can be sampled, for example, from vagina; tPA (activity), which can be sampled, for example, from plasma; thrombin-ATIII Complexes, which can be sampled, for example, from plasma; amniotic fluid index, for example, from uterus no. fetuses, which can be sampled, for example, from uterus; matrix metalloproteinase-1 (MMP-1), which can be sampled, for example, from cervix; matrix metalloprteinase-9 (MMP-9), which can be sampled, for example, from cervix; fFN, which can be sampled, for example, from cervix and vagina cervical length (TVS), which can be sampled, for example, from vagina.

As noted above, methods and kits for screening for fetal fibronectin in body fluids and tissues, particularly in secretion samples from the vaginal cavity or the cervical canal of a pregnant patient, particularly after week 20 of pregnancy are available (see, U.S. Pat. Nos. 5,516,702, 5,468,619, and 5,281,522, and 5,096,830). The correlation between the presence of fetal fibronectin in these secretions and the labor and delivery before 34–35 weeks is not perfect; there are significant false-negative and false-positive rates. Consequently, to address the need for methods to assess the likelihood of labor and delivery before 34 weeks and to improve the predictability of the available tests, the methods herein have been applied to development of a decision-support system that assesses the likelihood of certain pregnancy related events. In particular, neural nets for predicting delivery before (and after) 34 weeks of gestation have been developed. Neural networks and other decision-support systems developed as described herein can improve the performance of the fetal fibronectin (fFN) test by lowering the number of false positives.

The results, which are shown in the EXAMPLE, demonstrate that use of the methods herein can improve the diagnostic utility of existing tests by improving predictive performance. EXEMPLARY neural networks and implementing software (APPENDIX III) are also described.

In addition, the methods herein can identify additional markers and tests of relevance or use in assessing the risk of preterm delivery or delivery within a selected period of time.

PreTerm Delivery Risk Assessment Software

The Pre-term Delivery Risk Assessment Software (designated ptdinp.exe in Appendix III) program provides a means to input patient historical information and fFN test results into a database of fixed length ASCII records, and to perform the calculations necessary to generate inputs to three neural network tests used to evaluate the patients risks related to pre-term delivery. The software generates outputs that define the risk of preterm delivery. The Preterm Delivery Risk Assessment Software provided herein classifies the fFN ELISA positive results into 3 clinically distinct groups. In so doing, more than 50% of the fFN ELISA false positive results can be immediately identified. Moreover, about 35% of the true positive results can be rescued. The combination of the Preterm Delivery Risk Assessment Software with the ELISA test result provides new information which the clinician can use to improve the management of symptomatic patients. In particular, risk of delivery less than or equal to 34 week, 6 days, risk of delivery less than or equal to 7 days from time of sampling for fFN, and risk of delivery less than or equal to 14 days from time of sampling for fFN. The exemplified software uses neural networks designated EGA6, EGA7f and EGA14f (see Example) herein, but can be used with any nets provided herein or developed based on the methods provided herein. The source code for the software is set forth in Appendix III. The following is a description of the operation, inputs and outputs of the software.

A. User Interface

A typical user interface is depicted in FIGS. 7–10 and exemplary printed outputs are depicted in FIGS. 11A and 11B.

Main Menu

Figure 7:
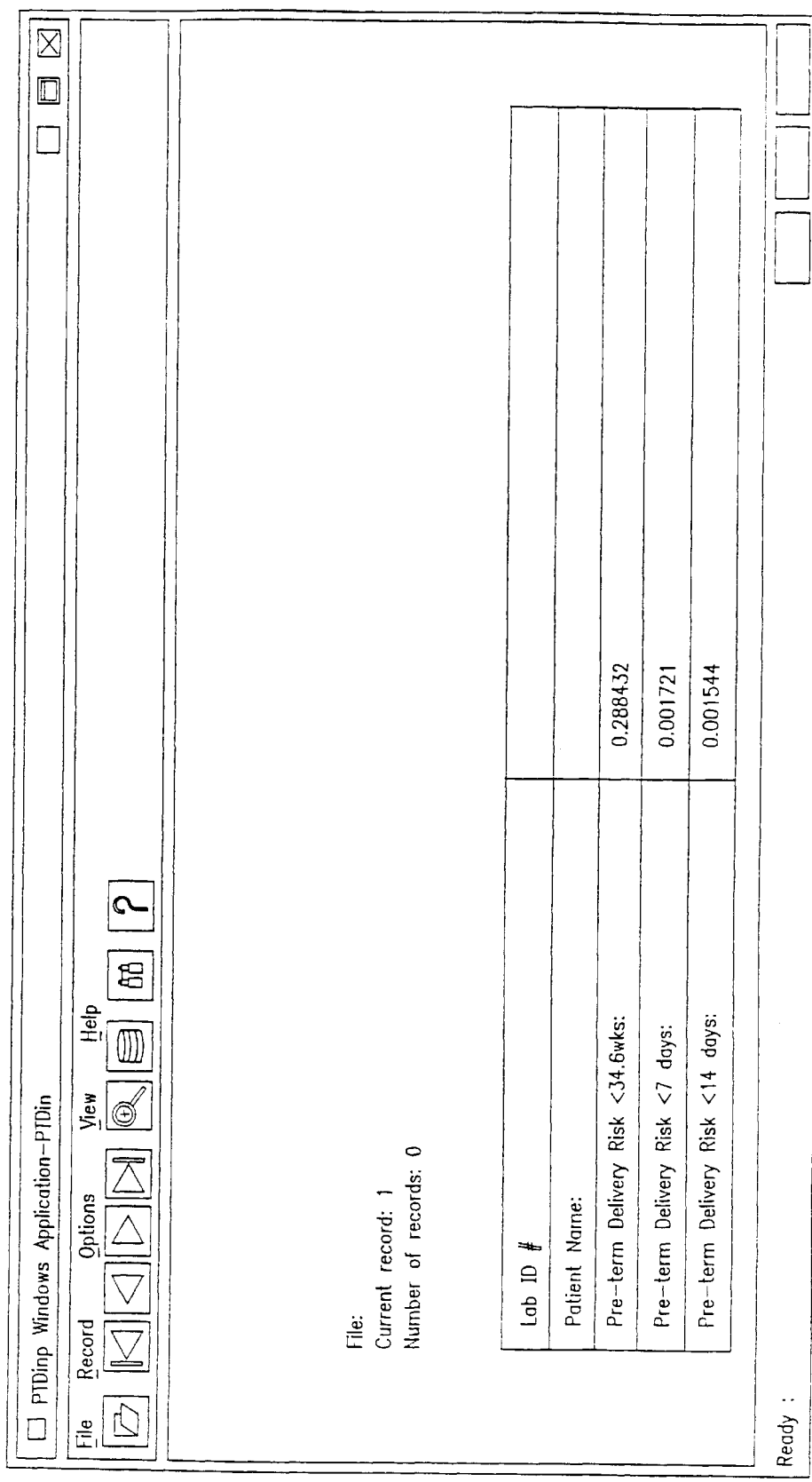
FIG. 7 depicts an exemplary screen showing main menu, tool bar and results display in the user interface using the software (Appendix III) for assessing preterm delivery.

The main menu, tool bar and results display appear as shown in FIG. 7. The various fields in the main window are calculated as follows:

File: The name of the fdb file opened by the user.

Current Record: The record number counting from 1 that is currently displayed.

Number of records: The count of records contained in the open file.

Lab ID #: The contents of the associated field in the fixed length data record entered by the user.

Patient Name: The first, middle initial, and last name of the patient from the fixed length data record.

Pre-term Delivery Risk$\leq$34 weeks 6 days, which is the consensus score from the ega6 set of neural networks.

Pre-term Delivery Risk$\leq$7 days: The consensus score from the egad7f set of neural networks.

Pre-term Delivery Risk$\leq$14 days: The consensus score from the egad14f set of neural networks.

The File item on the main menu contains the following sub menu items and functions;

Open: Open a fixed length database file (.fdb) for entry and examination.

Print: Print the current record in one of the two formats as specified in the Options menu.

Print Setup: Provides standard Windows support for print functions tup.

Print Preview: Provides standard Windows support for print viewing.

MRU List: Provides a list of the four Most Recently Used files.

Exit: To Exit the program.

The Record item on the main menu will contain the following sub menu items and functions:

First Record: Display the first record in the database file.

Next Record: Display the next record in the database file.

Previous Record: Display the previous record in the database file.

Last Record: Display the last record in the database file.

Go to Record: Opens a dialog to go to a specific record number or search for a specific Lab ID #.

Edit Record: Opens a dialog to allow the examination and modification of data in the displayed record.

New Record: Creates a new record at the end of the database and automatically edits the record.

The Options item on the main menu will contain the following sub menu items and functions;

Print full form: When checked, the print function will print the full record as shown in the edit record dialog box. When unchecked, the print function will print the information shown in the main window. The default setting is unchecked.

Clear sub fields: When checked, sub fields will be cleared when field is unchecked in the edit dialog. The default setting is checked.

The View item on the main menu will contain the following sub menu items and functions:

Toolbar: Standard Windows Toolbar appears when checked.

Status Bar: Standard Windows Status Bar appears when checked.

The Help item on the main menu will contain the following sub menu items and functions;

About PTDinp: Provide version number, program icon, and developer of the program.

Tool Bar buttons will be provided for the following functions:

File Open
View First Record
View Previous Record
View Next Record
View Last Record
Edit Record
New Record
Go To Record
Help About
Edit Dialog An exemplary Edit Record dialog box is set forth in FIG. 8. Through this dialog the user can exam, change or input patient specific data into a fixed length database record. The table below provides the size and location of each item in the fixed length database record. For entry into the dialog box relevant items are checked; all checked items are assigned a value of 1, all others are assigned a value of 0. The alphanumeric fields in the dialog box, such as Lab ID #, name, date of birth, EGA boxes, G (gravity), P (parity), A (abortions) are assigned the entered values. The table set forth (True=checked, false=unchecked) below summarizes how the information entered into the dialog box is converted for storage in the fixed length database record.

| NAME | POSITION | WIDTH | DESCRIPTION |
|---|---|---|---|
| LAB ID # | 1 | 12 | ACSII text |
| LAST NAME | 13 | 24 | ACSII text |
| FIRST NAME | 37 | 24 | ACSII text |
| MIDDLE INITIAL | 61 | 2 | ACSII text |
| DATE OF BIRTH | 93 | 10 | ACSII mm/dd/yy |
| ETHNIC ORIGIN WHITE | 103 | 2 | 0 = FALSE 1 = TRUE |
| ETHNIC ORIGIN BLACK | 105 | 2 | 0 = FALSE 1 = TRUE |
| ETHNIC ORIGIN ASIAN | 107 | 2 | 0 = FALSE 1 = TRUE |
| ETHNIC ORIGIN HISPANIC | 109 | 2 | 0 = FALSE 1 = TRUE |
| ETHNIC ORIGIN NATIVE AMERICAN | 111 | 2 | 0 = FALSE 1 = TRUE |
| ETHNIC ORIGIN OTHER | 113 | 2 | 0 = FALSE 1 = TRUE |
| MARITAL STATUS | 115 | 2 | 1 = Single (only one box can be checked) 2 = Married 3 = Divorced 4 = Widowed 5 = Living with partner 6 = Other |
| Symptoms of Preterm labor | 117 | 2 | 0 = No 1 = Yes |
| Vaginal Bleeding | 119 | 2 | 0 = N/A (check if sub field checked) 1 = Trace 2 = Medium 3 = Gross |
| Uterine Contractions | 121 | 2 | 0 = FALSE 1 = TRUE |
| Intermittent lower abdominal pain, dull low back pain | 123 | 2 | 0 = FALSE 1 = TRUE |
| Bleeding during the second or third trimester | 125 | 2 | 0 = FALSE 1 = TRUE |
| Menstrual-like or intestinal cramping | 127 | 2 | 0 = FALSE 1 = TRUE |
| Change in vaginal discharge | 129 | 2 | 0 = FALSE 1 = TRUE |
| Patient is not "feeling right" | 131 | 2 | 0 = FALSE 1 = TRUE |
| Number/hr. | 133 | 2 | 0 = Uterine Contractions FALSE 1 = "<1" 2 = "1–3" 3 = "4–6" 4 = "7–9" 5 = "10–12" 6 = ">12" |
| EGA by SONO | 135 | 8 | ACSII weeks · days format |
| EGA by LMP | 143 | 8 | ACSII weeks · days format |
| EGA at Sampling | 151 | 8 | ACSII weeks · days format |
| GRAVITY (G:) | 159 | 2 | ASCII number |
| PARITY (P:) | 161 | 2 | ASCII number |
| ABORTIONS (A:) | 163 | 2 | ASCII number |
| Number of Preterm delivery | 165 | 2 | 0 = NONE 1 = "1" 2 = "2" 3 = ">2" |
| No previous pregnancies | 167 | 2 | 1 = "Gravity = 0" |
| Previous pregnancies with no complications | 169 | 2 | 0 = FALSE 1 = TRUE |
| History of Preterm delivery | 171 | 2 | 0 = FALSE 1 = TRUE |
| History of preterm PROM | 173 | 2 | 0 = FALSE 1 = TRUE |
| History of incompetent cervix | 175 | 2 | 0 = FALSE 1 = TRUE |
| History of PIH/preeclampsia | 177 | 2 | 0 = FALSE 1 = TRUE |
| History of SAB prior to 20 weeks | 179 | 2 | 0 = FALSE 1 = TRUE |
| Multiple Gestation | 181 | 2 | 0 = NONE (unchecked) 1 = "Twins" 2 = "Triplets" 3 = "Quads" |
| Uterine or cervical abnormality | 183 | 2 | 0 = FALSE 1 = TRUE |
| Cerclage | 185 | 2 | 0 = FALSE 1 = TRUE |
| Gestational Diabetes | 187 | 2 | 0 = FALSE 1 = TRUE |
| Hypertensive Disorders | 189 | 2 | 0 = FALSE 1 = TRUE |
| Dilation | 191 | 2 | 0 = Unk. Or None checked |

-continued

| NAME | POSITION | WIDTH | DESCRIPTION |
|---|---|---|---|
| Cervical Consistency | 193 | 2 | 1 = "<1" 2 = "1" 3 = "1–2" 4 = "2"<br>5 = "2–3" 6 = "3" 7 = ">3"<br>blank = (unchecked<br>1 "Firm" 2 = "Mod" 3 = "Soft" |
| Antibiotics | 195 | 2 | 0 = FALSE 1 = TRUE |
| Corticosteroids | 197 | 2 | 0 = FALSE 1 = TRUE |
| Tocolytis | 199 | 2 | 0 = FALSE 1 = TRUE |
| Insulin | 201 | 2 | 0 = FALSE 1 = TRUE |
| Antihypertensives | 203 | 2 | 0 = FALSE 1 = TRUE |
| Medication: None | 205 | 2 | 0 = FALSE 1 = TRUE |
| Medication: Unknown | 207 | 2 | 0 = FALSE 1 = TRUE |
| Qualitative fFN Result | 209 | 2 | 0 = FALSE 1 = TRUE |
| <34.6 Net Output Positive | 211 | 20 | ASCII coded float |
| <34.6 Net Output Negative | 231 | 20 | ASCII coded float |
| <7 Day Net Output Positive | 251 | 20 | ASCII coded float |
| <7 Day Net Output Negative | 271 | 20 | ASCII coded float |
| <14 Day Net Output Positive | 291 | 20 | ASCII coded float |
| <14 Day Net Output Negative | 311 | 20 | ASCII coded float |

Go To Dialog

The Go To dialog box is shown in FIG. 9. The user may enter either the record number or the Lab ID number. When OK is pressed the record is found and displayed based on the information contained in a database record.

Help About Dialog The Help About dialog box, which can provide information, such as the title of the software, version and copyright information, is shown in FIG. 10.

B. Pre-term Delivery Risk Evaluation

1. Loading the Networks

When a new database is opened or the program is first run, the neural networks associated with the risk evaluations are loaded. For each risk evaluation there are 8 neural networks that must be loaded. This is performed by repeated calls to the LoadNet function of the ThinksPro TKSDLL.DLL (a WINDOWS™ dynamic link library). Other suitable programs can be used to run the neural networks described herein. The LoadNet function automatically loads the weights associated with each network.

For the ≦34 weeks, 6 days evaluation the following nets (described in the Example) are loaded.

Ega6_0
Ega6_1
Ega6_2
Ega6_3
Ega6_4
Ega6_5
Ega6_6
Ega6_7.

For the ≦7 days evaluation the following nets are loaded:

Egad7f0
Egad7f1
Egad7f2
Egad7f3
Egad7f4
Egad7f5
Egad7f6
Egad7f7

For the ≦14 days evaluation the following nets are loaded:

Egad14f0
Egad14f1
Egad14f2
Egad14f3
Egad14f4
Egad14f5
Egad14f6
Egad14f7

2. Processing the Inputs and Outputs

To run the evaluation of the pre-term delivery risks, data from the database record must be processed for use by the neural networks. The networks are run for a given evaluation when the "calculate risk" button is pressed in the edit record dialog (FIG. 8). The positive outputs (described below) of each network are averaged together to produce the value that is displayed, printed and placed in the database. The negative outputs (described below) are averaged and the result is placed in the database only.

a. For the ≦34 weeks, 6 days (referred to herein as 34.6) evaluation

The ≦34.6 networks use 11 inputs generated from the database record. These inputs are calculated as follows.

1. Ethnic Origin White: 1.0 input if TRUE, 0.0 input if FALSE.
2. Marital Status Living with Partner: 1.0 input if TRUE, 0.0 input if FALSE.
3. EGA by SONO: Convert from weeks.days to weeks.
4. Val1=EGA by LMP: Convert from weeks.days to weeks. Val2=EGA by SONO: Convert from weeks.days to weeks. If Val2<=13.0 then input is Val2; Else if the difference between Val1 and Val2 is >2 then input is Val1. Else input is Val2.
5. EGA at Sample: Convert from weeks.days to weeks.
6. If Dilatation none then input is 0.0.
   If Dilatation <1 then input is 0.0.
   If Dilatation 1 then input is 1.0.
   If Dilatation 1–2 then input is 1.5.
   If Dilatation 2 then input is 2.0.
   If Dilatation 2–3 then input is 2.0.
   If Dilatation 3 then input is 3.0.
   If Dilatation >3 then input is 3.0.
7. If Number of Preterm Delivery=0 then input is 0.0.
   If Number of Preterm Delivery=1 then input is 1.0.
     If Number of Preterm Delivery =2 then input is 2.0.
   If Number of Preterm Delivery >2 then input is 3.0.
8. Vaginal Bleeding: 1.0 input if TRUE, 0.0 input if FALSE.
9. If Cervical Consistency unchecked then input is 1.823197.

If Cervical Consistency Firm then input is 1.0.

If Cervical Consistency Mod then input is 2.0.

If Cervical Consistency Soft then input is 3.0.

10. Previous pregnancies with no complications: 1.0 input if TRUE, 0.0 input if FALSE.
11. FFN Result: 1.0 input if Positive, 0.0 input if negative.
   b. For the ≤7 days evaluation The ≤7 day networks use 7 inputs generated from the database record. These puts are calculated as follows.

1. Ethnic Origin White: 1.0 input if TRUE, 0.0 input if FALSE.
2. Uterine Contractions: 1.0 input if TRUE, 0.0 input if FALSE.
3. Number of Abortions: Convert to float.
4. Vaginal Bleeding: 1.0 input if TRUE, 0.0 input if FALSE.
5. If Number/hr unchecked then input 0.0.

If Number/hr <1 then input 1.0.

If Number/hr 1–3 then input 2.0.

If Number/hr 4–6 then input 3.0.

If Number/hr 7–9 then input 4.0.

If Number/hr 10–12 then input 5.0.

If Number/hr >1 2 then input 6.0

6. No previous pregnancies: 1.0 input if TRUE, 0.0 input if FALSE.
7. fFN Result: 1.0 input if Positive, 0.0 input if negative.
   c. For the <14 days evaluation The ≤14 day networks use 7 inputs generated from the database record. These inputs are calculated as follows.

1. Ethnic Origin Native American: 1.0 input if TRUE, 0.0 input if FALSE.
2. Marital Status Living with Partner: 1.0 input if TRUE, 0.0 input if FALSE.
3. Uterine Contractions: 1.0 input if TRUE, 0.0 input if FALSE.
4. If Dilatation none then input is 0.0.

If Dilatation <1 then input is 0.0.

If Dilatation 1 then input is 1.0.

If Dilatation 1–2 then input is 1.5.

If Dilatation 2 then input is 2.0.

If Dilatation 2–3 then input is 2.0.

If Dilatation 3 then input is 3.0.

If Dilatation >3 then input is 3.0.

5. If Number/hr unchecked then input 0.0.

If Number/hr <1 then input 1.0.

If Number/hr 1–3 then input 2.0.

If Number/hr 4–6 then input 3.0.

If Number/hr 7–9 then input 4.0.

If Number/hr 10–12 then input 5.0.

If Number/hr >1 2 then input 6.0.

6. No previous pregnancies: 1.0 input if TRUE, 0.0 input if FALSE.
7. FFN Result: 1.0 input if Positive , 0.0 input if negative.

3. Print Functions and Output Interpretation

Based on the print full form option (options menu), print the full form if the option is checked and the results only if the option is not checked. FIGS. 11A and 11B show exemplary output formats, with the risk indices for each net, which are interpreted according to the following tables:

| Risk of Preterm Delivery (Delivery before 34 weeks 6 days gestation) | |
|---|---|
| Risk Index | Interpretation |
| ≤.30 | low risk |
| >.30 | high risk |

| Risk of Delivery within 14 days of sampling for fFN Qual ELISA. | |
|---|---|
| Risk Index | Interpretation |
| ≤0.10 | low risk |
| 0.10–0.40 | moderate risk |
| >0.40 | high risk |

| Risk of Delivery within 7 days of sampling for fFN Qual ELISA. | |
|---|---|
| Risk Index | Interpretation |
| ≤0.05 | low risk |
| 0.05–0.60 | moderate risk |
| >0.60 | high risk |

D. Software Performance

As demonstrated below, the Preterm Delivery Risk Assessment Software supplements the fFN ELISA results in a clinically useful manner. By combining patient history and symptom information with the fFN ELISA test results, the software is able to more accurately assess the risk of preterm delivery. The data presented above suggest that the software is more capable of discriminating those women truly at risk for preterm delivery: whereas the fFN ELISA test has relatively high false positive rates and low positive predictive value, the software test reduces false positive observations by over 50% and doubles predictive value of the positive result. The fFN ELISA test allowed clinicians to identify those patients not at risk for preterm delivery. Given the significant increase in relative risk and the risk classification of the software test, the clinician may now identify those women who are at risk for preterm delivery. This capability represents a new advance in the clinical management of women who are experiencing symptoms of preterm labor.

In particular, the performance of the Preterm Delivery Risk Assessment Software has been evaluated on 763 women experiencing at least one of the following symptoms of preterm labor:

1. Uterine contractions, with or without pain.
2. Intermittent lower abdominal pain, dull, low backache, pelvic pressure.
3. Bleeding during the second or third trimester.
4. Menstrual-like or intestinal cramping, with or without diarrhea.
5. Change in vaginal discharge--amount, color or consistency.
6. Not "feeling right".

All 763 women were tested for fFN using the Qualitative fFN ELISA test. Based solely on the ELISA test, 149 women tested positive for fFN of which only 20 (13.4%) delivered within 7 days and 25 (16.8%) delivered within 14 days.

The low positive predictive value of the fFN ELISA test is enhanced by the Preterm Delivery Risk Assessment Software, which combines the fFN ELISA result with other patient information.

Table 1 compares the performance of the Qualitative fFN ELISA Test with the Preterm Delivery Risk Assessment Software Test for predicting delivery before 35 weeks completed gestation. The number of false positive observations decreased from 105 to 42, or about 60%. The decrease in false positive results is accompanied by a corresponding increase in true negative results, from 584 for the fFN ELISA to 647 for the software test. Moreover, a reduction in false negative results was also observed, from 30 for the ELISA test to 25 for the software test. Accordingly, the sensitivity and the specificity of the ELISA test are augmented by the software from 59.5% to 66.2% and from 84.8% to 90.4%, respectively. The positive predictive nearly doubles, increasing from 29.5% to 53.9%, and both the odds ratio and relative risk are increased substantially.

TABLE 1

Performance comparison of Qualitative fFN ELISA Test and the Preterm Delivery Risk Assessment Software Test relative to risk of preterm delivery before 35 completed weeks of gestation. The Risk Assessment Software combines fFN ELISA Test results with patient history and symptom information to provide a more accurately assess risk of preterm delivery (before 35 completed weeks of gestation).

| MEASURE | QUAL fFN ELISA TEST | RISK ASSESSMENT SOFTWARE TEST |
|---|---|---|
| True Positive | 44 | 49 |
| False Positive | 105 | 42 |
| True Negative | 584 | 647 |
| False Negative | 30 | 25 |
| Sensitivity | 59.5% | 66.2% |
| Specificity | 84.8% | 96.3% |
| Pos PV | 29.5% | 53.9% |
| Neg PV | 95.1% | 96.3% |
| Odds Ratio | 8.2 | 30.2 |
| Relative Risk | 6.0 | 14.6 |

Table 2 compares the performance of the two tests relative to risk of preterm delivery within 7 days. The largest difference between the two tests is in the reduction of false positive test results of the software when compared to the ELISA test. The software decreased the number of false positive observations from 129 to 57, or about 56%. Accompanying this decrease in false positive results is the matching increasing in true negative results, from 611 to 683. The true positive and false negative results remained essentially unchanged. The sensitivity and specificity of the software test is much higher than the ELISA test. Compare the sensitivity of 91.3% for the software with 87.0% for the ELISA, and the specificity of 92.3% for the software with 92.3% for the ELISA. Furthermore, the software test doubles the positive predictive value, increasing form 13.4% to 26.9%. Finally, the odds ratio is quadrupled and the relative risk more than tripled by the software.

TABLE 2

Performance comparison of Quantitative fFN ELISA Test and the Preterm Delivery Risk Assessment Software Test relative to risk of preterm delivery within 7 days.

| MEASURE | QUAL fFN ELISA TEST | RISK ASSESSMENT SOFTWARE TEST |
|---|---|---|
| True Positive | 20 | 21 |
| False Positive | 129 | 57 |
| True Negative | 611 | 683 |
| False Negative | 3 | 2 |

TABLE 2-continued

Performance comparison of Quantitative fFN ELISA Test and the Preterm Delivery Risk Assessment Software Test relative to risk of preterm delivery within 7 days.

| MEASURE | QUAL fFN ELISA TEST | RISK ASSESSMENT SOFTWARE TEST |
|---|---|---|
| Sensitivity | 87.0% | 91.3% |
| Specificity | 82.6% | 92.3% |
| Pos PV | 13.4% | 26.9% |
| Neg PV | 99.5% | 99.7% |
| Odds Ratio | 31.6 | 125.8 |
| Relative Risk | 27.4 | 89.7 |

Table 3 compares the performance of the two test relative to risk of preterm delivery within 14 days. Once again, the software decreases false positive test results when compared to the ELISA test, from 124 to 55, or about 53%. This decrease in false positive results is matched by the corresponding increase in true negative results, from 609 to 678. The number of true positive and false negative results were unchanged. Whilst the sensitivity of the test was unaffected, the specificity of the test rose nearly 10 points, increasing from 83.1% to 92.5%. As seen before, the positive predictive value nearly doubled, increasing from 16.8% to 31.3%, and the odds ratio and relative risk increased substantially from 24.6 to 61.6 and from 20.7 to 44.7, respectively.

TABLE 3

Performance comparison of Qualitative fFN ELISA Test and the Preterm Delivery Risk Assessment Software Test relative to risk of preterm delivery within 14 days.

| MEASURE | QUAL fFN ELISA TEST | RISK ASSESSMENT SOFTWARE TEST |
|---|---|---|
| True Positive | 25 | 25 |
| False Positive | 124 | 55 |
| True Negative | 609 | 678 |
| False Negative | 5 | 5 |
| Sensitivity | 83.3% | 83.3% |
| Specificity | 83.1% | 92.5% |
| Pos PV | 16.8% | 31.3% |
| Neg PV | 99.2% | 99.3% |
| Odds Ratio | 24.6 | 61.6 |
| Relative Risk | 20.7 | 44.7 |

The following example is included for illustrative purposes only and are not intended to limit the scope of the invention.

EXAMPLE

Variable Selection and Development of Neural Nets for Predicting Pregnancy Related Events and Improvement of the Performance of Tests for Fetal Fibronectin The Fetal Fibronectin Enzyme Immunoassay (fFN ELISA) detects the presence or absence of fetal fibronectin (fFN) in cervicovaginal secretions (see, U.S. Pat. No. 5,468,619). Detection of fFN in cervicovaginal secretions of symptomatic pregnant women between 24 and 34 completed weeks gestation is associated with preterm delivery. This test is used to predict impending delivery within 7 or 14 days of sampling. For prediction of delivery within 14 days for sampling of fFN, the negative result is greater than 99% accurate. The positive result is more difficult to interpret, and the positive predictive value is less than 20%.

Neural networks were trained to assess the risk of preterm delivery using over 700 examples of pregnant women who were symptomatic for preterm delivery. Each example contained a multitude of information about that patient, including symptoms, reproductive history and other factors. Neural networks were trained to recognize complex patterns of interactions between these factors that indicate when a woman is at risk for preterm delivery. These neural networks are contained in the Preterm Delivery Risk Assessment software, which augments the fFN ELISA test result by decreasing false positive observations.

A. Variables

The following are variables based on patient input data. Neural networks using all or selected subsets of these variables may be generated. Combinations of at least three of these variables may be used in conjunction with decision-support systems, particularly neural nets to predict risk of preterm delivery or impending delivery. The inputs for the variables are either yes, no, no answer, or a text input, such as age. The variables, listed by type are as follows:

1 Age

Ethnic origin variables:
2 EthOrg1: Caucasian;
3 EthOrg2: Black;
4 EthOrg3: Asian;
5 EthOrg4: Hispanic;
6 EthOrg5: Native American; and
7 EthOrg6: Other than the above.

Marital status variables:
8 MarSt1: Single;
9 MarSt2: Married;
10 MarSt3: Divorced/Separated;
11 MarSt4: Widowed;
12 MarSt5: Living with partner; or
13 MarSt6: Other than those listed above.

Education variables:
14 Edu0: Unknown;
15 Edu1: <High School;
16 Edu2: High School Graduate; or
17 Edu3: College/trade.

Patient complaint variables:
18 PATIENT COMPLAINT #1 Patient has Uterine Contractions with or without pain;
19 PATIENT COMPLAINT #2 Patient has intermittent lower abdominal pain, dull, low backache, pelvic pressure;
20 PATIENT COMPLAINT #3 Patient has bleeding during the second or third trimester;
21 PATIENT COMPLAINT #4 Patient has menstrual-like or intestinal cramping;
22 PATIENT COMPLAINT #5 Patient has change in vaginal discharge or amount, color, or consistency; or
23 PATIENT COMPLAINT #6 Patient is not "feeling right".

Variables from physician tests and assessments:
24 Pooling refers to visual assessment to determine whether amniotic fluid has leaked into the vagina (see, e.g., Chapter 36, Section 18, p. 657 in *Maternal Fetal Medicine: Principle and Practice,* 2nd Edition, Creasy, R. F. et al., eds., W. B. Saunders & Co. (1989));
25 Ferning refers to the results of a test to detect the pattern formed when amniotic fluid is present in a cervical sample smeared on a clean slide and allowed to air dry (see, eq., Chapter 36, Section 18, p. 657 in *Maternal Fetal Medicine: Principle and Practice,* 2nd Edition, Creasy, R. F. et al., eds., W. B. Saunders & Co. (1989));
26 Nitrazine refers to results from a known test used to measure the pH of amniotic fluid that has leaked into the vagina (see, e.q., Chapter 36, Section 18, p. 657 in *Maternal Fetal Medicine: Principle and Practice,* 2nd Edition, Creasy, R. F. et al., eds., W. B. Saunders & Co. (1989));
27 estimated gestational based (EGA) on last period (LMP);
28 EGA by sonogram (SONO);
29 EGA by Best-EGA is the best of the EGA by SONO and EGA by LMP determined as follows:
if EGA by SONO is <13 weeks, then EGA best is EGA SONO;
if the difference by EGA by LMP and EGA by SONO is >2 weeks, then EGA best is EGA by SONO; otherwise EGA best is EGA by LMP;
30 EGA at Sampling refers to the EGA when fFN sampled;
31 CD INTERP, which refers to cervical dilatation (interpreted values—i.e. based on physicians estimates) where the number will be between 0 and 10 cm and is determined from the physicians response;
32 Gravity, which refers to the number of time woman has been pregnant;
33 Parity-term, which refers to the number of term births;
34 Parity-preterm, which refers to the number of preterm births;
35 Parity-abortions, which refers to the number of pregnancies ending in spontaneous or elective abortions;
36 Parity-living, which refers to the number of living children;
37 Sex within 24 hrs prior to sampling for fFN;
38 Vaginal bleeding at time of sampling;
39 Cervical consistency at time of sampling; and
40 UC INTERP, which refers to uterine contractions per hour as interpreted by the physician.

Complications
41 0 COMP No previous pregnancies;
42 1 COMP have had at least one previous pregnancy without complications;
43 2nd comp at least one preterm delivery (delivery prior to 35 weeks);
44 3rd comp at least one previous pregnancy with a premature rupture of membrane (PROM);
45 4th comp at least one previous delivery with incompetent cervix;
46 5 COMP at least on previous pregnancy with pregnancy induced hypertension (PIH)/preeclampsia;
47 6 COMP at least one previous pregnancy with spontaneous abortion prior to 20 weeks;
48 OTHER COMP at least one previous pregnancy with a complication not listed above; and
49 RESULT—fFN ELISA qualitative test result (if positive value is 1, if negative value is 0).

The variable selection protocol has been applied to these variables for selected outcomes, and the results are set forth below. Exemplary neural nets are provided.

B. A first set of neural networks demonstrating that the methods herein can be used to predict pregnancy related events

EGA1–EGA4

For these nets the preterm delivery defined as less than or equal to 34 weeks, 0 days. The other nets herein (described below) define preterm delivery as less than or equal 34 weeks, 6 days.

Data was collected from the over 700 test patients involved in a clinical trial of the assay described in U.S. Pat. No. 5,468,619. Variable selection was performed without fetal fibronectin (fFN) test data. The final networks, designate EGA1-EGA4 were trained with the variables set forth in the table below.

EGA1–EGA4 represent neural networks used for variable selection. For EGA1, the variable selection protocol was performed a network architecture with 8 inputs in the input layer, three processing elements in the hidden layer, and one output in the output layer. EGA2 is the same as EGA1, except that it is 9 inputs in the input layer.

EGA3 has 7 inputs in the input layer, three processing elements in the hidden layer, and one output in the output layer. EGA4 is the same as EGAL, except that it is 8 inputs in the input layer.

The variables selected are as follows:

| EGA1 | EGA2 | EGA3 | EGA4 |
|---|---|---|---|
| — | fFN | — | fFN |
| Ethnic Origin 1 (Caucasian) | | Ethnic Origin 4 (Hispanic) | |
| EGA Sonogram | | Marital Status 5 (living with partner) | |
| EGA Best (physician's determination of estimated gestational age) | | Marital Status 6 (other) | |
| EGA Sampling | | EGA Best | |
| Cervical dilation interpretation | | Cervical dilation interpretation | |
| Vaginal bleeding (at time of sampling) | | Vaginal bleeding (at time of sampling) | |
| 1 complications (prev. preg w/o complications) | | Other complications (prev. preg. w complications) | |
| Other complications (prev. preg. w complications) | | | |

EGA = estimated gestational age

Final Consensus Network Performance

| Net | TP | TN | FP | FN | SN | SP | PPV | NVP | OR |
|---|---|---|---|---|---|---|---|---|---|
| EGA1 | 35 | 619 | 92 | 17 | 67.3 | 87.0 | 27.6 | 97.3 | 6.0 |
| EGA2 | 37 | 640 | 71 | 15 | 71.2 | 90.0 | 34.3 | 97.7 | 7.9 |
| EGA3 | 36 | 602 | 109 | 16 | 69.2 | 84.7 | 24.8 | 97.4 | 5.1 |
| EGA4 | 32 | 654 | 57 | 20 | 61.5 | 92.0 | 36.0 | 87.0 | 8.9 |
| fFN | 31 | 592 | 119 | 21 | 59.6 | 83.3 | 20.7 | 96.6 | 7.3 |

EGA = estimated gestational age (less than 34 weeks); TP = true positives; TN = true negatives; FP = false positives; FN = false negatives; SN = sensitivity; SP = specificity;, PPV = positive predictive value; NPV = negative predictive value; OR = odds ratio (total number correct/total number correct answers); and fFN = the results from the ELISA assay for fFN.

The results show that the network EGA4, the neural net that includes seven patient variables and includes the fFN ELISA assay and that predicts delivery at less than 34 weeks, has far fewer false positives than the fFN ELISA assay. In addition, the number of false positives was reduced by 50%. Thus, incorporation of the fFN test into a neural net improved the performance of the fFN ELISA assay. All of the neural nets performed better than the fFN test alone.

Thus, the methods herein, can be used to develop neural nets, as well as other decision-support systems, that can be used to predict pregnancy related events.

C. Neural network prediction of delivery before 35 completed weeks of gestation -EGA5 and EGA6

The fFN-NET database was used for all the experiments; organization of variables and order of variables was the same as described herein. Two variable selection runs were performed on the training data to determine the important variables to be used for the consensus runs. In each of the runs the hidden layer contained 5 processing elements. This choice was based on the use of the variable selection process to determine the best size of the hidden layer. Variable selection was run with different numbers of hidden units in the neural network. The performance of the final selection of variables was compared for each different hidden layer configuration. Five hidden units were found to give the best performance. Each run used a partition of 5 and a consensus of 10 networks. The top 10 variables were examined during the run before a variable was selected to be in the selection. During these runs the biochemical test variable, fFN result, was not included in the possible variables for variable selection.

The resulting choices of variables were then re-evaluated using a consensus of 20 networks so that the two separate runs could be compared on an equal basis. Then the fFN result variable was added to the selected variables and the selections were re-evaluated using a consensus of 20 networks. This allowed the effect of the biochemical test on the performance to be determined. The final consensus training runs, using 8 networks, were made using all available data for training and the best performing set of variables from the above evaluations with the fFN result variable included.

1. Variable Selection

Using the same database described above for EGA1–EGA4, the variable selection protocol was applied as described above, except that the variable selection procedure was applied in the absence of the fFN test result. Since it is known that the results of this test are highly predictive of preterm or impending delivery, it was excluded from the variable selection procedure in order to eliminate its overriding influence, and to thereby select the important variables from among the other 48 variables.

Application of the variable selection procedure to the 48 variables resulted in selection of the following variables:
1. Ethnic Origin 1: Caucasian (i.e., yes or no);
2. Marital Status 5: living with partner (yes or no);
3. EGA by sonogram
4. EGA at sampling
5. estimated date of delivery by best
6. cervical dilatation (CM)
7. Parity-preterm
8. vaginal bleeding at time of sampling
9. cervical consistency at time of sampling; and
10. previous pregnancy without complication.

2. Neural Nets

Using these variables two consensus networks were trained. One, designated EGA5, was trained without including the results of the fFN ELISA test result, and the other, designated EGA6, was trained with the results of the fFN ELISA test result.

Figure 12:
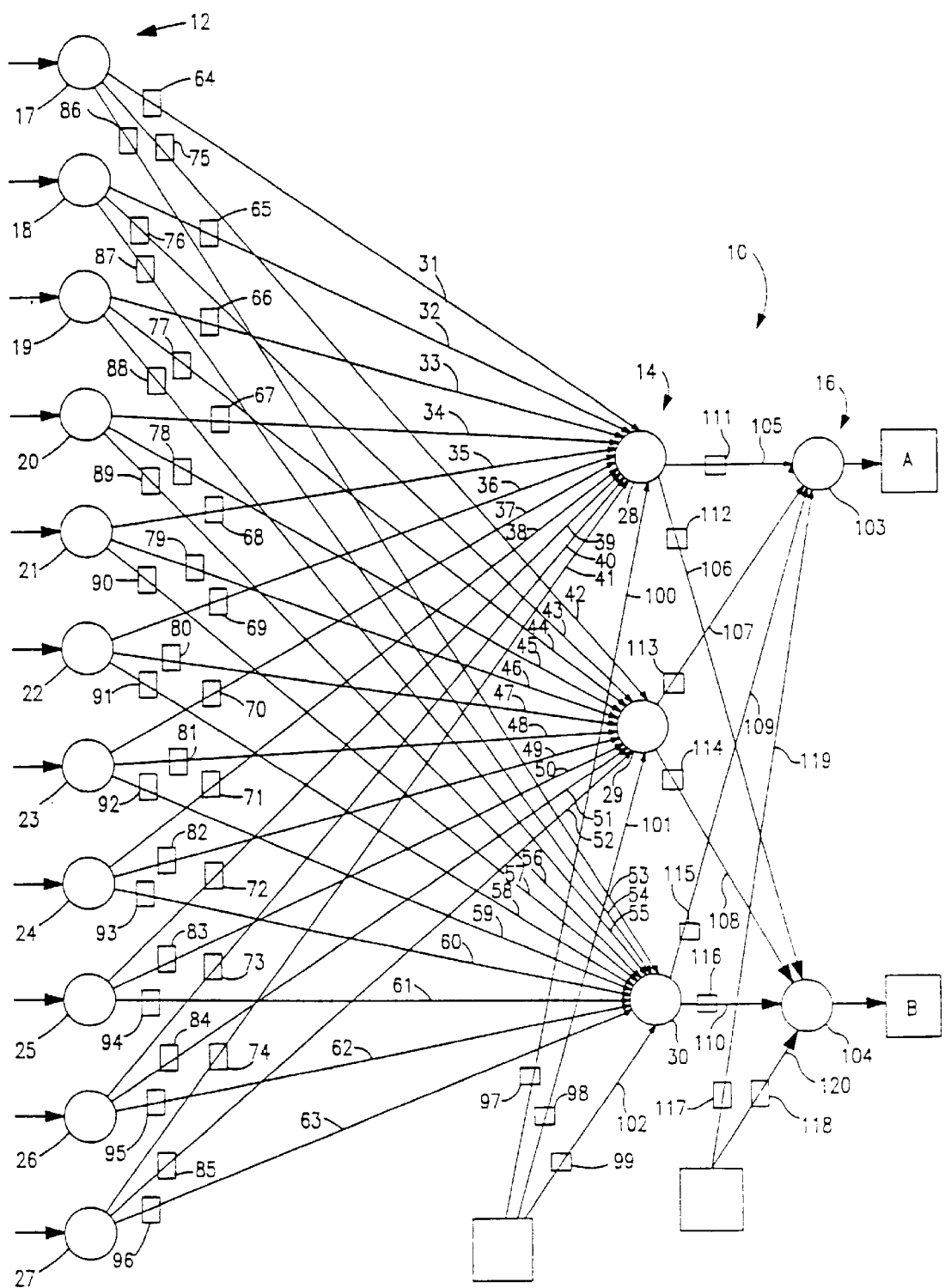
FIG. 12 is a schematic diagram of a neural network (EGA6) trained on clinical data of the form used for the consensus network of a plurality of neural networks.
Figure 14:
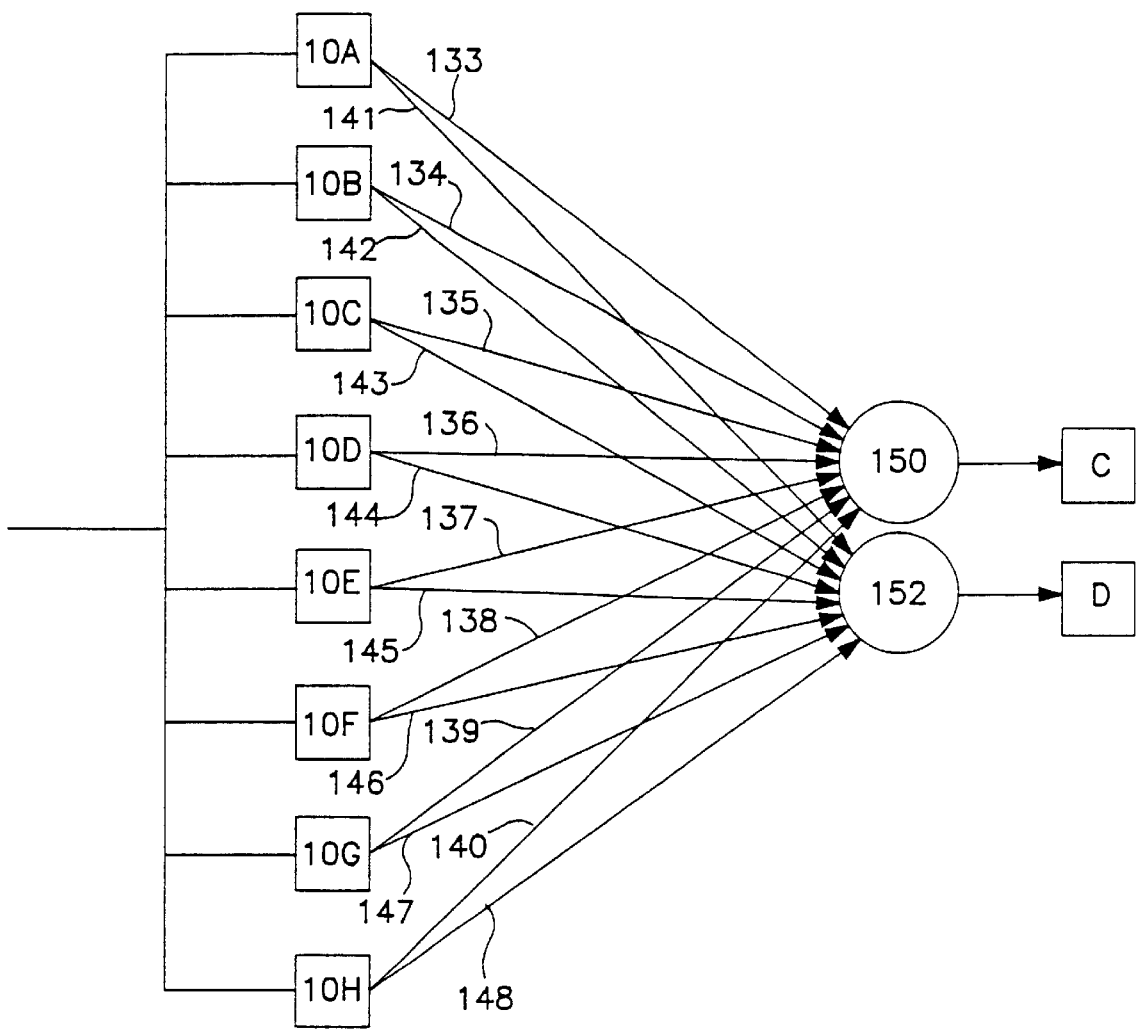
FIG. 14 is a schematic diagram of a consensus network of eight neural networks. A final indicator pair C, D is based on an analysis of a consensus of preliminary indicator pairs from a plurality, specifically eight, trained neural networks 10A–10H. Each preliminary indicator pair A, B is provided to one of two consensus processors 150, 152. via paths 133–140 and 141–148. The first consensus processor 150 processes all positive indicators. The second consensus processor 152 processes all negative indicators. Each consensus processor 150, 152 is an averager, i.e., it merely forms a linear combination, such as an average, of the collection of like preliminary indicator pairs A, B. The resultant confidence indicator pair is the desired result, where the inputs are the set of clinical factors for the patient under test.

FIG. 12, which represents EGA6, is a schematic diagram of an embodiment of one type of neural network 10 trained on clinical data of the form used for the consensus network (FIG. 14) of a plurality of neural networks. The structure is stored in digital form, along with weight values and data to be processed in a digital computer. This neural network 10 contains three layers, an input layer 12, a hidden layer 14 and an output layer 16. The input layer 12 has eleven input preprocessors 17–27, each of which is provided with a normalizer (not shown in the figure, see table below), which generates a mean and standard deviation value to weight the clinical factors and which are input into the input layer. The mean and standard deviation values are unique to the network training data. The input layer preprocessors 17–27 are each coupled to first and second and third processing elements 28, 29 and 30, of the hidden layer 14 via paths 31–41, 42–52 and 53–63 so that each hidden layer processing element 28, 29 and 30 receives a value or signal from each input preprocessor 17–27. Each path is provided with a unique weight based on the results of training on training data. The unique weights 64–74, 75–85, and 86–96 (see, also Table below) are non-linearly related to the output and are unique for each network structure and initial values of the training data. The final value of the weights are based on the initialized values assigned for network training. The combination of the weights that result from training constitute a functional apparatus whose description as expressed in weights produces a desired solution, or more specifically a risk assessment for preterm delivery before 35 weeks.

The hidden layer 14 is biased by bias weights 97, 98 and 99 provided via paths 100, 101, and 102 to the processing elements 28, 29 and 30. The output layer 16 contains two output processing elements 103, 104. The output layer 16 receives input from the hidden layer processing elements 28, 29 and 30 via paths 105–110. The output layer processing elements 103, 104 are weighted by weights 111–116. The output layer 16 is biased by bias weights 117, 118 provided via paths 119 and 120 to the processing elements 103 and 104.

The preliminary risk of delivery before 35 completed weeks of gestation is the output pair of values A and B from the two processing elements 103 and 104. The values are always positive between zero and one. One of the indicators is indicative of a risk of preterm delivery. The other is an indicator of the absence of such risk. While the output pair A, B provide generally valid indication of risk, a consensus network of trained neural networks provides a higher confidence index. EGA 6 contains 8 such trained neural networks.

The following tables set forth the values of the individual weights for each of the 8 consensus networks, designed EGA6_0 through EGA6_7.

| Input layer node/weight | hidden layer (nodes) 1st | 2nd | 3rd | output layer (nodes) 1st | 2nd |
|---|---|---|---|---|---|
| EGA 6_0 | | | | | |
| 0 | 0.412437 | −0.143143 | −1.885393 | −0.9598620 | 0.945025 |
| 1 | 2.041149 | −0.021533 | 0.162966 | −4.839373 | 4.875033 |
| 2 | 1.224530 | 0.971002 | −0.590964 | −2.524601 | 2.524054 |
| 3 | 0.575975 | −3.249891 | −2.814656 | 2.583483 | −2.561113 |
| 4 | 0.784864 | 0.600535 | −0.300794 | | |
| 5 | 1.075542 | 0.1601136 | 0.549237 | | |
| 6 | −1.047227 | 0.047396 | 0.905172 | | |
| 7 | −0.966051 | 0.163156 | 0.630888 | | |
| | −0.193761 | −0.149381 | 0.163185 | | |
| 9 | −0.680552 | −2.362585 | 1.365873 | | |
| 10 | 1.010706 | −3.633732 | −1.443890 | | |
| 11 | 1.728520 | −0.590057 | 0.878588 | | |
| EGA 6_1 | | | | | |
| 0 | 2.675421 | −0.552641 | 0.673642 | 0.183663 | 0.197713 |
| 1 | −1.181347 | 0.284937 | 0.720041 | −3.170281 | 3.095180 |
| 2 | −0.178288 | −1.102137 | 0.655263 | 3.795940 | −3.747696 |
| 3 | 1.048956 | −0.941387 | −1.733601 | −6.612447 | 6.498429 |
| 4 | 0.033454 | 0.927974 | 2.987905 | | |
| 5 | −1.161823 | 1.217736 | 1.014796 | | |
| 6 | 6.168329 | 2.549298 | −1.321217 | | |
| 7 | −1.560728 | −1.637513 | −1.160331 | | |
| 8 | 1.671384 | 3.395848 | −0.117778 | | |
| 9 | 0.416004 | 1.452099 | −0.246268 | | |
| 10 | −2.228914 | 1.834281 | 0.748248 | | |
| 11 | −3.687070 | 1.693113 | −0.492244 | | |
| EGA 6_2 | | | | | |
| 0 | −1.013347 | 1.392476 | 3.390216 | 1.093532 | −1.084186 |
| 1 | −3.020375 | 0.554074 | 2.172394 | −1.633913 | 1.632363 |
| 2 | −0.899928 | 1.928149 | 0.466793 | −3.099829 | 3.091530 |
| 3 | −8.108200 | 0.583508 | 0.030467 | −2.860816 | 2.845121 |
| 4 | 3.260629 | 9.249855 | 0.577971 | | |
| 5 | −0.567385 | 1.008019 | 0.196682 | | |
| 6 | −2.382355 | −2.942121 | 0.568323 | | |
| 7 | −1.996632 | −2.203792 | −0.852693 | | |
| 8 | 0.217054 | −0.230021 | −0.710703 | | |
| 9 | 0.380832 | −0.276078 | −1.551226 | | |
| 10 | 1.933148 | 0.603005 | −0.856832 | | |
| 11 | −1.922944 | −1.396864 | −2.356188 | | |
| EGA 6_3 | | | | | |
| 0 | 1.493395 | −2.294246 | 2.173191 | −1.417536 | 1.413825 |
| 1 | 3.959154 | 0.635345 | 0.976585 | −2.381441 | 2.355649 |
| 2 | 0.396474 | −1.310699 | 0.708136 | 2.652994 | −2.638396 |
| 3 | −0.404996 | −0.906109 | 1.164319 | −3.176520 | 3.136459 |
| 4 | −0.113969 | −0.611193 | −0.896189 | | |
| 5 | 0.665321 | −1.422789 | 0.184973 | | |
| 6 | 1.628547 | 2.765793 | 0.315556 | | |
| 7 | −0.673276 | 1.645794 | −0.975604 | | |
| 8 | −2.422190 | 1.272992 | 0.612878 | | |
| 9 | −1.494859 | 2.990876 | 0.002188 | | |
| 10 | −0.316486 | −0.614556 | −0.993159 | | |
| 11 | −3.208810 | −0.869353 | −3.219709 | | |
| EGA 6_4 | | | | | |
| 0 | 1.595199 | −1.400935 | −1.254950 | −1.033706 | 1.017989 |
| 1 | 1.597543 | 1.434936 | −1.886380 | −3.899452 | 3.915186 |
| 2 | 0.424391 | −0.524230 | 0.974168 | 2.759211 | −2.750812 |
| 3 | 1.340851 | 0.063071 | −5.226755 | −2.077351 | 2.087066 |
| 4 | 0.145379 | −3.090206 | −1.188423 | | |
| 5 | 0.569193 | −1.556114 | −1.835809 | | |
| 6 | 0.380544 | 3.770102 | −1.193652 | | |
| 7 | −0.414611 | 2.391878 | −0.326348 | | |
| 8 | 0.082901 | 0.821397 | −2.173482 | | |
| 9 | −0.893175 | 0.099641 | −1.615205 | | |
| 10 | 0.312568 | −0.034908 | −1.900884 | | |
| 11 | −1.068789 | 1.023022 | −1.393905 | | |
| EGA 6_5 | | | | | |
| 0 | 2.503198 | −2.428604 | −0.130730 | −2.186942 | 2.173897 |
| 1 | −2.192063 | −3.125744 | 3.638620 | −2.776665 | 2.660086 |
| 2 | 1.579702 | 0.833396 | 1.472541 | 2.737514 | −2.713886 |
| 3 | −0.067358 | 0.422544 | −1.196156 | −1.586596 | 1.647172 |
| 4 | 1.298254 | −3.568407 | −1.013145 | | |
| 5 | 1.992165 | −3.716873 | −0.868908 | | |
| 6 | −4.089348 | 2.595805 | 3.020147 | | |
| 7 | −2.734360 | 2.001578 | −0.018092 | | |
| 8 | −1.668519 | −0.383253 | −3.587072 | | |
| 9 | −1.886910 | 0.268403 | −0.229832 | | |
| 10 | −1.519840 | −1.147216 | 1.671855 | | |
| 11 | −1.200146 | 3.289453 | −4.163397 | | |
| EGA 6_6 | | | | | |
| 0 | −1.443015 | 0.865813 | 0.382970 | −2.388151 | 2.408045 |
| 1 | −1.582839 | 0.593947 | 0.830775 | 4.015757 | −4.056962 |
| 2 | −1.119793 | −0.355416 | 0.803208 | −2.574057 | 2.594654 |
| 3 | 2.549989 | 0.295836 | 0.454763 | −3.381956 | 3.430132 |
| 4 | −3.080358 | −3.033361 | 1.023391 | | |
| 5 | −2.302934 | 0.508087 | −0.703378 | | |
| 6 | −0.040867 | −2.352165 | −1.982702 | | |
| 7 | 1.082370 | 3.718414 | −4.853944 | | |
| 8 | −0.564883 | −4.419714 | −2.375676 | | |
| 9 | 0.953993 | −2.047337 | −0.481060 | | |
| 10 | −1.062311 | 0.216755 | −2.037935 | | |
| 11 | 1.488106 | −3.616466 | −0.630520 | | |

-continued

| Input layer | hidden layer (nodes) | | | output layer (nodes) | |
|---|---|---|---|---|---|
| node/weight | 1st | 2nd | 3rd | 1st | 2nd |
| EGA 6_7 | | | | | |
| 0 | 1.622433 | 1.633779 | −3.852473 | −0.748768 | 0.742163 |
| 1 | 0.043906 | −0.351661 | −2.431170 | −3.003003 | 2.983215 |
| 2 | 0.732213 | −0.661362 | −0.746753 | −2.218790 | 2.184970 |
| 3 | −2.027060 | 1.301339 | −1.768983 | 3.052581 | −3.004828 |
| 4 | 1.521622 | 1.790975 | −0.154270 | | |
| 5 | 1.677837 | −0.625462 | 0.730582 | | |
| 6 | −1.347791 | −4.165056 | −0.685942 | | |
| 7 | −1.774773 | 5.494371 | 1.034300 | | |
| 8 | −0.827799 | 1.789396 | 0.538103 | | |
| 9 | −0.509971 | −0.183482 | 1.543398 | | |
| 10 | 0.605369 | 2.345229 | 1.277570 | | |
| 11 | 0.691960 | −3.950886 | 2.871648 | | |

The EGA6 preprocessing information is the same for each of the 8 neural networks in the consensus. The input is preprocessed by subtracting the mean value and dividing by the standard deviation.

| Node | Mean | Standard Deviation |
|---|---|---|
| 1 | 0.399738 | 0.490166 |
| 2 | 0.011796 | 0.108036 |
| 3 | 30.593335 | 4.979660 |
| 4 | 30.709605 | 5.405745 |
| 5 | 30.278038 | 2.976036 |
| 6 | 0.490092 | 0.667659 |
| 7 | 0.178244 | 0.471996 |
| 8 | 0.198946 | 0.508406 |
| 9 | 1.823197 | 0.757205 |
| 10 | 0.399738 | 0.490166 |
| 11 | 0.195282 | 0.396677 |

EGA5 is a set of 8 consensus networks trained similarly to EGA6, except that the input variables did not include the variable representing the result of the fFN ELISA test. This network can be used as a point of care application to give immediate result to the clinician rather than the 24 to 48 hours required to process the fFN sample.

D. Neural network prediction of risk of delivery within 7 days—EGAD7 and EGAD7F

1. Variable Selection

Using the same database described above for EGA1–EGA6, the variable selection protocol was applied to prediction of the risk for delivery within 7 days of sampling for the fFN test. As noted above for EGA5 and EGA6, the variable selection procedure was applied in the absence of the fFN test result. Application of the variable selection procedure to the 48 variables resulted in selection of the following variables:
1. Ethnic Origin 1: Caucasian (i.e., yes or no);
2. Uterine contractions with or without pain (i.e., yes or no);
3. Parity-abortions;
4. Vaginal bleeding at time of sampling;
5. Uterine contractions per hour;
6. No previous pregnancies.

2. Neural Nets

Using these variables two consensus networks were trained. One, designated EGAD7 was trained without including the results of the fFN ELISA test result, and the other, designated EGAD7f, was trained with the results of the fFN ELISA test result.

Figure 13:
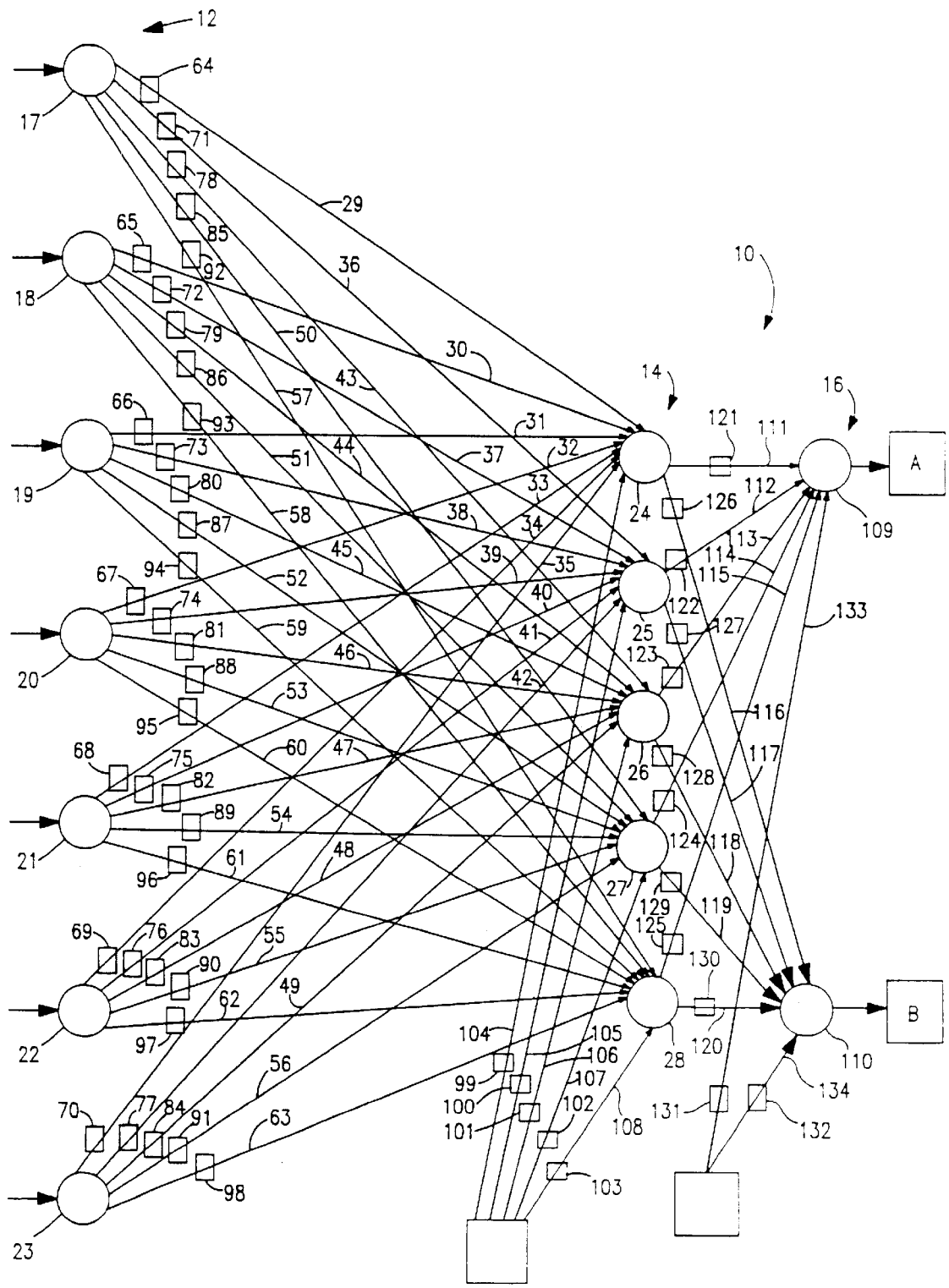
FIG. 13 is a schematic diagram of a neural network, such as EGAD7f and EGAD14f, trained on clinical data of the form used for the consensus network of a plurality of neural networks.

FIG. 13, which represents EGA7f, is a schematic diagram of an embodiment of the neural network 10 trained on clinical data of the form used for the consensus network (FIG. 14) of a plurality of neural networks. The structure is stored in digital form, along with weight values and data to be processed in a digital computer. This neural network 10 contains three layers, an input layer 12, a hidden layer 14 and an output layer 16. The input layer 12 has seven input preprocessors 17–23, each of which is provided with a normalizer (not shown in the figure, see table below) which generates a mean and standard deviation value to weight the clinical factors which are input into the input layer. The mean and standard deviation values are unique to the network training data. The input layer preprocessors 17–23 are each coupled to first, second, third, fourth and fifth processing elements 24–28, respectively, of the hidden layer 14 via paths 29–35, 36–42, 43–49, 50–56, and 57–63 so that each hidden layer processing element 24–28, receives a value or signal from each input preprocessor 17–23. Each path is provided with a unique weight based on the results of training on training data. The unique weights 64–70, 71–77, 78–84, 85–91 and 92–98 (see, also Table below) are non-linearly related to the output and are unique for each network structure and initial values of the training data. The final value of the weights are based on the initialized values assigned for network training. The combination of the weights that result from training constitute a functional apparatus whose description as expressed in weights produces a desired solution, or more specifically a risk assessment of delivery within 7 days of sampling for the fFN ELISA test.

The hidden layer 14 is biased by bias weights 99, 100, 101, 102 and 103 provided via paths 104, 105, 106, 107 and 108 to the processing elements 24, 25, 26, 27 and 28. The output layer 16 contains two output processing elements 109, 110. The output layer 16 receives input from the hidden layer processing elements 24–28 via paths 111–120. The output layer processing elements 109, 110 are weighted by weights 121–130. The output layer 16 is biased by bias weights 131, 132 provided via paths 133 and 134 to the processing elements 109 and 110.

The preliminary risk of delivery within 7 days from sampling for the fFN ELISA test is the output pair of values A and B from the two processing elements 109 and 110. The values are always positive between zero and one. One of the indicators is indicative of a risk of delivery within 7 days. The other is an indicator of the absence of such risk. While the output pair A, B provide generally valid indication of risk, a consensus network of trained neural networks provides a higher confidence index. EGAD7f contains 8 such trained neural networks.

The following tables set forth the values of the individual weights for each of the 8 consensus networks, designated EGAD7f0 through EGAD7f7:

| Input layer node/ weight | hidden layer (nodes) | | | | | output layer (nodes) | |
|---|---|---|---|---|---|---|---|
| | 1st | 2nd | 3rd | 4th | 5th | 1st | 2nd |
| EGAD7f0 | | | | | | | |
| 0 | −0.204716 | 1.533574 | 1.452831 | 0.129981 | −1.784807 | 0.854229 | −0.883808 |
| 1 | −1.843673 | 1.957059 | −2.668371 | −0.551016 | 1.505628 | −5.294533 | 5.303048 |
| 2 | −1.324609 | 0.258418 | −1.280479 | −0.476101 | 0.827188 | −7.468771 | 7.514580 |
| 3 | −1.281561 | 1.697443 | 6.865219 | 4.212538 | −1.953753 | −5.082050 | 5.003566 |
| 4 | −1.159086 | −0.345244 | −4.689749 | −0.406485 | 1.027280 | 4.014138 | −4.006929 |
| 5 | −2.042978 | 0.182091 | 2.612433 | 2.399196 | −1.397453 | −4.105859 | 4.105161 |
| 6 | −4.076656 | 1.416529 | 0.979842 | −2.589272 | 0.068466 | | |
| 7 | −0.499705 | −1.383732 | −2.411544 | 0.173131 | −1.919889 | | |
| EGAD7f1 | | | | | | | |
| 0 | 1.522090 | 6.396365 | 1.750606 | 0.650769 | 0.673423 | 0.282480 | −0.222861 |
| 1 | 1.930314 | 0.027271 | 0.386927 | 1.602559 | 3.495371 | −5.126995 | 4.888618 |
| 2 | 1.578675 | −0.445222 | 0.352425 | 1.305894 | 1.703156 | −3.751147 | 3.752025 |
| 3 | 1.821893 | 6.258497 | 1.140159 | 1.363783 | −0.717021 | −5.496184 | 5.687717 |
| 4 | −4.599618 | 0.218248 | 0.385593 | 0.945824 | 0.644622 | 7.713794 | −8.054935 |
| 5 | −2.755846 | −1.799000 | 2.162089 | 1.730335 | −0.388646 | −3.429169 | 3.706028 |
| 6 | 0.524701 | 1.669467 | 1.741620 | 3.956515 | 4.717868 | | |
| 7 | −2.089663 | −0.190423 | −1.736970 | 0.085315 | −1.010295 | | |
| EGAD7f2 | | | | | | | |
| 0 | 0.554749 | 4.029042 | 1.041783 | 0.687361 | 2.078268 | 0.718456 | −0.756554 |
| 1 | 0.314365 | −1.614025 | 4.560114 | −0.197290 | 2.352322 | 3.339842 | −3.185465 |
| 2 | −1.992577 | −1.810437 | 2.067243 | −0.021868 | 0.041441 | −5.596330 | 5.470991 |
| 3 | −4.762585 | −6.021220 | 3.627642 | 3.505088 | 1.221308 | 0.815486 | −0.906961 |
| 4 | 8.422636 | −1.088322 | −1.229308 | −2.513499 | 0.344056 | −4.076351 | 4.165072 |
| 5 | −0.547021 | −6.256763 | 1.108255 | 1.341978 | −0.074222 | −7.385492 | 7.372295 |
| 6 | 0.581056 | −2.916328 | 0.639607 | 0.894802 | 2.365492 | | |
| 7 | 1.260577 | −1.583044 | 0.882731 | −1.113407 | −1.657523 | | |
| EGAD7f3 | | | | | | | |
| 0 | 1.258939 | 0.778115 | 1.117508 | −5.828234 | 3.275221 | −0.174440 | 0.260818 |
| 1 | 1.038074 | 0.395096 | −1.080656 | −0.580291 | −1.077984 | −6.546609 | 6.515666 |
| 2 | −2.174144 | 0.453939 | −0.677622 | −1.330231 | −0.383479 | −8.061748 | 8.067432 |
| 3 | 0.608410 | 2.262108 | 9.263388 | 4.024162 | 0.949009 | 4.938700 | −5.060233 |
| 4 | 1.443697 | −1.530076 | −0.812837 | 1.549062 | −1.594324 | 5.420476 | −5.517191 |
| 5 | −1.437676 | 0.749049 | 5.493512 | −2.797146 | −2.056666 | −5.085781 | 5.127757 |
| 6 | 0.778191 | 1.397835 | −3.635368 | 2.191902 | −2.403500 | | |
| 7 | −1.776540 | −0.675587 | 0.115711 | 0.388203 | −1.363938 | | |
| EGAD7f4 | | | | | | | |
| 0 | −1.839879 | 0.255905 | 3.002103 | 0.886848 | −0.485949 | −1.461668 | 1.340040 |
| 1 | −1.335228 | −3.428058 | 0.665937 | −1.072765 | −0.372897 | −1.862627 | 1.815599 |
| 2 | 0.062547 | 0.489211 | 0.946443 | −3.642373 | 3.973801 | 5.835287 | −5.699555 |
| 3 | 1.888678 | 1.928167 | 4.900952 | 1.928106 | −1.866227 | −5.463729 | 5.463984 |
| 4 | −5.217631 | −1.441138 | −4.114171 | 0.629958 | −1.615146 | −5.726771 | 5.763464 |
| 5 | −0.631546 | 1.735842 | 1.158419 | 0.638580 | −3.276926 | −7.193156 | 7.177080 |
| 6 | −3.109977 | −0.377960 | 1.372646 | 2.625961 | −1.700064 | | |
| 7 | −0.070132 | 1.763962 | −2.234798 | −1.165563 | −1.845262 | | |
| EGAD7f5 | | | | | | | |
| 0 | −1.456277 | 1.321048 | 1.214385 | 0.069355 | −0.206125 | −1.581118 | 1.811097 |
| 1 | 1.988970 | −2.788917 | 1.700144 | −3.790842 | 0.760984 | −3.282460 | 2.842431 |
| 2 | −0.889522 | −1.748239 | 0.798888 | −0.481237 | 0.248333 | −6.391959 | 6.435954 |
| 3 | 15.258006 | 0.809204 | 4.071811 | −3.751193 | −6.873492 | −6.817300 | 6.829902 |
| 4 | −18.202002 | −2.000871 | 0.021785 | 0.812317 | 0.713510 | 6.157183 | −6.412641 |
| 5 | 0.440615 | −0.470067 | −1.578267 | −0.216803 | −3.315356 | −7.015062 | 6.902892 |
| 6 | −1.931575 | 0.510900 | 1.162408 | −2.528233 | 1.405955 | | |
| 7 | −3.758462 | −0.570789 | −6.338710 | 0.877703 | −0.985724 | | |
| EGAD7f6 | | | | | | | |
| 0 | 1.512437 | −0.333348 | −0.557454 | −0.790704 | 0.049061 | −0.918761 | 0.804829 |
| 1 | −0.704182 | −0.032274 | −3.201322 | −0.966885 | −0.213225 | −2.987857 | 2.999401 |
| 2 | 0.443652 | −0.736894 | −0.713164 | −0.709163 | −0.725865 | −5.682138 | 5.675150 |
| 3 | 2.734173 | 0.555570 | −2.071605 | 7.636067 | −7.109310 | 4.989255 | −4.851893 |
| 4 | −4.066469 | −0.039688 | 0.313027 | −0.265136 | 0.152398 | −4.107172 | 4.101486 |
| 5 | 0.943337 | −0.658673 | −0.079748 | 3.091015 | −5.459067 | −5.247225 | 5.231175 |
| 6 | −0.211375 | 0.247671 | −2.400778 | 2.663087 | −1.717437 | | |
| 7 | −1.291067 | −4.507938 | 1.526173 | −0.139780 | −0.451653 | | |

-continued

| Input layer node/ weight | hidden layer (nodes) | | | | | output layer (nodes) | |
|---|---|---|---|---|---|---|---|
| | 1st | 2nd | 3rd | 4th | 5th | 1st | 2nd |
| EGAD7f7 | | | | | | | |
| 0 | 0.580523 | 0.319374 | −0.660897 | 1.072931 | −0.522045 | −0.833235 | 1.016355 |
| 1 | 0.432923 | 3.916608 | 0.386343 | −1.324510 | −1.566712 | −4.472839 | 4.433871 |
| 2 | −0.312324 | 3.099275 | 0.344633 | −3.254393 | −1.081114 | −4.873536 | 4.919722 |
| 3 | 4.019378 | −5.440501 | −9.105190 | 1.955846 | −2.152612 | 4.971172 | −5.215318 |
| 4 | −0.355344 | 0.495595 | 0.543102 | −2.001959 | −0.989721 | −3.436097 | 3.478752 |
| 5 | −1.585942 | −3.885213 | −2.778485 | 1.068593 | −1.697807 | −4.098137 | 4.165162 |
| 6 | −0.209687 | −0.646458 | −2.399903 | 0.177487 | 2.339257 | | |
| 7 | −8.951553 | −1.471208 | 0.725651 | −2.732204 | 1.538870 | | |

The EGAD7F preprocessing information is the same for each of the 8 neural networks in the consensus. The input in preprocessed by subtracting the mean value and dividing by the standard deviation.

| Node | Mean | Standard Deviation |
|---|---|---|
| 1 | 0.399738 | 0.490166 |
| 2 | 0.517693 | 0.500015 |
| 3 | 0.621232 | 1.030720 |
| 4 | 0.198946 | 0.508406 |
| 5 | 2.144928 | 2.291734 |
| 6 | 0.281782 | 0.450163 |
| 7 | 0.195282 | 0.396677 |

EGAD7 is a set of 8 consensus networks trained similarly to EGAD7f, except that the input variables did not include the variable representing the result of the fFN ELISA test. This network can be used as a point of care application to give immediate result to the clinician rather than the 24 to 48 hours required to process the fFN sample.

E. Neural network prediction of risk of delivery within 14 days—EGAD14f and EGAD14

1. Variable Selection

Using the same database described above for EGA1–EGAD7, the variable selection protocol was applied to prediction of the risk for delivery within 14 days of sampling for the fFN test. As noted above for EGA5, EGA6 and EGAD7, the variable selection procedure was applied in the absence of the fFN test result. Application of the variable selection procedure to the 48 variables resulted in election of the following variables:
1. Ethnic Origin 4: Hispanic (i.e., yes or no);
2. Marital Status 5: living with partner;
3. Uterine contractions with or without pain (i.e., yes or no);
4. Cervical dilatation;
5. Uterine contractions per hour;
6. No previous pregnancies.

2. Neural Nets

Using these variables two consensus networks were trained. One, designated EGAD14 was trained without including the results of the fFN ELISA test result, and the other, designated EGAD14f, was trained with the results of the fFN ELISA test result.

FIG. 13, which represents EGAD14f (as well as EGAD7f), is a schematic diagram of an embodiment of the neural network 10 trained on clinical data of the form used for the consensus network (FIG. 14) of a plurality of neural networks. The structure is stored in digital form, along with weight values and data to be processed in a digital computer. This neural network 10 contains three layers, an input layer 12, a hidden layer 14 and an output layer 16. The input layer 12 has seven input preprocessors 17–23, each of which is provided with a normalizer (not shown in the figure, see Table, below) which generates a mean and standard deviation value to weight the clinical factors which are input into the input layer. The mean and standard deviation values are unique to the network training data. The input layer preprocessors 17–23 are each coupled to first, second, third, fourth and fifth processing elements 24–28, respectively, of the hidden layer 14 via paths 29–35, 36–42, 43–49, 50–56, and 57–63 so that each hidden layer processing element 24–28, receives a value or signal from each input preprocessor 17–23. Each path is provided with a unique weight based on the results of training on training data. The unique weights 64–70, 71–77, 78–84, 85–91 and 92–98 (see, also Table below) are non-linearly related to the output and are unique for each network structure and initial values of the training data. The final value of the weights are based on the initialized values assigned for network training. The combination of the weights that result from training constitute a functional apparatus whose description as expressed in weights produces a desired solution, or more specifically a risk assessment of delivery within 14 days of sampling for the fFN ELISA test.

The hidden layer 14 is biased by bias weights 99, 100, 101, 102 and 103 provided via paths 104, 105, 106, 107 and 108 to the processing elements 24, 25, 26, 27 and 28. The output layer 16 contains two output processing elements 109, 110. The output layer 16 receives input from the hidden layer processing elements 24–28 via paths 111–120. The output layer processing elements 109, 110 are weighted by weights 121–130. The output layer 16 is biased by bias weights 131, 132 provided via paths 133 and 134 to the processing elements 109 and 110.

The preliminary risk of delivery within 14 days from sampling for the fFN ELISA test is the output pair of values A and B from the two processing elements 109 and 110. The values are always positive between zero and one. One of the indicators is indicative of a risk of delivery within 14 days. The other is an indicator of the absence of such risk. While the output pair A, B provide generally valid indication of risk, a consensus network of trained neural networks provides a higher confidence index. EGAD14f contains 8 such trained neural networks.

The following tables set forth the values of the individual weights for each of the 8 consensus networks, designed EGAD14f0 through EGAD14f7.

| Input layer node/ | hidden layer (nodes) | | | | | output layer (nodes) | |
|---|---|---|---|---|---|---|---|
| weight | 1st | 2nd | 3rd | 4th | 5th | 1st | 2nd |
| EGAD14f0 | | | | | | | |
| 0 | −0.191126 | 1.174059 | 0.810632 | 0.148573 | −2.437188 | 0.106355 | −0.108766 |
| 1 | −2.921661 | −0.713076 | 1.312931 | 10.427816 | 1.824513 | −2.220130 | 2.198498 |
| 2 | −0.848702 | 1.614504 | 2.640692 | −0.445807 | 1.218097 | −2.016395 | 2.005455 |
| 3 | −1.008667 | 0.138305 | 1.372127 | 0.788516 | −3.114650 | −4.365818 | 4.349520 |
| 4 | −1.422990 | −1.517308 | −1.632533 | −3.146550 | 0.256047 | 2.291882 | −2.293527 |
| 5 | −2.588523 | −0.733381 | 0.992748 | 1.482687 | 1.197727 | −4.864353 | 4.861522 |
| 6 | −3.611756 | −2.669159 | 3.364100 | −1.806442 | 0.833890 | | |
| 7 | −0.516151 | −2.104245 | −2.052761 | −0.615030 | −1.621589 | | |
| EGAD14f1 | | | | | | | |
| 0 | 0.396502 | 2.426709 | 0.752911 | 1.549394 | −0.064008 | −0.285667 | 0.714618 |
| 1 | 1.248711 | 2.179334 | −0.016570 | −0.040113 | 2.457661 | −3.745954 | 3.884410 |
| 2 | 1.912210 | 0.937177 | −1.742286 | −2.094312 | −1.165847 | −4.912591 | 4.966647 |
| 3 | −1.018760 | −1.087528 | −0.344108 | 0.384237 | −1.077692 | −7.433263 | 7.309962 |
| 4 | 1.090578 | −2.229295 | −0.890326 | −1.334206 | 0.822185 | 2.080292 | −2.595363 |
| 5 | 1.399831 | −5.077936 | −0.600345 | 4.128439 | −1.715393 | 5.481619 | −5.611861 |
| 6 | 2.241531 | −4.673233 | −0.209741 | 2.954158 | −4.565109 | | |
| 7 | 0.077090 | −0.194145 | −4.391311 | 3.250038 | −2.360049 | | |
| EGAD14f2 | | | | | | | |
| 0 | 0.286926 | 1.855804 | 0.103985 | −2.590399 | 2.265841 | 1.540065 | −1.592696 |
| 1 | 1.928731 | 0.410516 | −2.015740 | 1.017801 | 2.088775 | 2.433105 | −2.545955 |
| 2 | −0.666312 | −1.178337 | 1.227737 | −1.471309 | 1.922938 | −4.736276 | 4.903823 |
| 3 | −2.716156 | −2.328632 | −0.566546 | 0.854688 | −0.448565 | −2.220462 | 2.268171 |
| 4 | 0.654814 | −0.197945 | −2.256156 | −0.410249 | −0.792705 | −4.049918 | 4.142265 |
| 5 | −2.004537 | −3.451720 | 3.311102 | 1.787226 | −0.682330 | −3.930044 | 4.036821 |
| 6 | −0.947058 | −1.898302 | −0.131517 | 4.187262 | 2.272720 | | |
| 7 | 0.485620 | −0.138471 | 1.038285 | −1.245135 | −6.442445 | | |
| EGAD14f3 | | | | | | | |
| 0 | 1.199346 | 1.135219 | 2.839737 | −4.673778 | 2.903983 | −0.702760 | 0.935822 |
| 1 | −1.274101 | 1.559637 | 1.386395 | −0.042351 | −0.874145 | −3.244763 | 3.144603 |
| 2 | −0.353335 | 0.325171 | −1.677620 | −0.793429 | 0.788584 | −4.933673 | 4.849451 |
| 3 | −0.678281 | −2.157454 | −3.084480 | 1.009661 | 0.327746 | 3.306738 | −3.432135 |
| 4 | 1.116566 | 0.128203 | −2.188180 | 2.315793 | −1.815492 | 4.993960 | −5.098751 |
| 5 | −1.277371 | −0.415757 | −0.080374 | −0.694424 | −1.022831 | −4.266839 | 4.064770 |
| 6 | −4.836841 | 3.738553 | −0.703345 | 0.271620 | −0.626113 | | |
| 7 | −0.953257 | −0.463343 | 1.314770 | −0.196871 | −2.372877 | | |
| EGAD14f4 | | | | | | | |
| 0 | −1.810913 | −0.014885 | 0.167362 | −2.605120 | −0.205378 | −0.681096 | 0.709641 |
| 1 | 5.080080 | 1.259709 | 0.430446 | 0.680130 | −3.098744 | −3.611765 | 3.644697 |
| 2 | −0.414857 | −0.328851 | −0.335724 | 5.756228 | 1.904646 | 4.377642 | −4.419249 |
| 3 | 0.525909 | 1.767786 | −0.375093 | 1.041263 | −0.566611 | −6.720907 | 6.647904 |
| 4 | −7.166096 | −0.912267 | −1.948366 | −1.117219 | −1.237101 | −2.355787 | 2.337121 |
| 5 | −4.340267 | −0.345630 | −0.077869 | 3.853568 | −2.550077 | −2.249878 | 2.171079 |
| 6 | −2.586306 | −3.315458 | 0.378838 | 5.812339 | −3.619375 | | |
| 7 | 0.213139 | −1.546969 | −10.991954 | −1.186517 | −0.502957 | | |
| EGAD14f5 | | | | | | | |
| 0 | −2.439228 | 0.954525 | 1.242215 | −27.696498 | 0.322283 | −2.017057 | 2.095211 |
| 1 | 1.998281 | 1.928331 | 0.638520 | −1.415280 | 1.871968 | 6.487561 | −6.308325 |
| 2 | −0.869648 | −0.994059 | 0.768856 | 0.368344 | 1.457719 | −4.867902 | 4.744858 |
| 3 | 0.295868 | −0.257773 | 1.422994 | 0.033843 | −4.658167 | −2.392888 | 2.192236 |
| 4 | −1.800394 | −2.612705 | −1.668799 | 51.649234 | −0.537556 | 1.222661 | −1.270161 |
| 5 | 0.992302 | −0.938952 | 1.104910 | 3.731820 | 1.651959 | −1.649461 | 1.594009 |
| 6 | −1.787379 | −1.045545 | 2.711432 | 0.288323 | −0.572490 | | |
| 7 | −0.374909 | −0.877122 | −1.918442 | 214.812434 | −1.773228 | | |
| EGAD14f6 | | | | | | | |
| 0 | 3.984308 | −0.300188 | 6.132831 | 1.776838 | 1.182643 | −0.141300 | −0.062816 |
| 1 | −2.478863 | 0.891740 | −0.185527 | −0.442487 | 1.045499 | −5.041497 | 4.985260 |
| 2 | 0.389668 | 0.650328 | −289.318971 | 0.651142 | 0.169117 | −7.230831 | 7.280185 |
| 3 | 0.370846 | 0.503667 | 21.787679 | 1.820010 | −0.802930 | 2.464335 | −2.250474 |
| 4 | −0.950033 | −0.054657 | 0.942573 | −1.024688 | −1.842654 | 2.637713 | −2.636534 |
| 5 | 3.200645 | 0.464231 | 0.728644 | 1.784671 | −5.371345 | −3.675622 | 3.704625 |
| 6 | 0.647747 | 2.560388 | −0.798268 | 3.237414 | −4.493387 | | |
| 7 | −1.276096 | −1.593493 | 66.059880 | 0.493228 | −0.126844 | | |

-continued

| Input layer node/ weight | hidden layer (nodes) | | | | | output layer (nodes) | |
|---|---|---|---|---|---|---|---|
| | 1st | 2nd | 3rd | 4th | 5th | 1st | 2nd |
| EGAD14f7 | | | | | | | |
| 0 | 0.888004 | 0.521346 | −0.513845 | 0.767983 | −0.956920 | −1.088033 | 1.264836 |
| 1 | 0.191409 | 1.634987 | −0.771837 | −2.402982 | −1.003714 | −4.407106 | 4.589468 |
| 2 | 2.233326 | 0.767802 | −10.205298 | 0.362276 | 0.797006 | −4.385751 | 4.466996 |
| 3 | −0.588252 | −5.586697 | 0.233547 | 0.586147 | 1.589040 | 5.286517 | −5.562157 |
| 4 | −1.544910 | −0.829764 | 0.624734 | −5.119879 | −0.276545 | −0.907527 | 0.809701 |
| 5 | −0.361805 | 0.397313 | −1.973167 | −2.953926 | −0.614287 | −5.146765 | 5.284392 |
| 6 | −0.136039 | −1.488352 | −3.541771 | 3.717852 | −1.091340 | | |
| 7 | −8.058644 | −1.997797 | 1.520159 | −0.638158 | 1.013775 | | |

The EGAD14F preprocessing information is the same for each of the 8 neural networks in the consensus. The input is preprocessed by subtracting the mean value and dividing by the standard deviation.

| Node | Mean | Standard Deviation |
|---|---|---|
| 1 | 0.152031 | 0.359287 |
| 2 | 0.91796 | 0.108036 |
| 3 | 0.517693 | 0.500015 |
| 4 | 0.490092 | 0.667659 |
| 5 | 2.144928 | 2.291734 |
| 6 | 0.281782 | 0.450163 |
| 7 | 0.195282 | 0.396677 |

EGAD14 is a set of 8 consensus networks trained similarly to EGAD14f, except that the input variables did not include the variable representing the result of the fFN ELISA test. This network can be used as a point of care application to give immediate result to the clinician rather than the 24 to 48 hours required to process the fFN sample.

Since modifications will be apparent to those of skill in this art, it is intended that this invention be limited only by the scope of the appended claims.

What is claimed:

1. A computer-based method of assessment of the risk of preterm delivery or the risk of delivery within a selected period of time, comprising:
   (a) obtaining a set of candidate variables based upon data obtained by making querying and examining patients at risk for preterm delivery, designating the candidate variables as a first set of candidate variables and entering them into a computer memory or computer-readable storage medium;
   (b) selecting a set of important selected variables by:
      (i) providing a set of selected important variables and designating it the current set of selected important variables, wherein the set of selected important variables is initially empty;
      (ii) taking candidate variables from the set of candidate variables one at a time and evaluating each by training a computer-based decision-support system on that variable combined with the current set of selected important variables;
      (iii) selecting the best of the candidate variables, wherein the best variable is any one that gives the highest performance of the decision-support system, and if the best candidate variable improves performance compared to the performance of the selected important variables, adding it to the selected important variable set, removing it from the candidate set and continuing evaluating at step (ii), wherein, when the best candidate variable does not improve performance, the process is completed, thereby producing a set of selected variables
   (c) training a decision-support system using the selected final set of important selected variables to produce a test for assessment of the risk of preterm delivery or risk of delivery within a selected time period, wherein assessment of delivery within a selected period of time refers either to prediction of delivery at a particular gestational age, or the risk of delivery within a given time interval
   (d) storing the test for assessment of the risk in a computer memory or on a computer-readable medium.

2. The method of claim 1, wherein in step (i) the candidate variables are obtained from patients and include historical data and/or biochemical data.

3. The method of claim 1, wherein the method of diagnosis assesses the likelihood of preterm delivery.

4. The method of claim 1, wherein the candidate variables include biochemical test data.

5. A computer readable storage medium produced by the method of claim 1.

6. A computer system programmed with instructions for performing the method of claim 1.

7. A computer-readable medium, comprising instructions for performing the method of claim 1.

8. A computer-readable medium, comprising the set variables produced as the output of claim 1.

9. A method of improving the effectiveness of a diagnostic biochemical test for preterm delivery or for the risk of delivery within a selected period of time, comprising:
   (a) selecting a set of important selected variables by the method of claim 1;
   (b) performing the biochemical test on test subjects to obtain test data, wherein the biochemical test is performed before, after or during the selecting step; and
   (c) training a decision-support system using the selected final set of important selected variables and the biochemical test data to produce a test that is more effective in assessing the risk or preterm delivery or delivery within a selected time period than the biochemical test alone.
   (d) storing the test for assessment of the risk in a computer memory or on a computer-readable medium.

10. The method of claim 9, wherein the candidate variables are responses to queries selected from the group consisting of:

Age;
Ethnic origin Caucasian;
Ethnic origin Black;
ethnic origin Asian;
ethnic origin Hispanic;
ethnic origin Native American;
ethnic origin other than the Native American, Hispanic, Asian, Black, or Caucasian;
marital status single;
marital status married;
marital status divorced or separated;
marital status widowed;
marital status living with partner;
marital status other than married, divorced/separated, widowed, or living with partner;
education unknown;
education less than high school;
education high school graduate;
education college or trade school;
patient has Uterine Contractions with or without pain;
patient has intermittent lower abdominal pain, dull, low backache pelvic pressure;
patient has bleeding during the second or third trimester;
patient has menstrual-like or intestinal cramping;
patient has change in vaginal discharge or amount, color, or consistency;
patient is not "feeling right";
pooling;
ferning;
nitrazine;
estimated gestational age (EGA) based on last menstrual period (LMP);
EGA by sonogram (SONO);
EGA by best, wherein EGA by best refers to the best of EGA by SONO and EGA by LMP determined as follows:
  if EGA by SONO is <13 weeks, then EGA best is EGA SONO;
  if the difference by EGA by LMP and EGA by SONO is >2 weeks, then EGA best is EGA by SONO; otherwise EGA best is EGA by LMP;
EGA at sampling;
cervical dilatation (CD);
gravity;
parity-term;
parity-preterm;
parity-abortions, wherein the number of abortions include spontaneous and elective abortions;
parity-living;
sex within 24 hrs prior to sampling for fFN;
vaginal bleeding at time of sampling;
cervical consistency at time of sampling;
uterine contractions per hour as interpreted by the physician;
no previous pregnancies;
at least one previous pregnancy without complications;
at least one preterm delivery;
at least one previous pregnancy with a premature rupture of membrane (PROM);
at least one previous delivery with incompetent cervix;
at least on previous pregnancy with pregnancy induced hypertension (PIH)/preeclampsia;
at least one previous pregnancy with spontaneous abortion prior to 20 weeks; and
at least one previous pregnacy with a complication not listed above.

11. The method of claim 10, wherein the biochemical test is a test that detects fetal fibronectin in cervico/vaginal samples; determines the level of a local inflammatory product protein in cervico/vaginal samples; or estriol or estretol in saliva.

12. The method of claim 9, wherein the candidate variables are responses to queries selected from the group consisting of:
Caucasian;
living with partner;
EGA by sonogram;
EGA at sampling;
estimated date of delivery by best;
cervical dilatation (CM);
Parity-preterm;
vaginal bleeding at time of sampling;
cervical consistency at time of sampling; and
previous pregnancy without complication.

13. The method of claim 9, wherein the candidate variables are responses to queries selected from the group consisting of:
Caucasion;
Uterine contractions with or without pain;
Parity-abortions;
Vaginal bleeding at time of sampling;
Uterine contractions per hour; and
No previous pregnancies.

14. A computer-based diagnostic test produced by the method of claim 4.

15. A method for assessing the risk of delivery prior to completion of 35 weeks of gestation, comprising assessing a subset of variables containing at least three and up to all of the responses to the following queries:
  Ethnic Origin Caucasian;
  Marital Status living with partner;
  EGA by sonogram;
  EGA at sampling;
  estimated date of delivery by best;
  cervical dilatation (CM);
  parity-preterm;
  vaginal bleeding at time of sampling;
  cervical consistency at time of sampling; and
  previous pregnancy without complication, by querying and testing the subject; and
entering the results of the queries and tests into a computer system that comprises a decision-support system that has been trained to assess the the risk of delivery prior to 35 weeks of gestation, and thereby assessing the risk.

16. The method of claim 15, wherein the decision support system is a neural network.

17. The method of claim wherein the decision-support system has been trained using a set of variables that do not include biochemical test data.

18. The method of claim 15, wherein the decision-support system has been trained using a set of variables that do not include the results of a test that detects fetal fibronectin in samples of mammalian body tissue and fluids.

19. The method of claim 18, wherein the first trained neural network comprises a three-layer network containing an input layer, a hidden layer and an output layer, the input layer having seven input nodes, first, second, third, fourth and fifth hidden layer nodes, a hidden layer bias for each hidden layer node, first and second output layer nodes in the output layer, and an output layer bias for each output layer node.

20. The method of claim 19, further including the steps of:
   (c1) applying the observation values and the relevant biochemical test results from the memory means to a plurality of the second neural networks, each one of the first neural networks being trained on the samples of the specified factors with starting weights for each training being randomly initialized;
   (d1) extracting from each one of the first trained neural networks, output value pairs for each one of the first neural networks; and
   (e) forming a linear combination of the first ones of the output value pairs and forming a linear combination of the second ones of the output value pairs, to obtain a confidence index pair, the confidence index pair being the indicator of the risk for delivery in 14 days or fewer days.

21. The method of claim 15, wherein the set of variables further includes the result of a test that detects fetal fibronectin in cervico/vaginal samples.

22. A method for assessing the risk of delivery prior to completion of 35 weeks of gestation in a subject comprising:
   (a) querying and examining the subject to collect observation values reflecting presence and absence of specified clinical data factors and storing the observed clinical data factors in storage means of the computer system, the specified clinical data factors comprising at least four up to all of the factors selected from the group consisting of:
   Ethnic Origin Caucasian, Marital Status living with partner, EGA by sonogram, EGA at sampling, estimated date of delivery by best, cervical dilatation (CM), parity-preterm, vaginal bleeding at time of sampling, cervical consistency at time of sampling, and previous pregnancy without complication;
   (b) applying the observation values from the memory means to a first computer-based decision-support system trained on samples of the specified factors; and thereupon
   (c) extracting from the first decision-support system an output value, wherein the output value is a quantitative objective aid to assess the risk of delivery prior to 35 weeks of gestation.

23. The method of claim 22, wherein the decision-support system comprises a neural network.

24. The method of claim 22, wherein at least five factors are selected.

25. The method of claim 22, wherein the clinical factors further comprise the result of a test that detects fetal fibronectin in cervico/vaginal samples; the result of a test that determines the level of a local inflammatory product protein in cervico/vaginal samples; or the result of a test that assesses estriol or estretol in saliva.

26. The method of claim 25, wherein the selected factors include the result of the test.

27. The method of claim 26, further comprising:
   b1) applying said observation values from said memory means to a plurality of the first decision-support system, wherein each one of the first decision-support systems is trained on the samples of the specified factors with different starting weights for each training;
   c1) extracting from the first decision-support system, output value pairs for each one of said first neural networks; and
   d) forming a linear combination of said first ones of said output value pairs and forming a linear combination of said second ones of said output value pairs, to obtain a confidence index pair, said confidence index pair being said quantitative objective aid.

28. The method of claim 27, wherein the first decision support system is a neural network that comprises a three-layer network containing an input layer, a hidden layer and an output layer, the input layer having eleven input nodes, first, second and third second hidden layer nodes, a hidden layer bias for each hidden layer node, first and second output layer nodes in the output layer, and an output layer bias for each output layer node.

29. The method of claim 27, wherein the first decision support system is a neural network and each of the plurality of first trained neural networks comprises a three-layer network comprising an input layer, a hidden layer and an output layer.

30. The method of claim 22, further comprising:
   b1) applying said observation values from said memory means to a plurality of the first decision-support system, wherein each one of the first decision-support systems is trained on the samples of the specified factors with different starting weights for each training;
   c1) extracting from the first decision-support system, output value pairs for each one of said first neural networks; and
   d) forming a linear combination of said first ones of said output value pairs and forming a linear combination of said second ones of said output value pairs, to obtain a confidence index pair, said confidence index pair being said quantitative objective aid.

31. The method of claim 30, wherein the first decision support system is a neural network that comprises a three-layer network containing an input layer, a hidden layer and an output layer, the input layer having eleven input nodes, first, second and third second hidden layer nodes, a hidden layer bias for each hidden layer node, first and second output layer nodes in the output layer, and an output layer bias for each output layer node.

32. The method of claim 30, wherein the first decision support system is a neural network and each of the plurality of first trained neural networks comprises a three-layer network comprising an input layer, a hidden layer and an output layer.

33. The method of claim 22, wherein the clinical factors further comprise the result of a test that detects fetal fibronectin in mammalian body tissue and fluid samples.

34. In a computer system, a method for assessing the risk of delivery in a subject prior to completion of 35 weeks of gestation, comprising the steps of:
   (a) querying and examining the subject to collect observation values reflecting presence and absence of specified factors and storing the observation factors in storage means of the computer system, the specified factors comprising: Ethnic Origin Caucasian, Marital Status living with partner, EGA by sonogram, EGA at sampling, estimated date of delivery by best, cervical dilatation (CM), parity-preterm, vaginal bleeding at time of sampling, cervical consistency at time of sampling, and previous pregnancy without complication;

(b) testing a patient and obtaining results of the test from the patient, wherein the test detects fetal fibronectin (fFN) in mammalian body tissue and fluid samples, and/or the test determines the level of a local inflammatory product protein in cervico/vaginal samples; and/or of a test that assesses estriol or estretol in saliva, wherein the test is performed prior to, during or after step (a);

(c) applying the observation values and the fFN test results from the memory means to a neural network trained on samples of the specified factors and the test results; and thereupon (d) extracting from the trained neural network an output value pair, the output value pair being a preliminary indicator for the risk of delivery prior to 35 weeks of gestation.

35. The method of claim 34, further including the steps of:

(c1) applying the observation values and the relevant biochemical test results from the memory means to a plurality of the second neural networks, each one of the first neural networks being trained on the samples of the specified factors with starting weights for each training being randomly initialized;

(d1) extracting from each one of the first trained neural networks, output value pairs for each one of the first neural networks; and (e) forming a linear combination of the first ones of the output value pairs and forming a linear combination of the second ones of the output value pairs, to obtain a confidence index pair, the confidence index pair being a final indicator for the risk of delivery prior to 35 weeks of gestation.

36. The method of claim 34, wherein the first trained neural network comprises a three-layer network containing an input layer, a hidden layer and an output layer, the input layer having eleven input nodes, first, second and third hidden layer nodes, a hidden layer bias for each hidden layer node, first and second output layer nodes in the output layer, and an output layer bias for each output layer node.

37. The method of claim 34, wherein the sample is a cervico/vaginal sample.

38. A computer-based diagnostic test produced by the method of claim 24.

39. A computer readable medium or computer memory, comprising a decision-support system produced by the method of claim 24.

40. A computer-readable medium produced by the method of claim 24.

41. A method for assessing the risk for delivery in 7 or fewer days, comprising assessing a subset of variables containing at least three up to all of the following variables:
Ethnic Origin Caucasian;
Uterine contractions with or without pain;
Parity-abortions;
vaginal bleeding at time of sampling;
uterine contractions per hour; and
No previous pregnancies, by querying and testing the subject; and
entering the results of the queries and tests into a computer system that comprises a decision-support system that has been trained to assess the the risk of delivery within seven days, and thereby assessing the risk.

42. The method of claim 41, wherein:
the variables further include the result of a test for to detect fetal fibronectin (fFN) in a cervico/vaginal sample and/or the result of a test that determines the level of a local inflammatory product protein in cervico/vaginal samples and/or the result of a test that assesses estriol or estretol in saliva;
the selected variables include the results of the test; and
the method measures the risk of delivery in 7 days or few days from obtaining the sample for the fFN.

43. The method of claim 42, wherein the decision support system is a neural network.

44. The method of claim 42, wherein the decision-support system has been trained using a set of variables that do not include biochemical test data.

45. The method of claim 41, wherein:
the variables further include the result of a test for to detect fetal fibronectin (fFN) in mammalian body tissue and fluid samples and/or the result of a test that determines the level of a local inflammatory product protein in cervico/vaginal samples and/or the result of a test that assesses estriol or estretol in saliva;
the selected variables include the results of the test; and
the method measures the risk of delivery in 7 days or few days from obtaining the sample for the fFN.

46. A method for assessing in a subject the risk for delivery in 7 days or fewer days, comprising:

(a) querying and examining the subject to collect observation values reflecting presence and absence of specified clinical data factors and storing the observed clinical data factors in storage means of the computer system, the specified clinical data factors comprising at least four up to all of the factors selected from the group consisting of:
Ethnic Origin Caucasian, Marital Status living with partner, EGA by sonogram, EGA at sampling, estimated date of delivery by best, cervical dilatation (CM), parity-preterm, vaginal bleeding at time of sampling, cervical consistency at time of sampling, and previous pregnancy without complication;

(b) applying the observation values from the memory means to a first computer-based decision-support system trained on samples of the specified factors; and thereupon (c) extracting from the first decision-support system an output value, wherein the output value is a quantitative objective aid to assess the risk of delivery prior to 35 weeks of gestation.

47. The method of claim 46, wherein the decision-support system comprises a neural network.

48. The method of claim 46, wherein at least five factors are selected.

49. The method of claim 46, wherein the clinical factors further comprise the result of a test that detects fetal fibronectin in cervico/vaginal sample and/or the result of a test that determines the level of a local inflammatory product protein in cervico/vaginal samples and/or the result of a test that assesses estriol or estretol in saliva.

50. The method of claim 49, wherein the selected factors include the result of the test.

51. The method of claim 50, further comprising:

b1) applying said observation values from said memory means to a plurality of the first decision-support system, wherein each one of the first decision-support systems is trained on the samples of the specified factors with different starting weights for each training;

c1) extracting from the first decision-support system, output value pairs for each one of said first neural networks; and d) forming a linear combination of said first ones of said output value pairs and forming a linear combination of said second ones of said output value pairs, to obtain a confidence index pair, said confidence index pair being said quantitative objective aid.

52. The method of claim 51, wherein the first decision support system is a neural network that comprises a three-layer network containing an input layer, a hidden layer and an output layer, the input layer having seven input nodes, first, second, third, forth and fifth second hidden layer nodes, a hidden layer bias for each hidden layer node, first and second output layer nodes in the output layer, and an output layer bias for each output layer node.

53. The method of claim 51, wherein the first decision support system is a neural network and each of the plurality of first trained neural networks comprises a three-layer network comprising an input layer, a hidden layer and an output layer.

54. The method of claim 46, further comprising:
   b1) applying said observation values from said memory means to a plurality of the first decision-support system, wherein each one of the first decision-support systems is trained on the samples of the specified factors with different starting weights for each training;
   c1) extracting from the first decision-support system, output value pairs for each one of said first neural networks; and
   d) forming a linear combination of said first ones of said output value pairs and forming a linear combination of said second ones of said output value pairs, to obtain a confidence index pair, said confidence index pair being said quantitative objective aid.

55. The method of claim 46, wherein the first decision support system is a neural network that comprises a three-layer network containing an input layer, a hidden layer and an output layer, the input layer having six input nodes, first, second, third, forth and fifth second hidden layer nodes, a hidden layer bias for each hidden layer node, first and second output layer nodes in the output layer, and an output layer bias for each output layer node.

56. The method of claim 46, wherein the first decision support system is a neural network and each of the plurality of first trained neural networks comprises a three-layer network comprising an input layer, a hidden layer and an output layer.

57. The method of claim 46, wherein the clinical factors further comprise the result of a test that detects fetal fibronectin in mammalian body tissue and fluid samples.

58. In a computer system, a method for assessing the risk for delivery in 7 or fewer days, comprising the steps of:
   (a) querying and examining the subject to collect observation values reflecting presence and absence of specified factors and storing the observation factors in storage means of the computer system, the specified factors comprising: Ethnic Origin Caucasian, Uterine contractions with or without pain, Parity-abortions, vaginal bleeding at time of sampling, uterine contractions per hour, prior to and No previous pregnancies;
   (b) testing a patient and obtaining results of the test from the patient, wherein the test detects fetal fibronectin (fFN) in mammalian body tissue and fluid samples, and/or the test determines the level of a local inflammatory product protein in cervico/vaginal samples; and/or of a test that assesses estriol or estretol in saliva, wherein the test is performed prior to, during or after step (a);
   (c) applying the observation values and the fFN test results from the memory means to a second neural network trained on samples of the specified factors and the test results; and thereupon
   (d) extracting from the second trained neural network an output value pair, the output value pair being a preliminary indicator for the risk of delivery in 7 days or few days from obtaining the cervico/vaginal sample.

59. The method of claim 58, further including the steps of:
   (c1) applying the observation values and the relevant biochemical test results from the memory means to a plurality of the second neural networks, each one of the first neural networks being trained on the samples of the specified factors with starting weights for each training being randomly initialized;
   (d1) extracting from each one of the first trained neural networks, output value pairs for each one of the first neural networks; and
   (e) forming a linear combination of the first ones of the output value pairs and forming a linear combination of the second ones of the output value pairs, to obtain a confidence index pair, the confidence index pair being the indicator of the risk for delivery in 7 days or fewer days.

60. The method of claim 58, wherein the first trained neural network comprises a three-layer network containing an input layer, a hidden layer and an output layer, the input layer having seven input nodes, first, second, third, fourth and fifth hidden layer nodes, a hidden layer bias for each hidden layer node, first and second output layer nodes in the output layer, and an output layer bias for each output layer node.

61. The method of claim 58, wherein the clinical factors further comprise the result of a test that detects fetal fibronectin in mammalian body tissue and fluid samples and/or the result of a test that determines the level of a local inflammatory product protein in cervico/vaginal samples and/or the result of a test that assesses estriol or estretol in saliva.

62. A method for assessing the risk for delivery in 14 or fewer days, comprising assessing a subset of variables containing at least three up to all of the following variables:
   Ethnic Origin Hispanic;
   Marital Status living with partner;
   Uterine contractions with or without pain;
   Cervical dilatation;
   Uterine contractions per hour; and
   No previous pregnancies, by querying and testing the subject; and
   entering the results of the queries and tests into a computer system that comprises a decision-support system that has been trained to assess the the risk of delivery within fourteen days, and thereby assessing the risk.

63. The method of claim 62, wherein:
   the variables further include the result of a test for to detect fetal fibronectin (fFN) in a cervico/vaginal sample and/or the result of a test that determines the level of a local inflammatory product protein in cervico/vaginal samples and/or the result of a test that assesses estriol or estretol in saliva;
   the selected variables include the results of the test; and
   the method measures the risk of delivery in 14 days or few days from obtaining the sample for the fFN.

64. The method of claim 63, wherein the decision support system is a neural network.

65. The method of claim 63, wherein the decision-support system has been trained using a set of variables that do not include biochemical test data.

66. The method of claim 63, wherein the decision-support system has been trained using a set of variables that do not include the results of a test that detects fetal fibronectin in cervico/vaginal samples.

67. The method of claim 62, wherein: comprise the result of a test that detects fetal fibronectin in mammalian body tissue and fluid samples and/or the result of a test that determines the level of a local inflammatory product protein in cervico/vaginal samples and/or the result of a test that assesses estriol or estretol in saliva the selected variables include the results of the test; and the method measures the risk of delivery in 14 days or few days from obtaining the sample for the fFN.

68. A method for assessing in a subject the risk for delivery in 14 days or fewer days, comprising:
    (a) querying and examining the subject to collect observation values reflecting presence and absence of specified clinical data factors and storing the observed clinical data factors in storage means of the computer system, the specified clinical data factors comprising at least four up to all of the factors selected from the group consisting of:
    Ethnic Origin Hispanic, Marital Status living with partner, Uterine contractions with or without pain, cervical dilatation, Uterine contractions per hour, and No previous pregnancies;
    (b) applying the observation values from the memory means to a first decision-support system trained on samples of the specified factors; and thereupon
    (c) extracting from the first decision-support system an output value, wherein the output value is a quantitative objective aid to assess the risk of delivery in less than or in 14 days.

69. The method of claim 68, wherein the decision-support system comprises a neural network.

70. The method of claim 68, wherein at least five factors are selected.

71. The method of claim 68, wherein the clinical factors further comprise the result of a test that detects fetal fibronectin in cervico/vaginal samples.

72. The method of claim 68, wherein the selected factors include the result of the test.

73. The method of claim 72, further comprising:
    b1) applying said observation values from said memory means to a plurality of the first decision-support system, wherein each one of the first decision-support systems is trained on the samples of the specified factors with different starting weights for each training;
    c1) extracting from the first decision-support system, output value pairs for each one of said first neural networks; and
    d) forming a linear combination of said first ones of said output value pairs and forming a linear combination of said second ones of said output value pairs, to obtain a confidence index pair, said confidence index pair being said quantitative objective aid.

74. The method of claim 72, wherein the first decision support system is a neural network that comprises a three-layer network containing an input layer, a hidden layer and an output layer, the input layer having seven input nodes, first, second, third, forth and fifth second hidden layer nodes, a hidden layer bias for each hidden layer node, first and second output layer nodes in the output layer, and an output layer bias for each output layer node.

75. The method of claim 72, wherein the first decision support system is a neural network and each of the plurality of first trained neural networks comprises a three-layer network comprising an input layer, a hidden layer and an output layer.

76. The method of claim 68, further comprising:
    b1) applying said observation values from said memory means to a plurality of the first decision-support system, wherein each one of the first decision-support systems is trained on the samples of the specified factors with different starting weights for each training;
    c1) extracting from the first decision-support system, output value pairs for each one of said first neural networks; and
    d) forming a linear combination of said first ones of said output value pairs and forming a linear combination of said second ones of said output value pairs, to obtain a confidence index pair, said confidence index pair being said quantitative objective aid.

77. The method of claim 68, wherein the first decision support system is a neural network that comprises a three-layer network containing an input layer, a hidden layer and an output layer, the input layer having six input nodes, first, second, third, forth and fifth second hidden layer nodes, a hidden layer bias for each hidden layer node, first and second output layer nodes in the output layer, and an output layer bias for each output layer node.

78. The method of claim 68, wherein the first decision support system is a neural network and each of the plurality of first trained neural networks comprises a three-layer network comprising an input layer, a hidden layer and an output layer.

79. The method of claim 68, wherein the clinical factors further comprise the result of a test that detects fetal fibronectin in mammalian body tissue and fluid samples and/or the result of a test that determines the level of a local inflammatory product protein in cervico/vaginal samples and/or the result of a test that assesses estriol or estretol in saliva.

80. In a computer system, a method for assessing the risk for delivery in 14 days or fewer days, comprising the steps of:
    (a) querying and examining the subject to collect observation values reflecting presence and absence of specified factors and storing the observation factors in storage means of the computer system, the specified factors comprising: Ethnic Origin Hispanic, Marital Status living with partner, Uterine contractions with or without pain, cervical dilatation, Uterine contractions per hour, and No previous pregnancies;
    (b) testing a patient and obtaining results of the test from the patient, wherein the test detects fetal fibronectin (fFN) in mammalian body tissue and fluid samples, and/or the test determines the level of a local inflammatory product protein in cervico/vaginal samples; and/or of a test that assesses estriol or estretol in saliva, wherein the test is performed prior to, during or after step (a);
    (c) applying the observation values and the fFN test results from the memory means to a second neural network trained on samples of the specified factors and the test results; and thereupon
    (d) extracting from the second trained neural network an output value pair, the output value pair being a preliminary indicator for the risk of delivery in 14 days or few days from obtaining the cervico/vaginal sample.

81. The method of claim 80, wherein the sample is a cervico/vaginal sample and the test detects fetal fibronectin.

82. A computer system, comprising a neural network or plurality thereof trained for assessing the risk of preterm delivery or imminent delivery within in a predetermined time frame.

83. The system of claim 82, wherein the time frame is 7 days.

84. The system of claim 82, wherein the time frame is 14 days.

85. The system of claim 82, wherein the risk of delivery before 35 weeks is assessed.

* * * * *

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

Figure 3A:
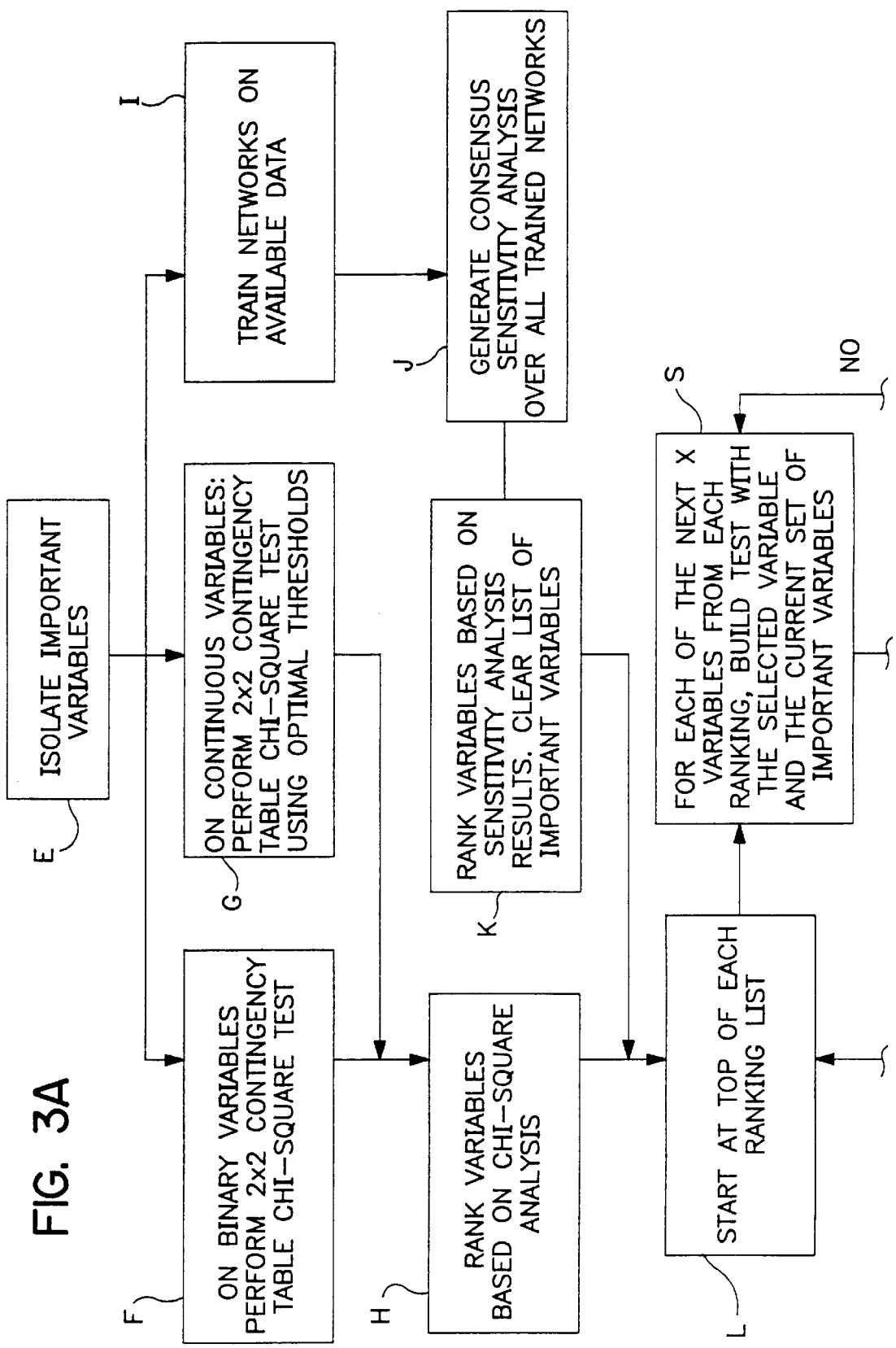
FIG. 3 is a flow chart of the process for isolating important variables.
Figure 3B:
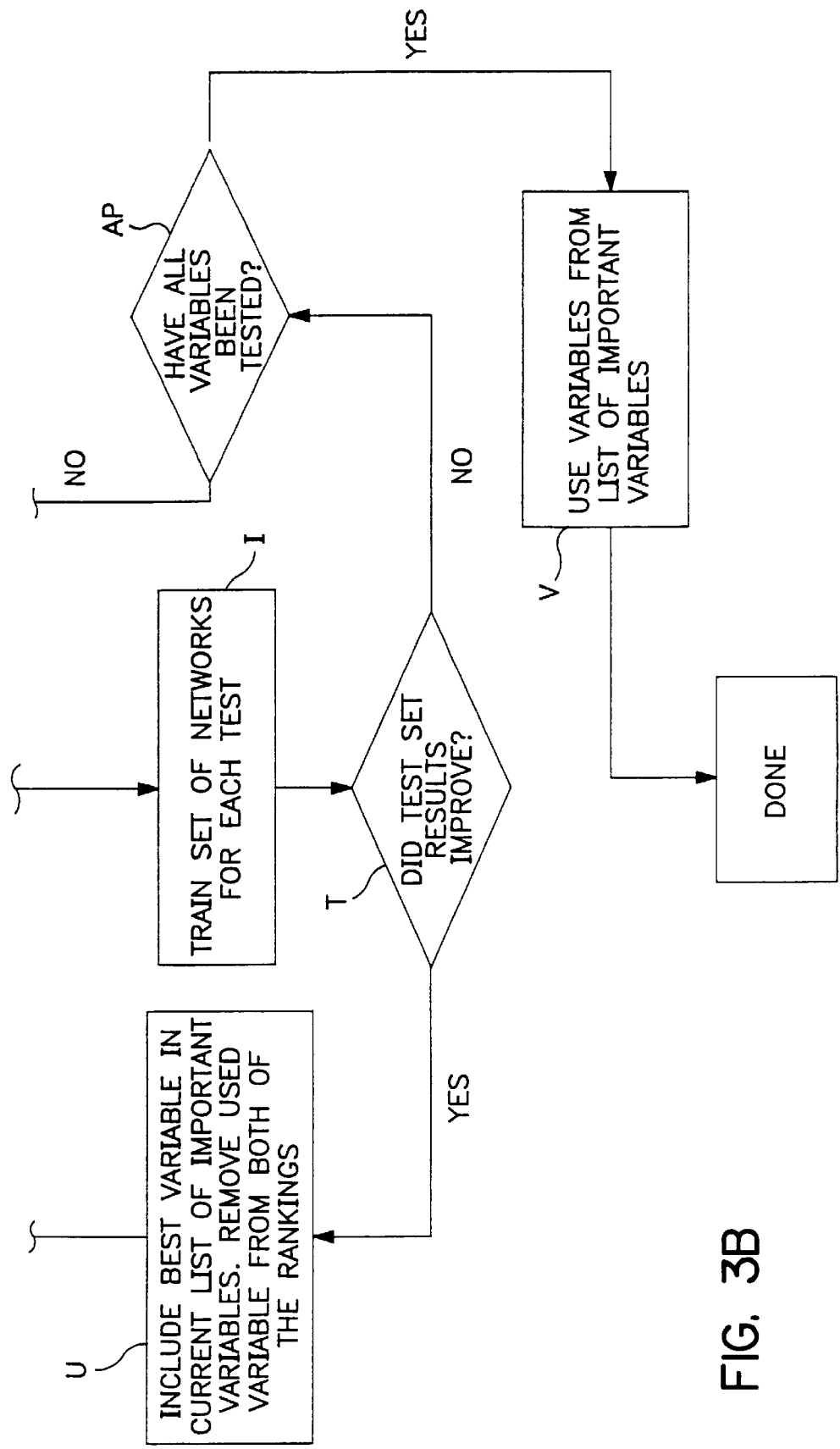

It is certified that error appears in the above-identified patent and that said Letters Patent is hereby corrected as shown below:

Column 1,
Line 44, replace "herewith." with -- herewith on compact discs, copy 1 and copy 2, and stored under the file name Appenixlll.txt, 353KB, created on 05/08/02 pursuant to 37 C.F.R. 1.96(c). The compact discs, copy 1 and copy 2, are identical. The information submitted on the Compact Disc is in compliance with the American Standard Code for Information Interchange (ASCII) in the IBM-PC machine format compatible with the MS-Windows operating system. --;

Column 4,
Line 26, replace "does" with -- do --;

Column 5,
Line 49, delete "these";

Column 6,
Line 2, replace "test is" with -- test's --;
Line 52, replace "," with -- ; --;
Line 58, insert -- of -- between "knowledge" and "the";
Line 67, replace "include" with -- includes --;

Column 7,
Lines 21 and 30, replace "assesses" with -- assess --;
Line 51, replace "test" with -- tests --;

Column 8,
Line 32, replace "FIG.3" with -- Figures 3A-3B are flow charts --;
Line 51, replace "show" with -- shows --;
Line 52, replace "," with -- ; --;

Column 10,
Line 61, delete "used as";

Column 12,
Line 3, replace "is" with -- are --;
Line 55, delete "described in";

UNITED STATES PATENT AND TRADEMARK OFFICE
CERTIFICATE OF CORRECTION

PATENT NO.    : 6,556,977 B1
DATED         : April 29, 2003
INVENTOR(S)   : Lapointe et al.

It is certified that error appears in the above-identified patent and that said Letters Patent is hereby corrected as shown below:

Column 15,
Line 32, replace "FIG. 3 provides a flow chart" with -- Figures 3A-3B provide flow charts --;
Line 45, insert -- Fig. 3A, -- between "(" and "Step E";
Line 48, insert -- Fig. 3A, -- between "(" and "Step J";
Line 53, insert -- Fig. 3A, -- between "(" and "Step K";

Column 16,
Line 49, replace "FIG. 3" with -- Fig. 3A --;

Column 18,
Line 7, replace "FIG. 3" with -- Fig. 3A --;
Line 10, insert -- Fig. 3A, -- between "(" and "Step G";
Line 12, insert -- Fig. 3A, -- between "(" and "Step H";
Line 14, insert -- Fig. 3A, -- between "(" and "Step F";
Line 21, insert -- Fig. 3A, -- between "(" and "Step G";
Line 27, insert -- Fig. 3A, -- between "(" and "Step H";
Line 29, insert -- Fig. 3A, -- between "(" and "Step L";

Column 19,
Line 3, insert -- Fig. 3A, -- between "(" and "Step L";
Line 6, insert -- Fig. 3A, -- between "(" and "Step H";
Line 10, insert -- Fig. 3A, -- between "(" and "Step I";
Line 67, replace "FIG. 3" with -- Fig. 3A --;

Column 20,
Line 2, insert -- Fig. 3A, -- between "(" and "Step T";
Lines 5 and 22, replace "FIG. 3" with -- Fig. 3A --;
Line 5, insert -- Fig. 3A, -- between "(" and "Step S";

Column 25,
Lines 30 and 34, please insert -- described -- between "methods" and "herein";
Line 41, insert -- for -- between "importance," and "example";

Column 26,
Line 17, replace "asssessing" with -- assessing --;

Column 27,
Line 65, replace "week" with -- weeks --;

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

Column 35,
Line 24, replace "assess" with -- assessed --;
Line 45, replace "increasing" with -- increase --;

Column 36,
Line 16, replace "test" with -- tests --;
Line 22, replace "Whilst" with -- While --;

Column 38,
Line 48, replace "5" with -- 5th --;
Line 51, replace "6" with -- 6th --;
Line 64, insert -- is -- between "delivery" and "defined";

Column 39,
Line 1, replace "was" with -- were --;
Line 4, replace "designate" with -- designated --;
Line 9, insert "on" between -- performed -- and -- a --;
Line 12, replace "is" with -- has --;

Column 47,
Line 38, replace "result" with -- results --;

Column 51, line 44 - Column 62, line 65,
Claims 1-3, 9, 10, 13, 14, 19, 20, 25, 27, 34-36, 38-40, 42, 45, 49, 51, 52, 58-61, 63, 67, 71-74, 79, and 80 should read as follows:

1. A computer-based method of assessment of the risk of preterm delivery or the risk of delivery within a selected period of time, comprising:
 (a) obtaining a set of candidate variables based upon data obtained by querying and examining patients at risk for preterm delivery, designating the candidate variables as a first set of candidate variables and entering them into a computer memory or computer-readable storage medium;
 (b) selecting a set of important selected variables by:
  (i) providing a set of selected important variables and designating it the current set of selected important variables, wherein the set of selected important variables is initially empty;

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

(ii) taking candidate variables from the set of candidate variables one at a time and evaluating each by training a computer-based decision-support system on that variable combined with the current set of selected important variables;
      (iii) selecting the best of the candidate variables, wherein best variable is any one that gives the highest performance of the decision-support system, and if the best candidate variable improves performance compared to the performance of the selected important variables, adding it to the selected important variable set, removing it from the candidate set and continuing evaluating at step (ii), wherein, when the best candidate variable does not improve performance, the process is completed, thereby producing a set of selected variables;
  (c) training a decision-support system using the selected final set of important selected variables to produce a test for assessment of the risk of preterm delivery of rish of delivery within a selected time period, wherein assessment of delivery within a selected period of time refers either to prediction of delivery at a particular gestational age, or the risk of delivery within a given time interval; and
  (d) storing the test for assessment of the risk in a computer memory or on a computer-readable medium.

2. The method of claim 1, wherein in step (a) the candidate variables are obtained from patients and include historical data and/or biochemical data.

3. The method of claim 1, wherein the method of assessment assesses the likelihood of preterm delivery.

9. A method of improving the effectiveness of a diagnostic biochemical test for preterm delivery or for the risk of delivery within a selected period of time, comprising:
  (a) selecting a set of important selected variables by the method of claim 1;
  (b) performing the biochemical test on test subjects to obtain test data, wherein the biochemical test is performed before, after or during the selecting step;
  (c) training a decision-support system using the selected final set of important selected variables and the biochemical test data to produce a test that is more effective in assessing the risk of preterm delivery or delivery within a selected time period than the biochemical test alone; and
  (d) storing the test for assessment of the risk in a computer memory or on a computer-readable medium.

UNITED STATES PATENT AND TRADEMARK OFFICE
CERTIFICATE OF CORRECTION

PATENT NO. : 6,556,977 B1  Page 5 of 15
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

10. The method of claim 9, wherein the candidate variables are responses to queries selected from the group consisting of:
    Age;
    Ethnic origin Caucasian;
    Ethnic origin Black;
    ethnic origin Asian;
    ethnic origin Hispanic;
    ethnic origin Native American;
    ethnic origin other than the Native American, Hispanic, Asian, Black, or Caucasian;
    marital status single;
    marital status married;

marital status divorced or separated;
    marital status widowed;
    marital status living with partner;
    marital status other than married, divorced/separated, widowed, or living with partner;
    education unknown;
    education less than high school;
    education high school graduate;
    education college or trade school;
    patient has Uterine Contractions with or without pain;
    patient has intermittent lower abdominal pain, dull, low backache pelvic pressure;
    patient has bleeding during the second or third trimester;
    patient has menstrual-like or intestinal cramping;
    patient has menstrual-like or intestinal cramping;
    patient has change in vaginal discharge or amount, color, or consistency;
    patient is not "feeling right";
    pooling;
    ferning;
    nitrazine;
    estimated gestational age (EGA) based on last menstrual period (LMP);
    EGA by sonogram (SONO);
    EGA by best, wherein EGA by best refers to the best of EGA by SONO and EGA by LMP determined as follows:
        if EGA by SONO is < 13 weeks, then EGA best is EGA SONO;
        if the difference by EGA by LMP and EGA by SONO is > 2 weeks, then EGA best is EGA by SONO; otherwise EGA best is EGA by LMP;

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

Column 51, line 44 - Column 62, line 65 (cont'd),

EGA at sampling;
    cervical Dilatation (CD);
    gravity;
    parity-term;
    parity-preterm;
    parity-abortions, wherein the number of abortions include spontaneous and elective abortions;
    parity-living;
    sex within 24 hrs prior to sampling for fFN;
    vaginal bleeding at time of sampling;
    cervical consistency at time of sampling;
    uterine contractions per hour as interpreted by the physician;
    no previous pregnancies;
    at least one previous pregnancy without complications;
    at least one preterm delivery;
    at least one previous pregnancy with a premature rupture of membrane (PROM);
    at least one previous delivery with incompetent cervix;
    at least one previous pregnancy with pregnancy induced hypertension (PIH)/preeclampsia;
    at least one previous pregnancy with spontaneous abortion prior to 20 weeks; and
    at least one previous pregnancy with a complication not listed above.

13. The method of claim 9, wherein the candidate variables are responses to queries selected from the group consisting of:
    Caucasian;
    Uterine contractions with or without pain;
    Parity-abortions;
    Vaginal bleeding at time of sampling;
    Uterine contractions per hour; and
    No previous pregnancies.

14. A computer-based diagnostic test produced by the method of claim 9.

UNITED STATES PATENT AND TRADEMARK OFFICE
CERTIFICATE OF CORRECTION

PATENT NO.    : 6,556,977 B1
DATED         : April 29, 2003
INVENTOR(S)   : Lapointe et al.

It is certified that error appears in the above-identified patent and that said Letters Patent is hereby corrected as shown below:

<u>Column 51, line 44 - Column 62, line 65 (cont'd),</u>

19. The method of claim 80, wherein the trained neural network comprises a three-layer network containing an input layer, a hidden layer and an output layer, the input layer having seven input nodes, first, second, third, fourth and fifth hidden layer nodes, a hidden layer bias for each hidden layer node, first and second output layer nodes in the output layer, and an output layer bias for each output layer node.

20. The method of claim 80, further including the steps of:
(c1) applying the observation values and the relevant test results from the storage means to a plurality of the neural networks, each one of the neural networks being trained on the samples of the specified factors with starting weights for each training being randomly initialized;
(d1) extracting from each one of the trained neural networks, output value pairs for each one of the neural networks; and
(e) forming a linear combination of the first ones of the output value pairs and forming a linear combination of the second ones of the output value pairs, to obtain a confidence index pair, the confidence index pair being the indicator of the risk for delivery in 14 days or fewer days.

25. A method for assessing the risk of delivery prior to completion of 35 weeks of gestation in a subject comprising:
(a) querying and examining the subject to collect observation values reflecting presence and absence of specified clinical data factors and storing the observed clinical data factors in storage means of the computer system, the specified clinical data factors comprising at least four up to all of the factors selected from the group consisting of:
Ethnic Origin Caucasian, Marital Status living with partner, EGA by sonogram, EGA at sampling, estimated date of delivery by best, cervical dilatation (CM), parity-preterm, vaginal bleeding at time of sampling, cervical consistency at time of sampling, and previous pregnancy without complication;

(b) applying the observation values from the storage means to a first computer-based decision-support system trained on samples of the specified factors; and thereupon
(c) extracting from the first decision-support system an output value, wherein the output value is a quantitative objective aid to assess the risk of delivery prior to 35 weeks of gestation, wherein the clinical factors further comprise the result of a test that detects fetal fibronectin in cervico/vaginal samples; the result of a test that determines the level of a local inflammatory product protein in cervico/vaginal samples; or the result of a test that assesses estriol or estretol in saliva.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

Column 51, line 44 - Column 62, line 65 (cont'd),

27. The method of claim 26, further comprising:
b1) applying said observation values from said storage means to a plurality of the first decision-support system, wherein each one of the first decision-support systems is trained on the samples of the specified factors with different starting weights for each training;
c1) extracting from the first decision-support system, output value pairs for each one of said first decision-support systems; and
d) forming a linear combination of said first ones of said output value pairs and forming a linear combination of said second ones of said output value pairs to obtain a confidence index pair, said confidence index pair being said quantitative objective aid.

34. In a computer system, a method for assessing the risk of delivery in a subject prior to completion of 35 weeks of gestation, comprising the steps of:
(a) querying and examining the subject to collect observation values reflecting presence and absence of specified factors and storing the observation factors in storage means of the computer system, the specified factors comprising: Ethnic Origin Caucasian, Marital Status living with partner, EGA by sonogram, EGA at sampling, estimated date of delivery by best, cervical dilatation (CM), parity-preterm,
vaginal bleeding at time of sampling, cervical consistency at time of sampling, and previous pregnancy without complication;
(b) testing a patient and obtaining results of the test from the patient, wherein the test detects fetal fibronectin (fFN) in mammalian body tissue and fluid samples, and/or the test determines the level of a local inflammatory product protein in cervico/vaginal samples; and/or the test assesses estriol or estretol in saliva, wherein the test is performed prior to, during or after step (a);
(c) applying the observation values and the fFN test results from the storage means to a neural network trained on samples of the specified factors and the test results; and thereupon
(d) extracting from the trained neural network an output value pair, the output value pair being a preliminary indicator for the risk of delivery prior to 35 weeks of gestation.

35. The method of claim 34, further including the steps of:
(c1) applying the observation values and the relevant test results from the storage means to a plurality of the neural networks, each one of the neural networks being trained on the samples of the specified factors with starting weights for each training being randomly initialized;
(d1) extracting from each one of the trained neural networks, output value pairs for each one of the neural networks; and
(e) forming a linear combination of the first ones of the output value pairs and forming a linear combination of the second ones of the output value pairs, to obtain a confidence index pair, the confidence index pair being a final indicator for the risk of delivery prior to 35 weeks of gestation.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

35. The method of claim 34, further including the steps of:
        (c1) applying the observation values and the relevant test results from the storage means to a plurality of the neural networks, each one of the neural networks being trained on the samples of the specified factors with starting weights for each training being randomly initialized;
        (d1) extracting from each one of the trained neural networks, output value pairs for each one of the neural networks; and
        (e) forming a linear combination of the first ones of the output value pairs and forming a linear combination of the second ones of the output value pairs, to obtain a confidence index pair, the confidence index pair being a final indicator for the risk of delivery prior to 35 weeks of gestation.

36. The method of claim 34, wherein the trained neural network comprises a three-layer network containing an input layer, a hidden layer and an output layer, the input layer having eleven input nodes, first, second and third hidden layer nodes, a hidden layer bias for each hidden layer node, first and second output layer nodes in the output layer, and an output layer bias for each output layer node.

38. A computer-based diagnostic test produced by the method of claim 34.

39. A computer readable medium or computer memory, comprising a decision-support system produced by the method of claim 34.

40. A computer-readable medium produced by the method of claim 34.

42. A method for assessing the risk for delivery in 7 or fewer days, comprising assessing a subset of variables containing at least three up to all of the following variables:
        Ethnic Origin Caucasian;
        Uterine contractions with or without pain;
        Parity-abortions;
        vaginal bleeding at time of sampling;
        uterine contractions per hour; and
        No previous pregnancies,
by querying and testing a subject; and
entering the results of the queries and tests into a computer system that comprises a decision-support system that has been trained to assess the the risk of delivery within seven days, and thereby assessing the risk, wherein:
the variables further include the result of a test that detects fetal fibronectin (fFN) in a cervico/vaginal sample and/or the result of a test that determines the level of a local inflammatory product protein in cervico/vaginal samples and/or the result of a test that assesses estriol or estretol in saliva;
        the selected variables include the results of the test; and
        the method measures the risk of delivery in 7 days or few days from obtaining the sample for the fFN.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

Column 51, line 44 - Column 62, line 65 (cont'd),

45. A method for assessing the risk for delivery in 7 or fewer days, comprising assessing a subset of variables containing at least three up to all of the following variables:
        Ethnic Origin Caucasian;
        Uterine contractions with or without pain;
        Parity-abortions;
        vaginal bleeding at time of sampling;
        uterine contractions per hour; and
        No previous pregnancies,
by querying and testing a subject; and
entering the results of the queries and tests into a computer system that comprises a decision-support system that has been trained to assess the the risk of delivery within seven days, and thereby assessing the risk, wherein:
    the variables further include the result of a test that detects fetal fibronectin (fFN) in mammalian body tissue and fluid samples and/or the result of a test that determines the level of a local inflammatory product protein in cervico/vaginal samples and/or the result of a test that assesses estriol or estretol in saliva;
    the selected variables include the results of the test; and
    the method measures the risk of delivery in 7 days or few days from obtaining the sample for the fFN.

49. A method for assessing in a subject the risk for delivery in 7 days or fewer days, comprising:
        (a) querying and examining the subject to collect observation values reflecting presence and absence of specified clinical data factors and storing the observed clinical data factors in storage means of the computer system, the specified clinical data factors comprising at least four up to all of the factors selected from the group consisting of:
        Ethnic Origin Caucasian, Uterine contractions with or without pain, Parity-abortions, vaginal bleeding at time of sampling, uterine contractions per hour, prior to and No previous pregnancies;
        (b) applying the observation values from the storage means to a first computer-based decision-support system trained on samples of the specified factors; and thereupon (c) extracting from the first decision-support system an output value, wherein the output value is a quantitative objective aid to assess the risk of delivery in 7 days or fewer days, wherein the clinical factors further comprise the result of a test that detects fetal fibronectin in cervico/vaginal sample and/or the result of a test that determines the level of a local inflammatory product protein in cervico/vaginal samples and/or the result of a test that assesses estriol or estretol in saliva.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

51. The method of claim 50, further comprising:
        b1) applying said observation values from said storage means to a plurality of the first decision-support system, wherein each one of the first decision-support systems is trained on the samples of the specified factors with different starting weights for each training;
        c1) extracting from the first decision-support system, output value pairs for each one of said first decision-support systems; and
        d) forming a linear combination of said first ones of said output value pairs and forming a linear combination of said second ones of said output value pairs to obtain a confidence index pair, said confidence index pair being said quantitative objective aid.

52. The method of claim 51, wherein the first decision support system is a neural network that comprises a three-layer network containing an input layer, a hidden layer and an output layer, the input layer having seven input nodes, first, second, third, fourth and fifth second hidden layer nodes, a hidden layer bias for each hidden layer node, first and second output layer nodes in the output layer, and an output layer bias for each output layer node.

58. In a computer system, a method for assessing the risk for delivery in 7 days or fewer days, comprising the steps of:
        (a) querying and examining a subject to collect observation values reflecting presence and absence of specified factors and storing the observation factors in storage means of the computer system, the specified factors comprising: Ethnic Origin Caucasian, Uterine contractions with or without pain, Parity-abortions, vaginal bleeding at time of sampling, uterine contractions per hour, prior to and No previous pregnancies;
        (b) testing a patient and obtaining results of the test from the patient, wherein the test detects fetal fibronectin (fFN) in mammalian body tissue and fluid samples, and/or the test determines the level of a local inflammatory product protein in cervico/vaginal samples; and/or the test assesses estriol or estretol in saliva, wherein the test is performed prior to, during or after step (a);
        (c) applying the observation values and the fFN test results from the storage means to a neural network trained on samples of the specified factors and the test results; and thereupon
        (d) extracting from the trained neural network an output value pair, the output value pair being a preliminary indicator for the risk of delivery in 7 days or few days from obtaining the cervico/vaginal sample.

59. The method of claim 58, further including the steps of:
        (c1) applying the observation values and the relevant test results from the storage means to a plurality of the neural networks, each one of the neural networks being trained on the samples of the specified factors with starting weights for each training being randomly initialized;
        (d1) extracting from each one of the trained neural networks, output value pairs for each one of the neural networks; and

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

(e) forming a linear combination of the first ones of the output value pairs and forming a linear combination of the second ones of the output value pairs, to obtain a confidence index pair, the confidence index pair being the indicator of the risk for delivery in 7 days or fewer days.

60. The method of claim 58, wherein the trained neural network comprises a three-layer network containing an input layer, a hidden layer and an output layer, the input layer having seven input nodes, first, second, third, fourth and fifth hidden layer nodes, a hidden layer bias for each hidden layer node, first and second output layer nodes in the output layer, and an output layer bias for each output layer node.

61. The method of claim 58, wherein the specified factors further comprise the result of a test that detects fetal fibronectin in mammalian body tissue and fluid samples and/or the result of a test that determines the level of a local inflammatory product protein in cervico/vaginal samples and/or the result of a test that assesses estriol or estretol in saliva.

63. A method for assessing the risk for delivery in 14 or fewer days, comprising assessing a subset of variables containing at least three up to all of the following variables:
    Ethnic Origin Hispanic;
    Marital Status living with partner;
    Uterine contractions with or without pain;
    Cervical dilatation;
    Uterine contractions per hour; and
    No previous pregnancies,
by querying and testing a subject; and
entering the results of the queries and tests into a computer system that comprises a decision-support system that has been trained to assess the the risk of delivery within fourteen days, and thereby assessing the risk, wherein:

the variables further include the result of a test that detects fetal fibronectin (fFN) in a cervico/vaginal sample and/or the result of a test that determines the level of a local inflammatory product protein in cervico/vaginal samples and/or the result of a test that assesses estriol or estretol in saliva;
    the selected variables include the results of the test; and
    the method measures the risk of delivery in 14 days or few days from obtaining the sample for the fFN.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

67. A method for assessing the risk for delivery in 14 or fewer days, comprising assessing a subset of variables containing at least three up to all of the following variables:
        Ethnic Origin Hispanic;
        Marital Status living with partner;
        Uterine contractions with or without pain;
        Cervical dilatation;
        Uterine contractions per hour; and
        No previous pregnancies,
    by querying and testing a subject; and
    entering the results of the queries and tests into a computer system that comprises a decision-support system that has been trained to assess the
the risk of delivery within fourteen days, and thereby assessing the risk, wherein the variables further comprise the result of a test that detects fetal fibronectin in mammalian body tissue and fluid samples and/or the result of a test that determines the level of a local inflammatory product protein in cervico/vaginal samples and/or the result of a test that assesses estriol or estretol in saliva; the selected variables include the results of the test; and
    the method measures the risk of delivery in 14 days or few days from obtaining the sample for the fFN.

71. A method for assessing in a subject the risk for delivery in 14 days or fewer days, comprising:
        (a) querying and examining the subject to collect observation values reflecting presence and absence of specified clinical data factors and storing the observed clinical data factors in storage means of the computer system, the specified clinical data factors comprising at least four up to all of the factors selected from the group consisting of:
Ethnic Origin Hispanic, Marital Status living with partner, Uterine contractions with or without pain, cervical dilatation, Uterine contractions per hour, and No previous pregnancies;
        (b) applying the observation values from the storage means to a first decision-support system trained on samples of the specified factors; and thereupon
        (c) extracting from the first decision-support system an output value, wherein the output value is a quantitative objective aid to assess the risk of delivery in less than or in 14 days, wherein the clinical factors further comprise the result of a test that detects fetal fibronectin in cervico/vaginal samples and/or the result of a test that determines the level of a local inflammatory product protein in cervico/vaginal samples and/or the result of a test that assesses estriol or estretol in saliva.

72. The method of claim 71, wherein the selected factors include the result of the test.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

<u>Column 51, line 44 - Column 62, line 65 (cont'd),</u>

73. The method of claim 72, further comprising:
        b1) applying said observation values from said storage means to a plurality of the first decision-support system, wherein each one of the first decision-support systems is trained on the samples of the specified factors with different starting weights for each training;
        c1) extracting from the first decision-support system, output value pairs for each one of said first neural networks; and d) forming a linear combination of said first ones of said output value pairs and forming a linear combination of said second ones of said output value pairs, to obtain a confidence index pair, said confidence index pair being said quantitative objective aid.

74. The method of claim 72, wherein the first decision support system is a neural network that comprises a three-layer network containing an input layer, a hidden layer and an output layer, the input layer having seven input nodes, first, second, third, fourth and fifth second hidden layer nodes, a hidden layer bias for each hidden layer node, first and second output layer nodes in the output layer, and an output layer bias for each output layer node.

79. A method for assessing in a subject the risk for delivery in 14 days or fewer days, comprising:
        (a) querying and examining the subject to collect observation values reflecting presence and absence of specified clinical data factors and storing the observed clinical data factors in storage means of the computer system, the specified clinical data factors comprising at least four up to all of the factors selected from the group consisting of:
Ethnic Origin Hispanic, Marital Status living with partner, Uterine contractions with or without pain, cervical dilatation, Uterine contractions per hour, and No previous pregnancies;
        (b) applying the observation values from the storage means to a first decision-support system trained on samples of the specified factors; and thereupon
        (c) extracting from the first decision-support system an output value, wherein the output value is a quantitative objective aid to assess the risk of delivery in less than or in 14 days., wherein the clinical factors further comprise the result of a test that detects fetal fibronectin in mammalian body tissue and fluid samples and/or the result of a test that determines the level of a local inflammatory product protein in cervico/vaginal samples and/or the result of a test that assesses estriol or estretol in saliva.

UNITED STATES PATENT AND TRADEMARK OFFICE
CERTIFICATE OF CORRECTION

PATENT NO. : 6,556,977 B1
DATED : April 29, 2003
INVENTOR(S) : Lapointe et al.

It is certified that error appears in the above-identified patent and that said Letters Patent is hereby corrected as shown below:

Column 51, line 44 - Column 62, line 65 (cont'd),
    80. In a computer system, a method for assessing the risk for delivery in 14 days or fewer days, comprising the steps of:
    (a) querying and examining a subject to collect observation values reflecting presence and absence of specified factors and storing the observation factors in storage means of the computer system, the specified factors comprising: Ethnic Origin Hispanic, Marital Status living with partner, Uterine contractions with or without pain, cervical dilatation, Uterine contractions per hour, and No previous pregnancies;
    (b) testing a patient and obtaining results of the test from the patient, wherein the test detects fetal fibronectin (fFN) in mammalian body tissue and fluid samples, and/or the test determines the level of a local inflammatory product protein in cervico/vaginal samples; and/or the test assesses estriol or estretol in saliva, wherein the test is performed prior to, during or after step (a);
    (c) applying the observation values and the fFN test results from the storage means to a neural network trained on samples of the specified factors and the test results; and thereupon
    (d) extracting from the trained neural network an output value pair, the output value pair being a preliminary indicator for the risk of delivery in 14 days or few days from obtaining the cervico/vaginal sample.

Column 54, line 41 - Column 62, line 3,
Claims 15-18, 21-24, 30-33, 41, 46-48, 54-57, 62, 68-70, and 76-78 should be deleted.

Signed and Sealed this

Eleventh Day of April, 2006

JON W. DUDAS
*Director of the United States Patent and Trademark Office*